(12) United States Patent
de la Fuente

(10) Patent No.: US 10,729,201 B1
(45) Date of Patent: Aug. 4, 2020

(54) IMPACT PROTECTION APPARATUS

(71) Applicant: RLF Industries LLC, Miami, FL (US)

(72) Inventor: Ricardo Lewis de la Fuente, Miami, FL (US)

(73) Assignee: RLF Industries LLC, Miami, FL (US)

( * ) Notice: Subject to any disclaimer, the term of this patent is extended or adjusted under 35 U.S.C. 154(b) by 0 days.

(21) Appl. No.: 16/723,747

(22) Filed: Dec. 20, 2019

Related U.S. Application Data

(63) Continuation-in-part of application No. 15/098,093, filed on Apr. 13, 2016, now Pat. No. 10,512,294, which is a continuation of application No. 14/821,480, filed on Aug. 7, 2015, now Pat. No. 9,339,073, which is a continuation of application No. 14/195,699, filed on Mar. 3, 2014, now abandoned.

(60) Provisional application No. 61/934,499, filed on Jan. 31, 2014, provisional application No. 61/772,791, filed on Mar. 5, 2013, provisional application No. 61/771,453, filed on Mar. 1, 2013.

(51) Int. Cl.
| | | |
|---|---|---|
| *G08B 23/00* | (2006.01) | |
| *A42B 3/12* | (2006.01) | |
| *A63B 71/10* | (2006.01) | |
| *A42B 3/04* | (2006.01) | |
| *A61B 5/00* | (2006.01) | |
| *A61B 5/11* | (2006.01) | |

(52) U.S. Cl.
CPC ............ *A42B 3/121* (2013.01); *A42B 3/044* (2013.01); *A42B 3/046* (2013.01); *A61B 5/11* (2013.01); *A61B 5/4064* (2013.01); *A61B 5/6803* (2013.01); *A61B 5/7282* (2013.01); *A63B 71/10* (2013.01)

(58) Field of Classification Search
CPC ....... A42B 3/121; A42B 5/7282; A42B 71/10; A42B 5/4064; A42B 5/6803; A42B 3/046; A42B 5/11; A42B 3/044; A42B 3/08; A42B 3/085; A42B 1/08; A42B 3/06; A42B 3/067; A41D 13/0512
USPC ......... 340/573.1, 665, 669; 73/12.01; 2/422, 2/425, 421, 461, 468
See application file for complete search history.

(56) References Cited

U.S. PATENT DOCUMENTS

| | | |
|---|---|---|
| 2,071,903 A | 2/1937 | Shively |
| 2,419,661 A | 4/1947 | Staaf |
| 2,705,115 A | 3/1955 | Ewing |
| 2,997,558 A | 8/1961 | Shindledecker et al. |
| 3,008,040 A | 11/1961 | Moore |
| 3,073,922 A | 1/1963 | Miller |
| 3,134,106 A | 5/1964 | Shaffer et al. |
| 3,485,973 A | 12/1969 | Kaiser |
| 3,504,867 A | 4/1970 | Stevenson |
| 3,628,221 A | 12/1971 | Pasbrig et al. |
| 3,649,787 A | 3/1972 | Kasabian |
| 3,671,974 A | 6/1972 | Sims |
| 3,679,152 A | 7/1972 | Stoffel |
| 3,713,329 A | 1/1973 | Munger |
| 3,713,506 A | 1/1973 | Lipschutz |

(Continued)

*Primary Examiner* — Anh V La
(74) *Attorney, Agent, or Firm* — Ulmer & Berne LLP

(57) ABSTRACT

An impact protection apparatus (IPA) may include an impact switch configured to transition from an open-circuit state to a close-circuit state when a force is exerted on the IPA in a first direction and exceeds a force threshold. The IPA may further include a protective headgear and linear and rotational locks that can limit movement of the protective headgear upon a threshold level of pressure or impact.

20 Claims, 37 Drawing Sheets

(56) References Cited

U.S. PATENT DOCUMENTS

| | | |
|---|---|---|
| 3,715,535 A | 2/1973 | Urenda |
| 3,814,346 A | 6/1974 | Carter |
| 3,818,509 A | 6/1974 | Romo et al. |
| 3,834,496 A | 9/1974 | Takada |
| 3,871,599 A | 3/1975 | Takada et al. |
| 3,873,996 A | 4/1975 | Varteressian et al. |
| 3,911,535 A | 10/1975 | Mauron et al. |
| 3,930,682 A | 1/1976 | Booth |
| 3,978,525 A | 9/1976 | Bothwell |
| 4,223,211 A | 9/1980 | Allsen et al. |
| 4,417,702 A | 11/1983 | Fohl |
| 4,422,593 A | 12/1983 | Takada |
| 4,437,623 A | 3/1984 | Wyder |
| 4,462,554 A | 7/1984 | Gyoda |
| 4,470,617 A | 9/1984 | Yamada et al. |
| 4,477,041 A | 10/1984 | Dunne |
| 4,499,741 A | 2/1985 | Harris |
| 4,570,975 A | 2/1986 | Kawaguchi |
| 4,620,677 A | 11/1986 | Nagao et al. |
| 4,667,981 A | 5/1987 | Koide |
| 4,682,791 A | 7/1987 | Ernst et al. |
| 4,773,613 A | 9/1988 | Kawai et al. |
| 4,917,210 A | 4/1990 | Danicek et al. |
| 5,004,178 A | 4/1991 | Kobayashi et al. |
| 5,029,770 A | 7/1991 | Tanaka et al. |
| 5,123,408 A | 6/1992 | Gaines |
| 5,127,671 A | 7/1992 | Yano |
| 5,154,368 A | 10/1992 | Fujimura |
| 5,272,770 A | 12/1993 | Allen et al. |
| 5,299,854 A | 4/1994 | Fujimura et al. |
| 5,371,905 A | 12/1994 | Keim |
| 5,415,431 A | 5/1995 | Omura |
| 5,517,699 A | 5/1996 | Abraham, II |
| 5,539,935 A | 7/1996 | Rush, III |
| 5,581,816 A | 12/1996 | Davis |
| 5,621,922 A | 4/1997 | Rush, III |
| 5,786,553 A | 7/1998 | Zakutin |
| 5,951,476 A | 9/1999 | Beach |
| 5,955,712 A | 9/1999 | Zakutin |
| 6,231,509 B1 | 5/2001 | Johnson et al. |
| 6,619,751 B1 | 9/2003 | Shah |
| 6,784,386 B2 | 8/2004 | Chou et al. |
| 6,810,535 B1 | 11/2004 | Moloney |
| 6,813,782 B2 | 11/2004 | Kintzi et al. |
| 6,826,509 B2 | 11/2004 | Crisco, III et al. |
| 6,874,170 B1* | 4/2005 | Aaron ................ A41D 13/0512 2/468 |
| 6,968,576 B2 | 11/2005 | McNeil et al. |
| 7,037,267 B1 | 5/2006 | Lipson et al. |
| 7,120,941 B2 | 10/2006 | Glaser |
| 7,155,747 B2 | 1/2007 | Baker |
| 7,430,767 B2 | 10/2008 | Nagely |
| 7,509,835 B2 | 3/2009 | Beck |
| 7,526,389 B2 | 4/2009 | Greenwald et al. |
| 7,543,690 B2 | 6/2009 | Eckenstein et al. |
| 7,698,909 B2 | 4/2010 | Hannula et al. |
| 7,743,640 B2 | 6/2010 | Lampe et al. |
| 7,849,525 B2 | 12/2010 | Ghajar |
| 7,891,231 B2 | 2/2011 | Song |
| 7,941,873 B2 | 5/2011 | Nagely et al. |
| 7,981,231 B2 | 7/2011 | Schneider et al. |
| 7,992,421 B2 | 8/2011 | Jeftic-Stojanovski et al. |
| 8,057,415 B2 | 11/2011 | Hipp et al. |
| 8,181,281 B2 | 5/2012 | Nagely et al. |
| 8,191,180 B2 | 6/2012 | Berry |
| 8,191,421 B2 | 6/2012 | Petelenz et al. |
| 8,201,277 B2 | 6/2012 | Olivarez |
| 8,237,521 B1 | 8/2012 | Smith |
| 8,333,357 B2 | 12/2012 | Laughlin |
| 8,341,770 B2 | 1/2013 | Siegler et al. |
| 8,359,672 B2* | 1/2013 | Moelker ................ A42B 3/145 2/181 |
| 8,443,468 B2* | 5/2013 | Minson ................ A42B 3/0473 2/468 |
| 8,466,794 B2 | 6/2013 | Mack et al. |
| 8,528,113 B2 | 9/2013 | Siegler et al. |
| 8,537,017 B2 | 9/2013 | Mack et al. |
| 8,539,815 B2 | 9/2013 | Jeftic-Stojanovski et al. |
| 8,548,768 B2 | 10/2013 | Greenwald et al. |
| 8,554,495 B2 | 10/2013 | Mack et al. |
| 8,554,509 B2 | 10/2013 | Crisco, III et al. |
| 8,561,217 B2 | 10/2013 | Nagely et al. |
| 8,621,673 B1 | 1/2014 | Pietrantonio |
| 9,339,073 B2 | 5/2016 | De La Fuente |
| 10,512,294 B2 | 12/2019 | De La Fuente |
| 2001/0002087 A1 | 5/2001 | Townsend |
| 2003/0088906 A1* | 5/2003 | Baker ................ A42B 3/0473 2/416 |
| 2004/0064874 A1 | 4/2004 | Weaver |
| 2004/0194194 A1 | 10/2004 | McNeil et al. |
| 2004/0255368 A1 | 12/2004 | Baler |
| 2005/0177929 A1 | 8/2005 | Greenwald et al. |
| 2006/0038694 A1 | 2/2006 | Naunheim et al. |
| 2007/0052227 A1 | 3/2007 | Chen |
| 2007/0157371 A1 | 7/2007 | Nagely |
| 2007/0186329 A1 | 8/2007 | Baker |
| 2007/0245464 A1 | 10/2007 | Baker |
| 2007/0271686 A1 | 11/2007 | Rast |
| 2008/0209617 A1 | 9/2008 | Castillo |
| 2009/0064396 A1 | 3/2009 | Ghajar |
| 2009/0158509 A1 | 6/2009 | Ghajar |
| 2010/0005571 A1 | 1/2010 | Moss et al. |
| 2010/0229287 A1 | 9/2010 | Mothaffar |
| 2010/0307223 A1 | 12/2010 | Jeftic-Stojanovski et al. |
| 2011/0060260 A1 | 3/2011 | Siegler et al. |
| 2011/0093999 A1 | 4/2011 | Karlsson et al. |
| 2011/0162131 A1 | 7/2011 | Harty |
| 2011/0181418 A1 | 7/2011 | Mack et al. |
| 2011/0181419 A1 | 7/2011 | Mack et al. |
| 2011/0181420 A1 | 7/2011 | Mack et al. |
| 2011/0184663 A1 | 7/2011 | Mack et al. |
| 2011/0203347 A1 | 8/2011 | Hower et al. |
| 2011/0203871 A1 | 8/2011 | Faye et al. |
| 2011/0219852 A1 | 9/2011 | Kasten |
| 2011/0251802 A1 | 10/2011 | Song |
| 2011/0277225 A1 | 11/2011 | Salkind et al. |
| 2012/0124720 A1 | 5/2012 | Evans et al. |
| 2012/0174302 A1 | 7/2012 | Jenkins, III |
| 2012/0188083 A1 | 7/2012 | Miller, II |
| 2012/0210498 A1 | 8/2012 | Mack |
| 2012/0220893 A1 | 8/2012 | Benzel et al. |
| 2012/0223833 A1 | 9/2012 | Thomas et al. |
| 2012/0278980 A1 | 11/2012 | Chuback |
| 2012/0279311 A1 | 11/2012 | Helmer et al. |
| 2012/0289869 A1 | 11/2012 | Tyler |
| 2012/0306438 A1 | 12/2012 | Howard et al. |
| 2012/0309300 A1 | 12/2012 | Howard et al. |
| 2013/0013243 A1 | 1/2013 | Levine et al. |
| 2013/0060168 A1 | 3/2013 | Chu et al. |
| 2013/0074248 A1 | 3/2013 | Evans et al. |
| 2013/0110415 A1 | 5/2013 | Davis et al. |
| 2013/0118255 A1 | 5/2013 | Callsen et al. |
| 2013/0125296 A1 | 5/2013 | Rabinovitch |
| 2013/0167290 A1 | 7/2013 | Ben Ezra |
| 2013/0205480 A1 | 8/2013 | Nagely et al. |
| 2013/0225998 A1 | 8/2013 | Stergiopoulos et al. |
| 2013/0282308 A1 | 10/2013 | Mack et al. |
| 2013/0305436 A1 | 11/2013 | Castillo |
| 2014/0247129 A1 | 9/2014 | De La Fuente |
| 2015/0342281 A1 | 12/2015 | De La Fuente |
| 2016/0324246 A1 | 11/2016 | De La Fuente |

\* cited by examiner

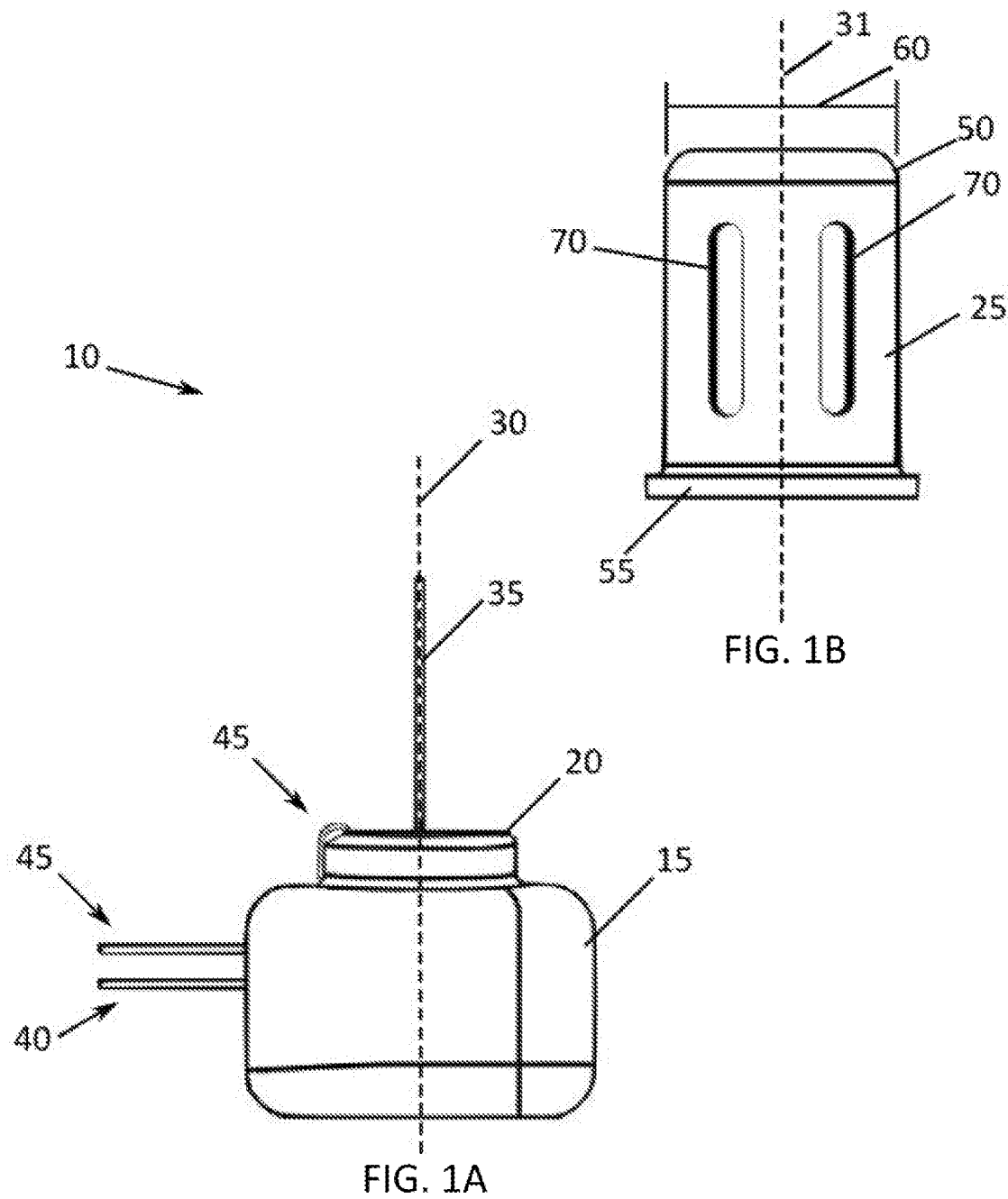

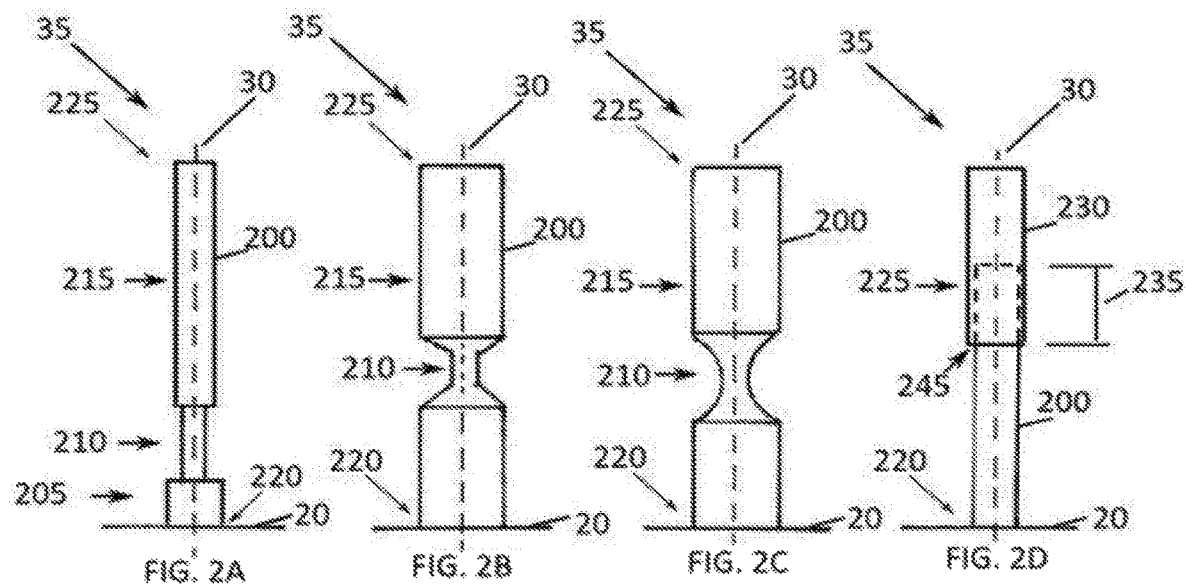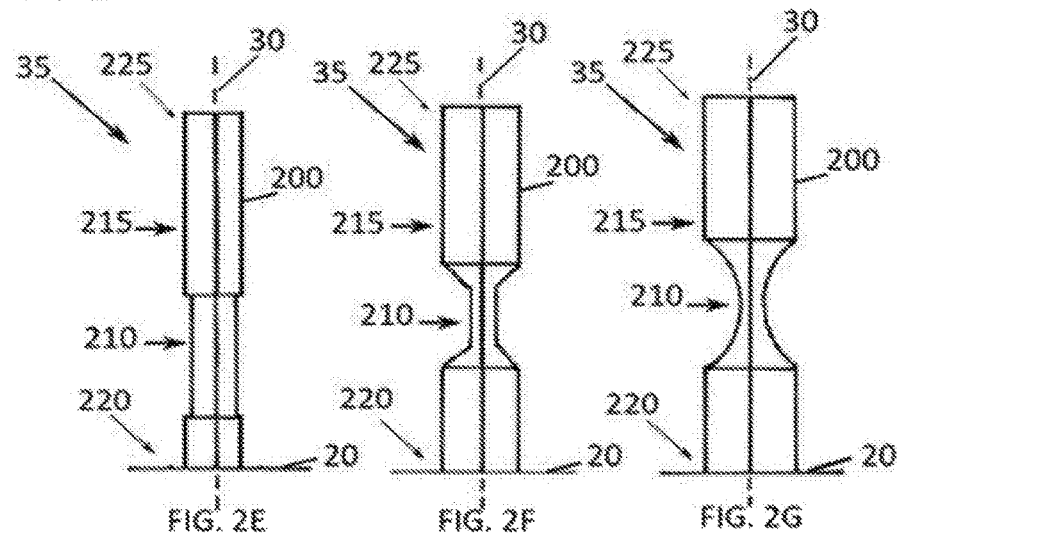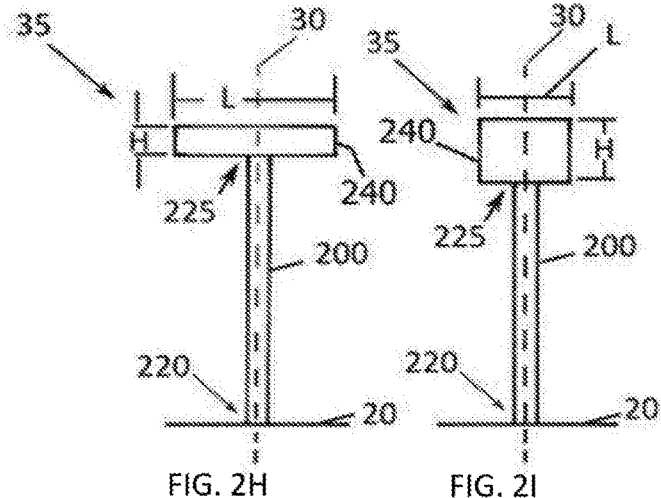

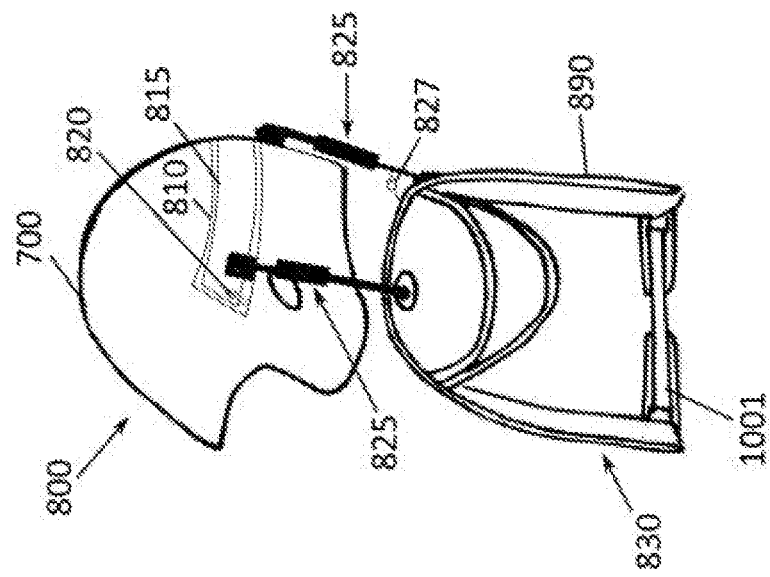
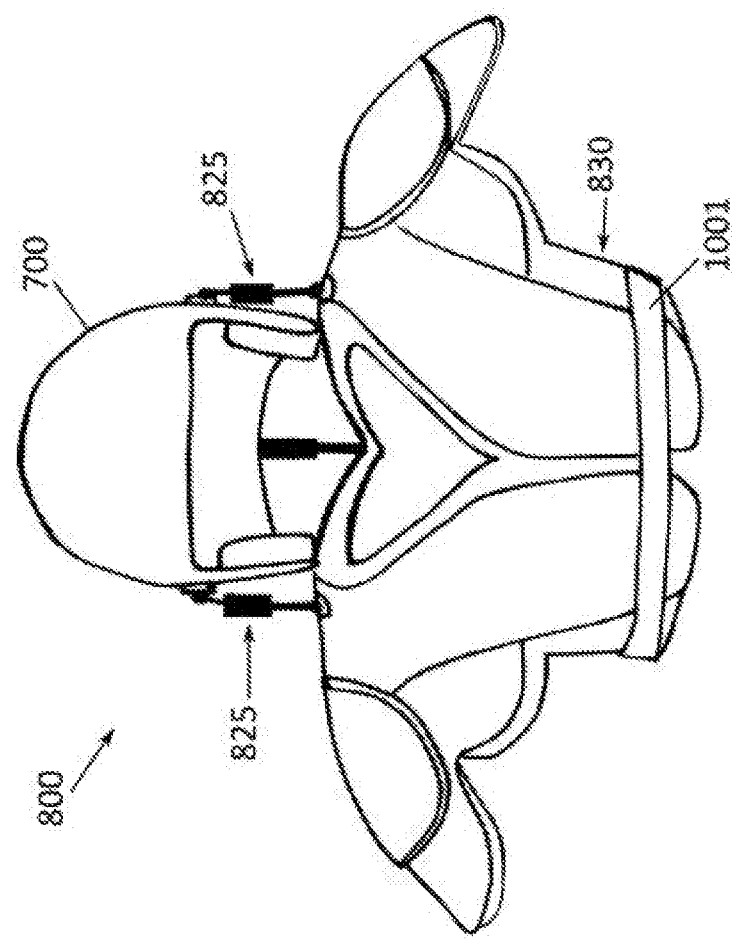

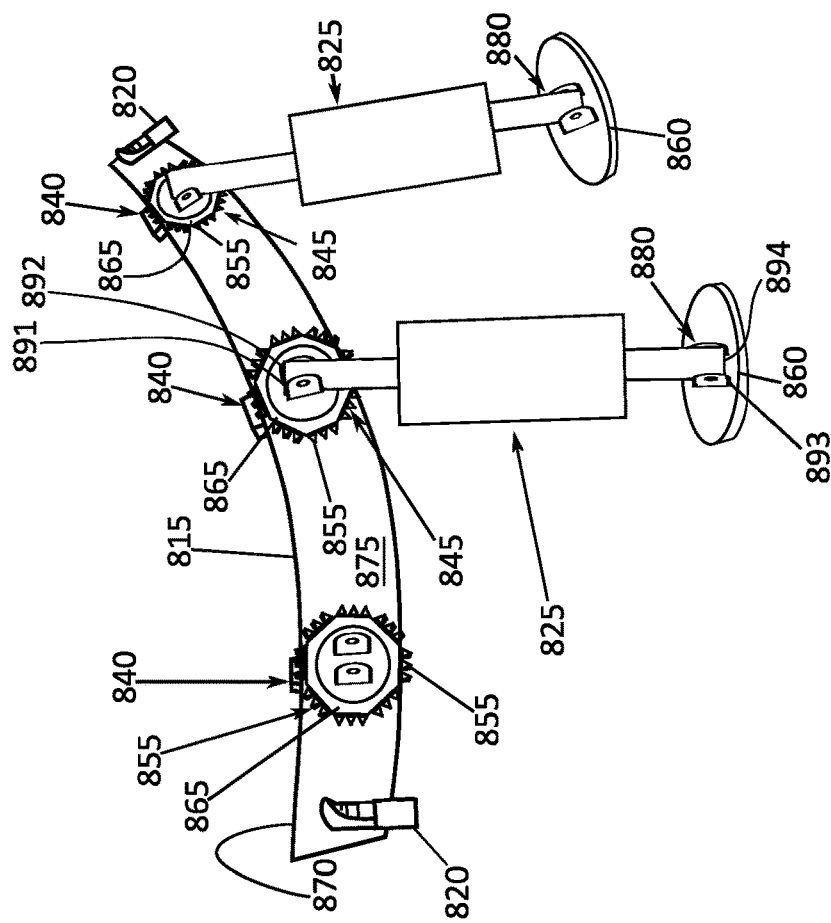
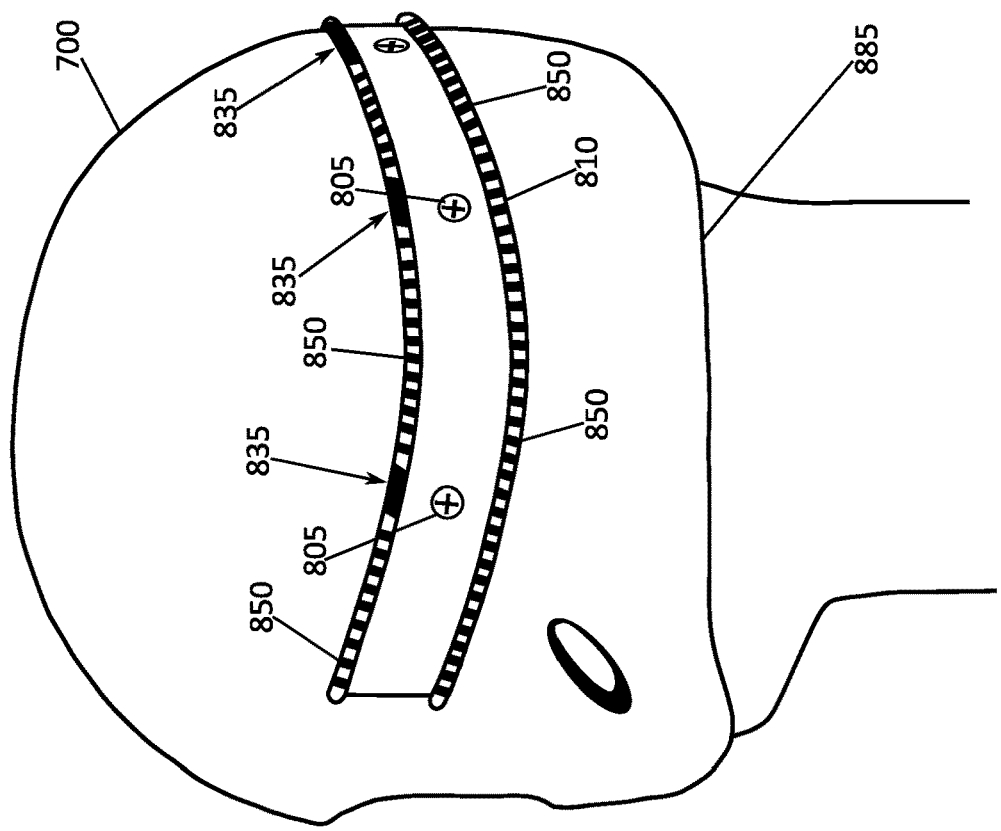
FIG. 9B
FIG. 9A

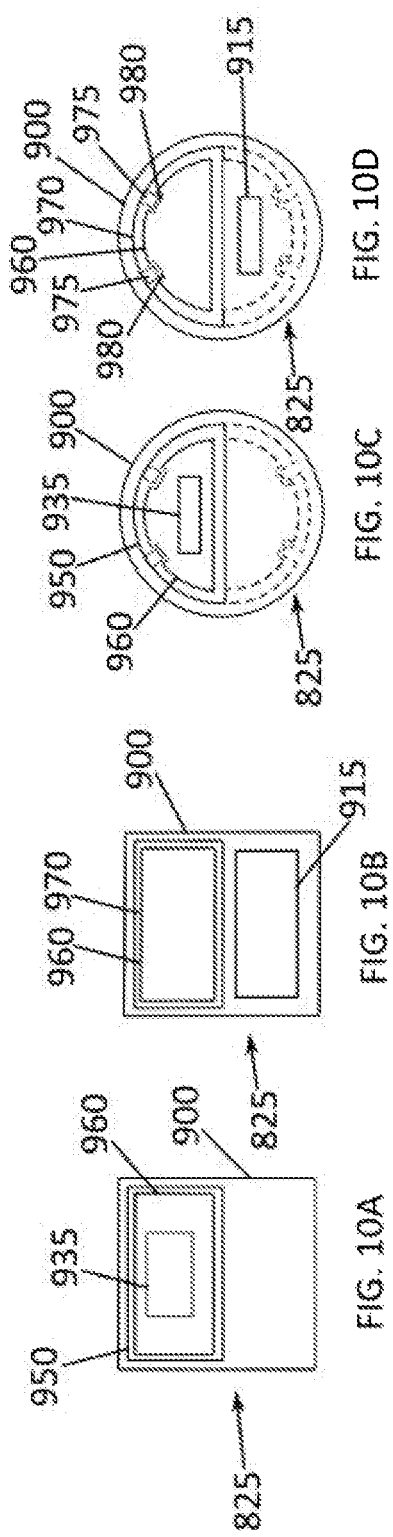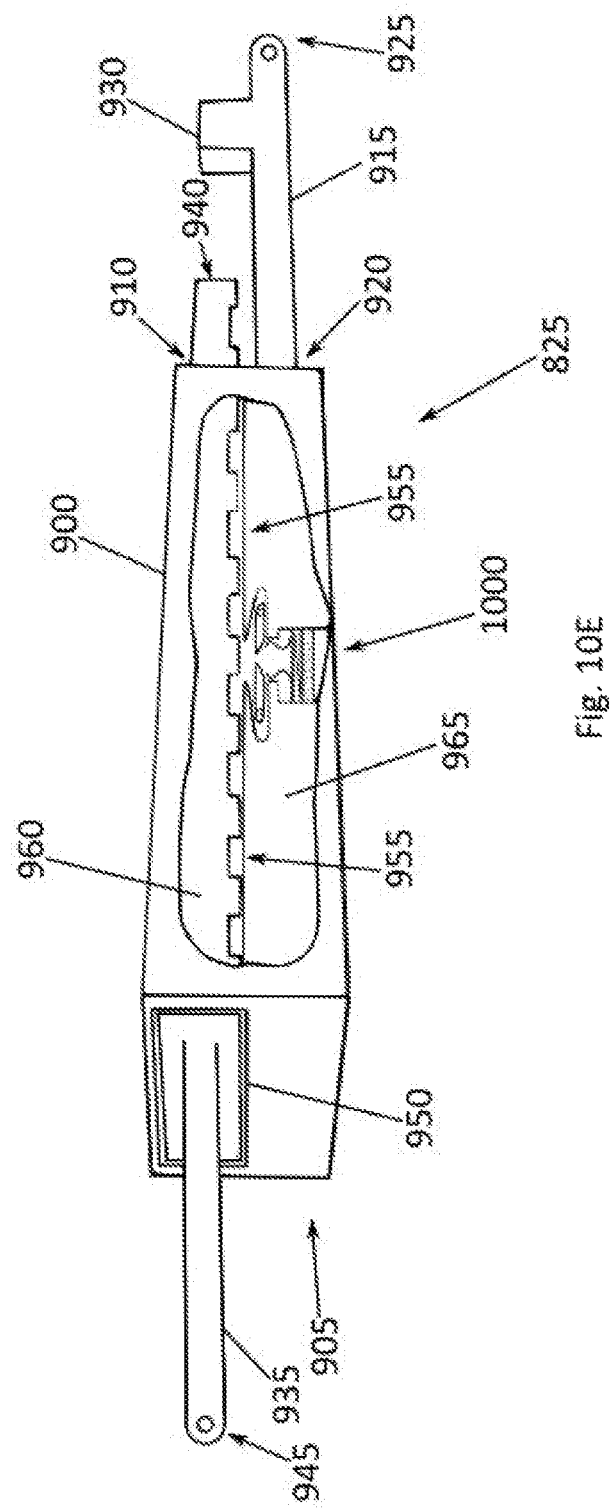

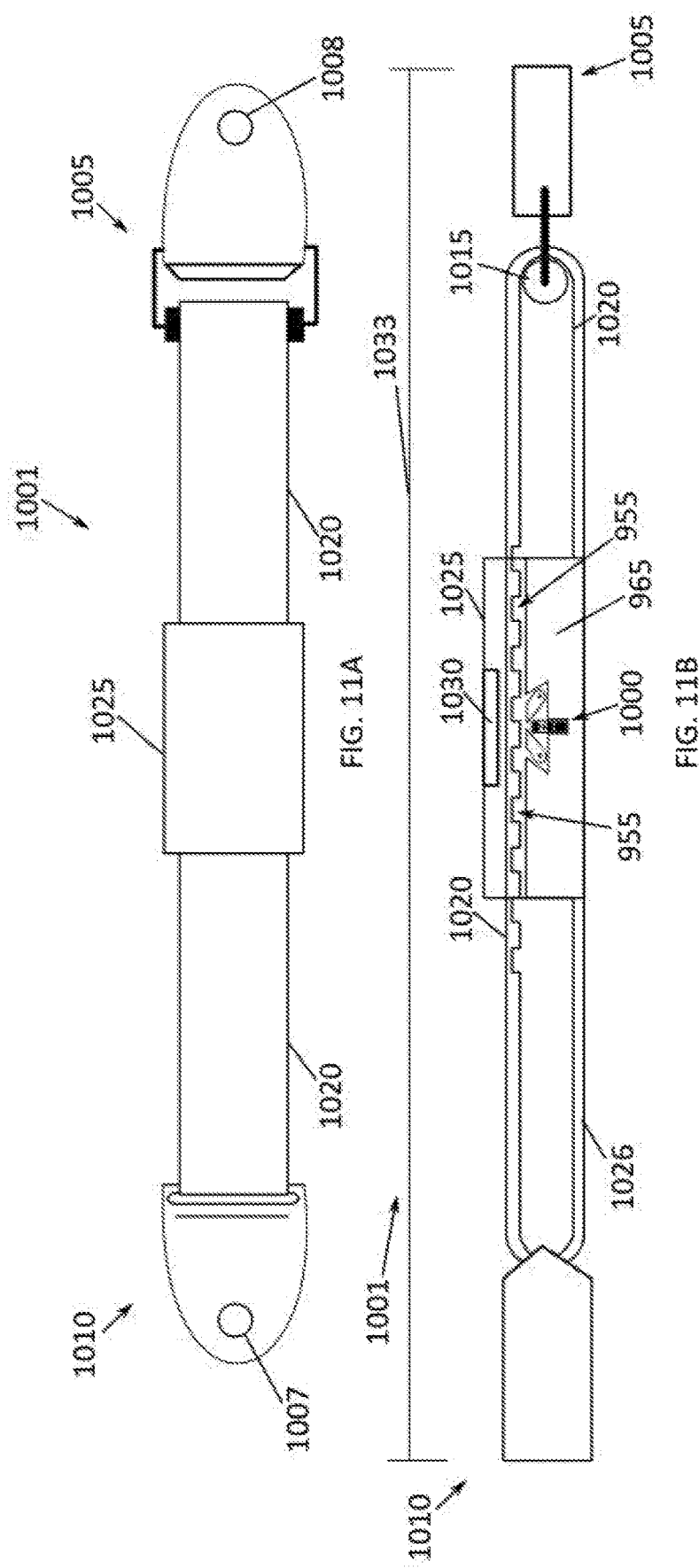

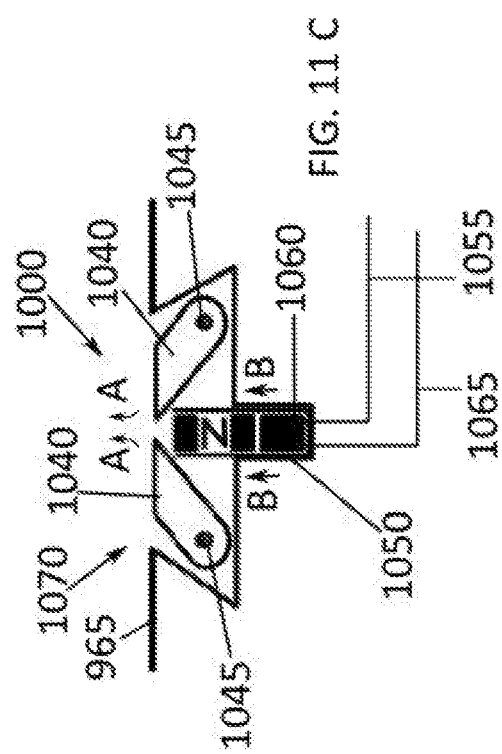

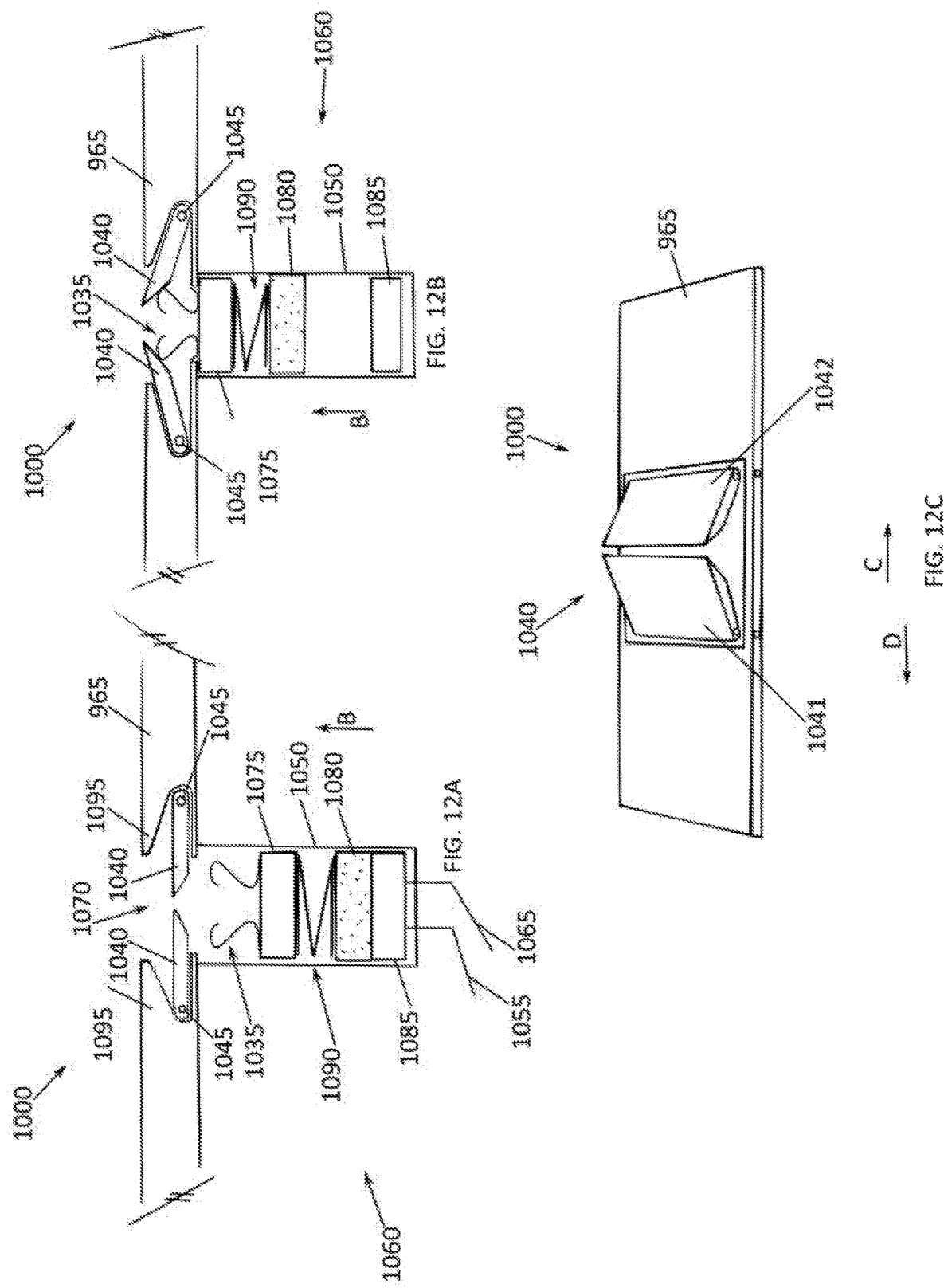

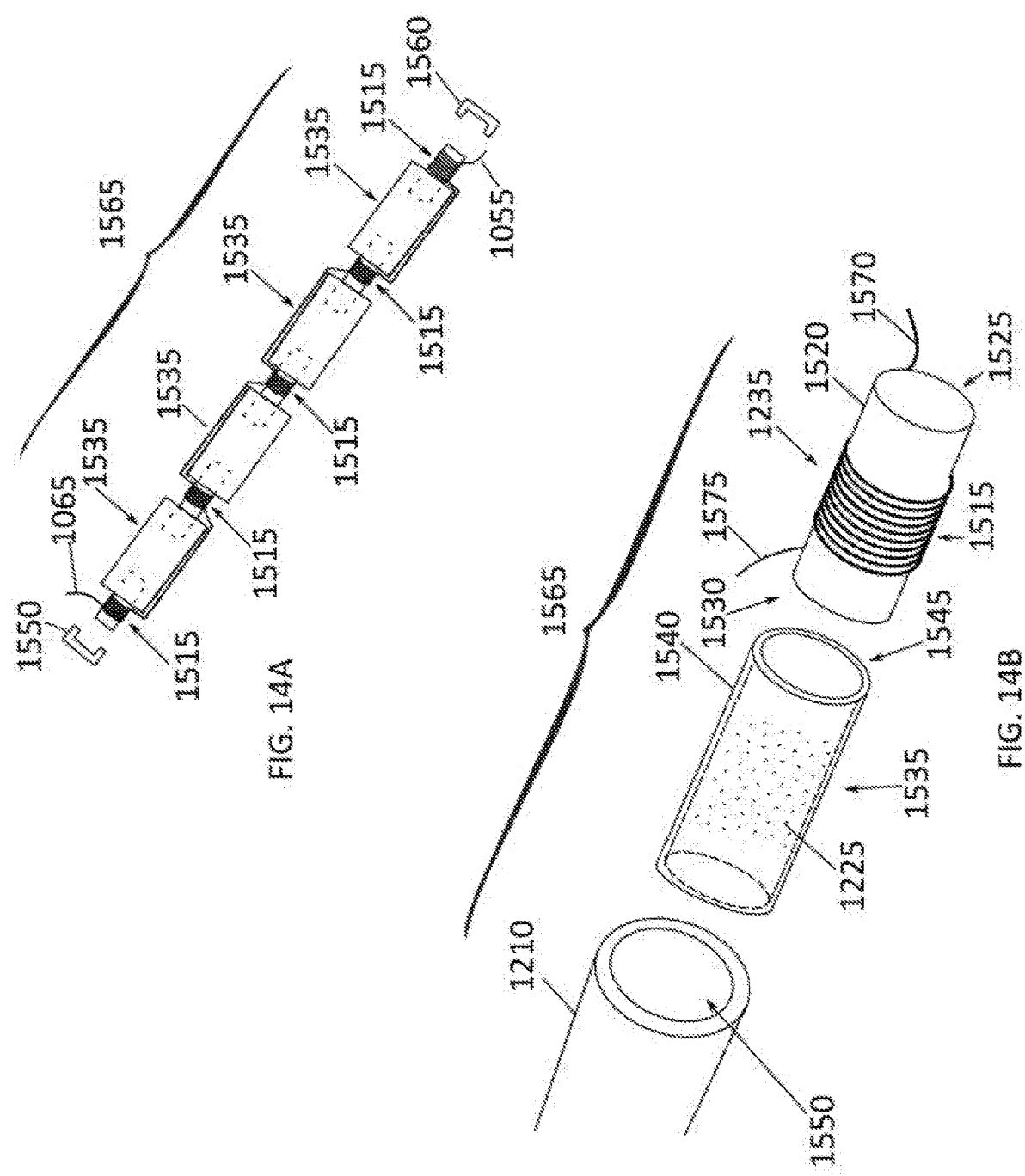

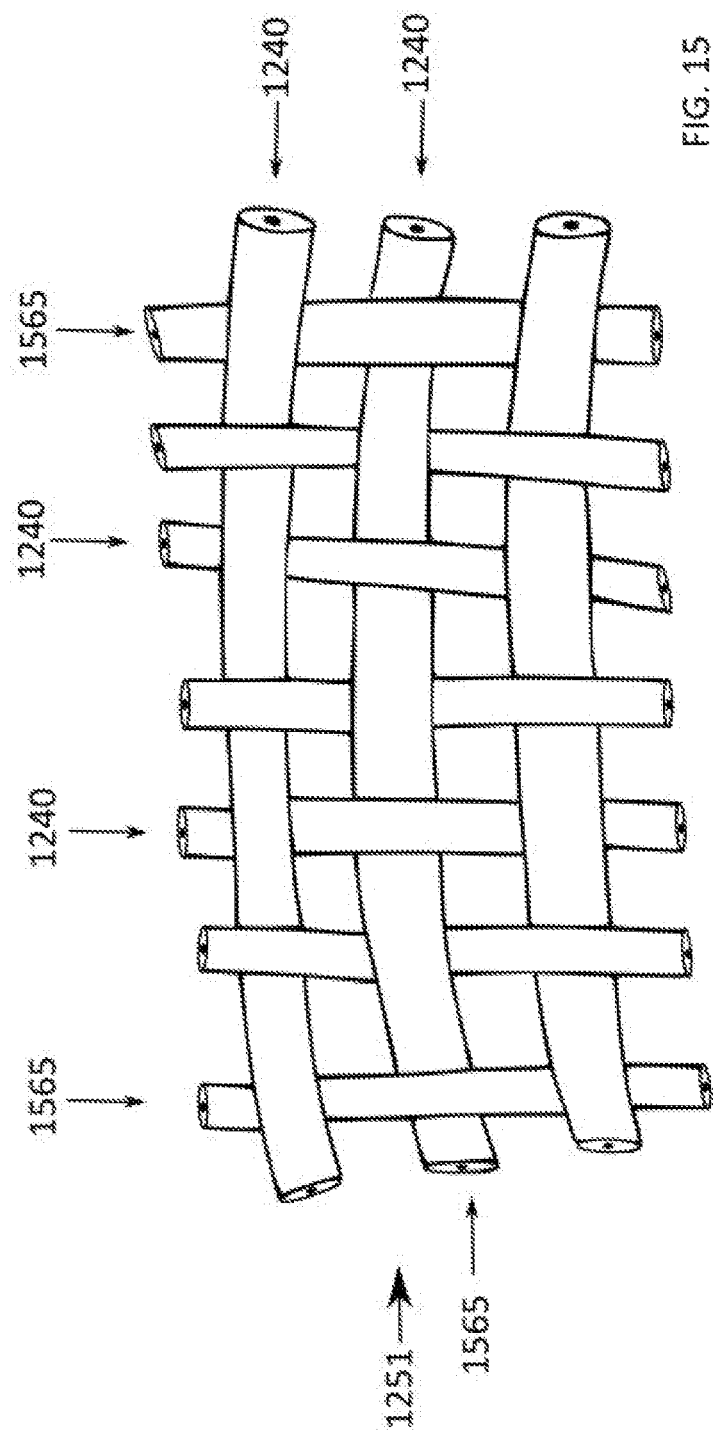

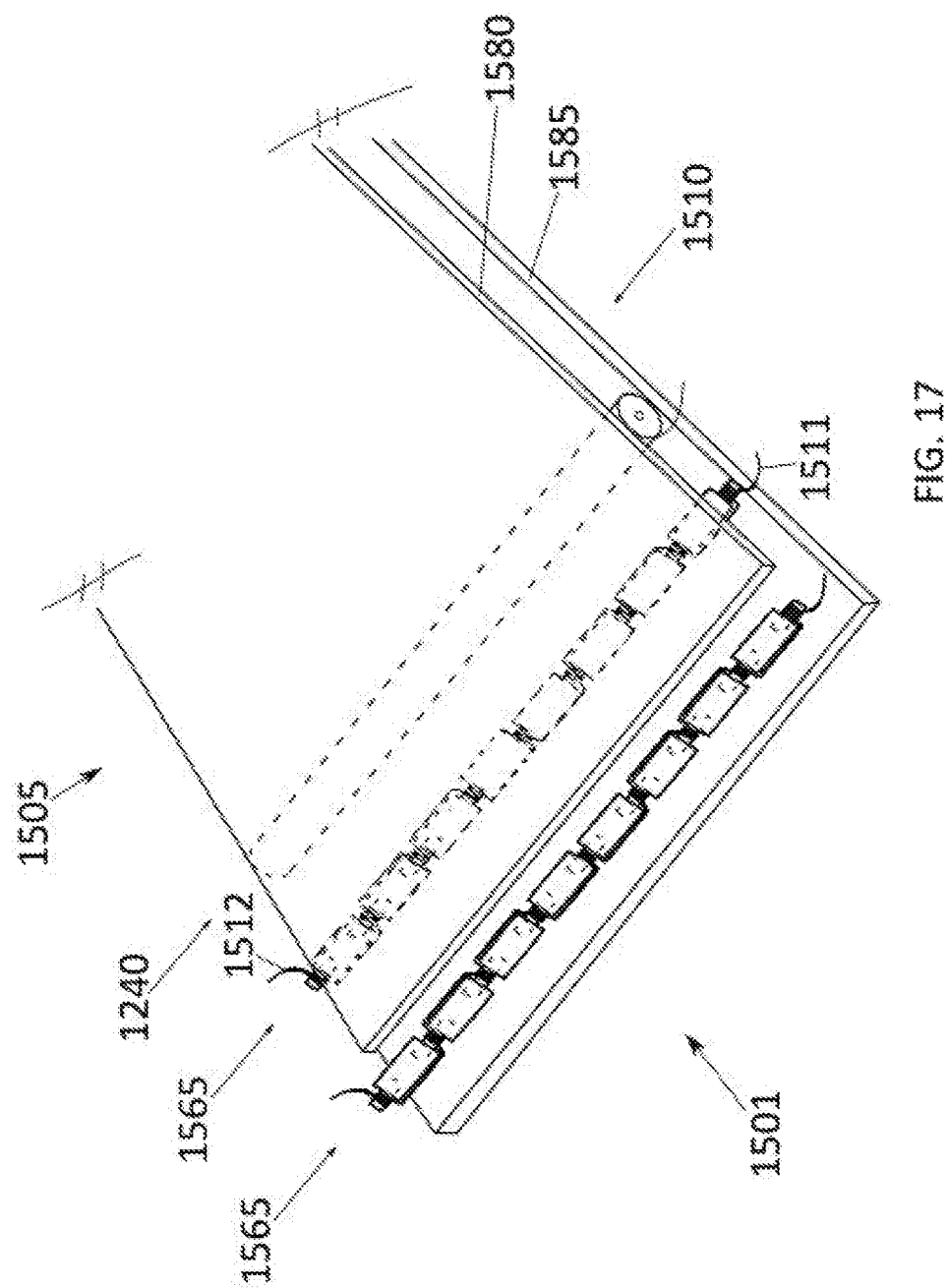

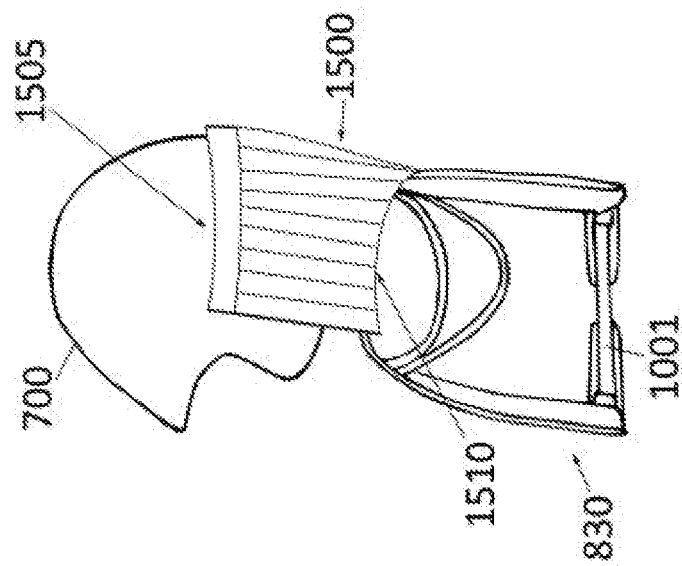
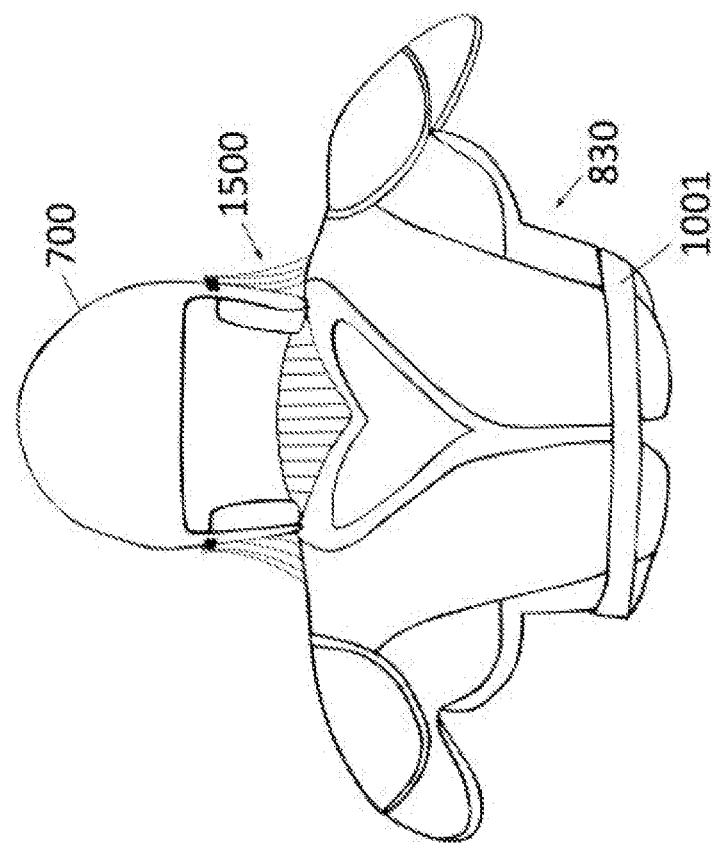

IMPACT PROTECTION APPARATUS

CROSS REFERENCE TO RELATED APPLICATIONS

This application is a continuation-in-part of U.S. patent application Ser. No. 15/098,093, filed on Apr. 13, 2016, entitled "IMPACT AWARENESS DEVICE," which is a continuation of U.S. patent application Ser. No. 14/821,480, filed on Aug. 7, 2015, entitled "IMPACT AWARENESS DEVICE," now U.S. Pat. No. 9,339,073, which is a continuation of U.S. Non-Provisional patent application Ser. No. 14/195,699, filed on Mar. 3, 2014, entitled "IMPACT AWARENESS DEVICE," which claims priority to U.S. Provisional Patent Application Ser. No. 61/934,499, filed on Jan. 31, 2014, entitled "IMPACT AWARENESS DEVICE," U.S. Provisional Patent Application Ser. No. 61/772,791, filed on Mar. 5, 2013, entitled "IMPACT AWARENESS DEVICE," and U.S. Provisional Patent Application Ser. No. 61/771,453, filed on Mar. 1, 2013, entitled "IMPACT AWARENESS DEVICE," the disclosures of which are hereby incorporated herein by reference in their entirety.

TECHNICAL FIELD

The present specification generally relates to an impact protection apparatus for protecting the head and/or vertebral column from injuries after an impact event and, in an embodiment, for determining the likelihood of a head and/or vertebral column injury from an impact event, immobilizing the head and/or diverting impact forces away from the head and/or vertebral column during the duration of the impact event.

BACKGROUND

Protecting the head and vertebral column from the impact forces which may cause injury is a critical objective. Determining the risk and the likelihood that a person has suffered a head and/or vertebral column injury as the result of an impact is often fraught with difficulties ranging from confusion, due to a lack of available information after an impact event, to the need to resume competition despite apparent trauma. Such injuries include bone or cartilage damage to the skull or vertebral column and/or brain injuries such as M.T.B.I. (Mild Traumatic Brain Injury) to brain concussions and contusions.

Accordingly, a need exists for an alternative user worn device for protecting the head and/or vertebral column and determining the likelihood of a head and/or vertebral column injury has occurred in real time as well as after an impact event for the benefit of both the user and outside observers.

SUMMARY

An impact protection apparatus (IPA) may include an impact switch configured to transition from an open-circuit state to a close-circuit state when a force is exerted on the IPA in a first direction and exceeds a force threshold. The IPA may further include a protective headgear and linear and rotational locks that can limit movement of the protective headgear upon a threshold level of pressure or impact.

An impact protection apparatus can be, or be part of, an impact awareness device (IAD) may include an impact switch, or a pressure or force reactive switch, configured to transition from an open-circuit state to a close-circuit state when a force is exerted on the IAD in a first direction and exceeds a force threshold. The impact switch may include a hub including a hub base coupled to the hub and having a central axis centered in the hub base, and a conductive body with a body axis coupled to the hub base, the body axis lies along the central axis. A conductive member may be coupled to the hub base along the central axis. A first wire may be electrically coupled to the conductive member. A second wire may be electrically coupled to the conductive body, The IAD may further include a headliner configured to couple with a protective headgear. The headliner may include a flexible band comprising one or more substrates configured to conform to a headband of the protective headgear, and an electronic circuit coupled to the flexible band and electrically coupled to the switch and wherein when the force threshold is exceeded the electronic circuit transmits an indication signal and a trigger signal. The IAD may further include an indicator circuit coupled to the protective headgear and electrically coupled to the electronic circuit, the indicator circuit is configured to provide an indication of the likelihood of a head and a vertebral column injuries when the indicator signal is received.

In another embodiment, a method of immobilizing a protective headgear in relation to a torso mount may include detecting an impact with impact awareness device (IAD), determining if the force threshold has been exceeded, indicating that the force threshold has been exceeded with the indicator circuit, and transmitting the trigger signal to an interlaced mat. The interlaced may include a flexible magnetorheological (MR) fluid assembly configured to transition from a fluid state to a rigid state when a magnetic field is present. The flexible MR fluid assembly may include a protective tube, a flexible tube disposed within the protective tube, a MR fluid disposed within the flexible tube, a magnetic wire electrically coupled to the electronic circuit and configured to create the magnetic field to transition the MR fluid from the fluid state to the rigid state when the trigger signal is received, one or more inner longitudinal tubes disposed within the flexible tube and enclosing the MR fluid, and a ferromagnetic core disposed within the flexible tube along a tube axis. The one or more flexible MR fluid assemblies may be woven together. The interlaced mat may have a first mat end and a second mat end, the first mat end is removably coupled to the protective headgear and the second mat end is removably coupled to the torso mount. The method may further include transitioning the one or more flexible MR fluid assemblies to the rigid state.

In yet another embodiment, an impact immobilization device to reduce the likelihood of head and a vertebral column injuries, the immobilization device may include an impact awareness device (IAD). The IAD may include an impact switch configured to transition from an open-circuit state to a close-circuit state when a force is exerted on the IAD in a first direction and exceeds a force threshold. The impact switch may include a hub including a hub base coupled to the hub and having a central axis centered in the hub base, and a conductive body with a body axis coupled to the hub base, the body axis lies along the central axis. A conductive member may be coupled to the hub base along the central axis. A first wire may be electrically coupled to the conductive member. A second wire may be electrically coupled to the conductive body, The IAD may further include a headliner configured to couple with a protective headgear. The headliner may include a flexible band comprising one or more substrates configured to conform to a headband of the protective headgear, and an electronic circuit coupled to the flexible band and electrically coupled to the switch and wherein when the force threshold is exceeded the electronic circuit transmits an indication signal and a trigger signal. The IAD may further include an indicator circuit coupled to the protective headgear and electrically coupled to the electronic circuit, the indicator circuit is configured to provide an indication of the likelihood of a head and a vertebral column injuries when the indicator signal is received.

The impact immobilization device may also include a headgear immobilization device electrically coupled to the electronic circuit. The headgear immobilization device may include a mounting base coupled to the protective headgear; a mounting bracket that removably couples to the mounting base and comprises a quick release lever, wherein when the mounting bracket is inserted into the mounting base, the mounting bracket and the mounting base are coupled together and when the quick release lever is actuated, the mounting bracket and the mounting base are decoupled apart; and one or more linear locks. Each linear lock may include a lock housing with a first lock end and a second lock end, a mount with a first mount end and a second mount end, the first mount end is coupled to the first lock end and the second mount end is coupled to the mounting bracket, a rod with a first rod end and a second rod end, a plurality of substantially parallel grooves are disposed along the rod between the first rod end and the second rod end, the first rod end travels through a housing aperture at the second lock end, and the second rod end is coupled to a torso mount, and an interrupter mechanism is disposed within a platform, the platform is disposed within the lock housing and slideably couples with the rod, the interrupter mechanism is configured to restrict the travel of the rod by engaging an individual groove of the plurality of substantially parallel grooves when the trigger signal is received thereby restricting the movement of the protective headgear in relation to the torso mount.

The impact immobilization device may also include a binding immobilizer coupled to the torso mount and electrically coupled to the electronic circuit. The binding immobilizer may include a belt comprising a plurality of substantially parallel grooves, a belt mount coupled to the belt at a distal end, a buckle coupled to the belt at a proximal end, and a roller buckle slideably coupled to the belt between the proximal end and the distal end and configured to matedly couple with the buckle around the torso mount and wherein the interrupter mechanism is disposed within a recess in the belt mount and configured to removably engage a groove of the plurality of substantially parallel grooves when the trigger signal is received.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

FIGS. 1A and 1B depicts an impact switch according to one or more embodiments shown and described herein;

FIGS. 2A through 2I depict several embodiments of a conductive member according to one or more embodiments shown and described herein;

FIG. 8A depicts a front view of a headgear immobilization device according to one or more embodiments shown and described herein;

FIG. 8B depicts a right side view of the headgear immobilization device according to one or more embodiments shown and described herein;

FIG. 9A depicts a mounting brace according to one or more embodiments shown and described herein;

FIG. 9B depicts a mounting bracket according to one or more embodiments shown and described herein;

FIGS. 10A through 10D depict a front cross-sectional view of a linear lock according to one or more embodiments shown and described herein;

FIG. 10E depicts a right side cross-sectional view of the linear lock according to one or more embodiments shown and described herein;

FIG. 11A depicts a top view of a binding immobilizer according to one or more embodiments shown and described herein;

FIG. 11B depicts a cross-sectional view of the binding immobilizer according to one or more embodiments shown and described herein;

FIG. 11C depicts a cross-sectional view of an interrupter mechanism according to one or more embodiments shown and described herein;

FIG. 12A depicts a cross-sectional view of the interrupter mechanism in a free position according to one or more embodiments shown and described herein;

FIG. 12B depicts a cross-sectional view of the interrupter mechanism in an stopped position according to one or more embodiments shown and described herein;

FIG. 12C depicts a top view of the interrupter mechanism according to one or more embodiments shown and described herein;

FIG. 14A depicts a perspective view of a flexible stacked electromagnet assembly according to one or more embodiments shown and described herein;

FIG. 14B depicts an exploded view of the flexible stacked electromagnet assembly according to one or more embodiments shown and described herein;

FIG. 15 depicts a perspective view of an interlaced mat according to one or more embodiments shown and described herein;

FIG. 17 depicts a perspective view of a stacked mat according to one or more embodiments shown and described herein;

FIG. 18A depicts a front view of a vertically aligned magnetic headgear immobilization device according to one or more embodiments shown and described herein;

FIG. 18B depicts a right side view of the vertically aligned magnetic headgear immobilization device according to one or more embodiments shown and described herein;

DETAILED DESCRIPTION

Figure 3:
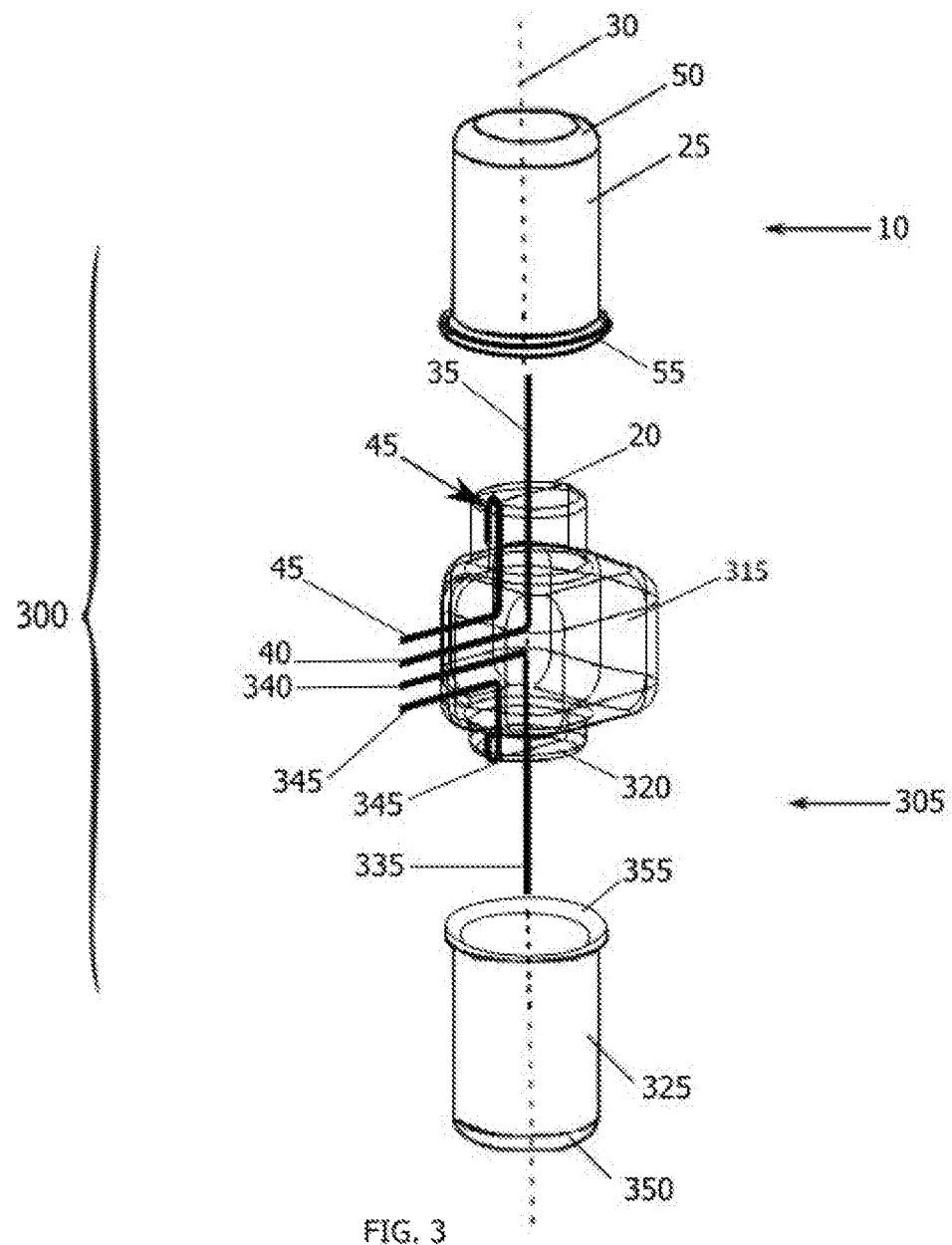
FIG. 3 depicts a double axis impact switch according to one or more embodiments shown and described herein.

The following text sets forth a broad description of numerous different embodiments of the present disclosure. The description is to be construed as exemplary only and does not describe every possible embodiment since describing every possible embodiment would be impractical, if not impossible, and it will be understood that any feature, characteristic, component, composition, ingredient, product, step or methodology described herein can be deleted, combined with or substituted for, in whole or part, with any other feature, characteristic, component, composition, ingredient, product, step or methodology described herein. Numerous alternative embodiments could be implemented, using either current technology or technology developed after the filing date of this patent, which would still fall within the scope of the claims. All publications and patents cited herein are incorporated herein by reference.

Referring generally to FIGS. 1 through 4 with specific numerical reference to FIGS. 1A and 1B, multiple embodiments of an impact switch 10 are shown. The impact switch 10 is an open circuit device (i.e., it will not conduct current (non-conductive) between a first wire 40 and a second wire 45 in a rest state). The impact switch 10 is configured to transition to a close circuit device (i.e., conduct current (conductive) between the first wire 40 and the second wire 45) when a force threshold is exceeded. In other words, when the impact switch 10 is exposed to a force that exceeds the force threshold the impact switch 10 is configured to detect or designed to detect, the impact switch 10 will indicate that the force threshold has been exceed by changing from an open circuit device (non-conductive) to a close circuit device (conductive).

The force that the impact switch 10 responds to may be an impact event (i.e., an event that exerts a force to the impact switch 10 for some duration of time) or it may be a sudden motion event (i.e., an impulse force). The impact switch 10 may be oriented in a specific direction to increase its sensitivity to the force along a specific axis. The impact switch 10 may have many configurations but generally, the impact switch is configured to detect lateral movements, 360 degrees around a central axis 30.

Referring now to FIGS. 1A and 1B, an exploded view of the impact switch 10 is shown. The impact switch 10 includes a hub 15, a hub base 20, a conductive body 25, a conductive member 35, the first wire 40, and the second wire 45. The hub 15 provides the mounting structure for the impact switch 10. The hub 15 may be circular in shape, square, or a combination thereof. The hub 15 may include mounting brackets (not shown) or other hardware to secure the hub 15 to a surface or structure. The hub base 20 is substantially centered upon a central axis 30 and is shaped to matedly couple with the conductive body 25. The hub base 20 may be coupled to the hub 15. In another embodiment, the hub 15 and the hub base 20 may be constructed as one piece. In all embodiments, the hub 15 and the hub base 20 are made from non-conductive materials and may be made from glass, epoxy, ceramic, plastic, coated metal, coated glass, epoxy, ceramic or plastic or other dielectric materials.

The conductive member 35 may be resilient, may be positioned along the central axis 30, and coupled to the hub base 20. The conductive member 35 is configured to lie along the central axis 30 while the impact switch 10 is in a rest state. The rest state is when zero or about zero forces are exerted on the impact switch 10. The conductive member 35 may take on a number of shapes as sizes as shown below in FIGS. 2A through 2I that may determine the force threshold for the impact switch 10.

The conductive body 25 is coupled to the hub base 20. The conductive body 25 may include a body axis 31. The body axis 31 defines the center of the conductive body 25. The body axis 31 may also define the area within the conductive body 25 where the conductive member 35 occupies while in the open-circuit state. In one embodiment, the conductive body 25 is coupled to the hub base 20. In another embodiment, a lip 55 may be coupled to the conductive body 25 and may be configured to matedly couple with the hub base 20 and secure the conductive body 25 to the hub 15. The lip 55 and the hub base 20 may be coupled through an adhesive, crimping, welding, soldering, sealant material, rivet, screw, nail, shrink fitting, interference fit, threaded coupling, or male and female taper fitting.

The shape of the conductive body 25 is configured to be circumferentially and equidistantly surround the conductive member 35. In one embodiment, the conductive body 25 may be cylindrical in shape and centered on the central axis 30. The conductive body 25 may have a body circumference 60. In another embodiment, the conductive body 25 may be spherical in shape and centered on the central axis 30.

The conductive body 25 may include one or more apertures 70 to negate a detection of motion in the impact switch 10 in a specific direction. In other words, the impact switch 10 will not transition to a closed circuit state when the conductive member 35 reacts to an impact and moves to contact the conductive body 25 in a specific direction. The one or more apertures 70 may provide an open space so that the conductive member 35 does not make an electrical connection with the conductive body 25. The one or more apertures 70 allow the impact switch 10 to be customized for specific applications.

In one embodiment, the conductive body 25 may include a cap 50. The cap 50 may be used to prevent the intrusion of dust and other contaminants between the conductive member 35 and the conductive body 25. The cap 50 may also be color coded to indicate the force threshold the impact switch 10 is configured to determine. The cap 50 may be conductive or non-conductive. For example, in one embodiment, the conductive member 35 may be configured to contact the cap 50. In this embodiment, the cap 50 is made from conductive material and the cap 50 is electrically coupled to the conductive body 25. In another embodiment, the conductive member 35 may not be configured to contact the cap 50. In this embodiment, the cap 50 may not be made from conductive material and the cap 50 may be coupled to the conductive body 25 may not be required to be an electrical coupling. The cap 50 may be coupled to the conductive body 25 through an adhesive, crimping, welding, soldering, sealant material, rivet, screw, nail, shrink fitting, an interference fit, threaded coupling, or male and female taper fitting.

In another embodiment, the cap 50 is conductive and covers the distal end of conductive body 25, where the proximal end of the conductive body 25 is coupled to the hub 15. The distal end may include a slanted edge. This slanted edge allows for the impact switch 10 to indicate more than one force threshold. For example, upon impact, the conductive member 35 will transition to a closed-circuit state upon contacting the conductive body 25 on one side where the impact force was induced. The resiliency of the conductive member 35 may be under damped. Therefore, upon returning towards the central axis 30, the conductive member 35 may also electrically contact the slanted edge of cap 50 in an opposite direction and thus transition to a closed-circuit state again and indicate a second, lesser force threshold.

In yet another embodiment instead of the slanted edge, the conductive body 25 may include one or more flat inner wall sections. The flat inner wall sections may allow for the impact switch 10 to indicate more than one force threshold. The conductive member 35 will transition to a close-circuit state upon contacting the conductive body 25 on one side where a force was induced to the impact switch 10. The resiliency of the conductive member 35 may be under damped. Therefore, upon returning towards the central axis 30, the conductive member 35 may also electrically contact the flat inner wall of conductive body 25 in an opposite direction and thus transition to a closed-circuit state again and indicate a second, lesser force threshold.

The first wire 40 and the second wire 45 may be used to electrically couple the impact switch 10 to detection circuitry used to determine the likelihood of a head and/or vertebral column injury from an impact. The first wire 40 may be electrically coupled to the conductive member 35 through the hub 15. The second wire 45 may be electrically coupled to the conductive body 25 through the hub 15. In one embodiment, the conductive body 25 may be removably coupled to the hub base 20. In this embodiment, the second wire 45 may be disposed on an outer surface of the hub base 20 to electrically couple with the conductive body 25 when the conductive body 25 is coupled to the hub base 20 as shown in FIGS. 1A and 1B.

There are several ways to configure the impact switch 10 to determine the desired force threshold. The body circumference 60 of the conductive body 25 may be increased or decreased to change the point of contact between the conductive body 25 and the conductive member 35. A center point of the body circumference 60 lies along the central axis 30. The shape of the conductive body 25 may be changed to change the point of contact between the conductive body 25 and the conductive member 35. The orientation and/or angle of the impact switch 10 to the force applied to the impact switch 10 could be changed to increase or lessen the force and momentum imparted to the conductive member 35. The conductive member 35 may be made of differing materials to change the amount of flex in the shaft 200 of FIGS. 2A through 2I or the conductive member 35 structure could be changed to change the amount of resiliency or flex in the shaft 200. The conductive body 25 may include the slanted edge, the flat wall sections, or a combination of slanted edges and flat wall sections as described above. The properties of the conductive member 35 are described below.

FIGS. 2A through 2I illustrate the many embodiments of the conductive member 35 and the structural changes that may be made to influence the resiliency or flex of the shaft 200 of the conductive member 35. For example, the conductive member 35 may include an upper shaft end 215, a lower shaft end 205, a first shaft end 225, a second shaft end 220, and a neck portion 210. The shaft 200 may be coupled to the hub base 20 by the second shaft end 220. The coupling of the second shaft end 220 to the hub base 20 may serve as an anchor or foundation for the conductive member 35. The first shaft end 225 may not be coupled to any object. Therefore, any force imparted on the impact switch 10 of FIGS. 1A and 1B would move the hub 15, hub base 20, the conductive body 25, and the lower shaft end 205. However, inertia would serve to keep the upper shaft end 215 stationary initially. The structural characteristics and composition of the conductive member 35 would determine when the force threshold is exceeded, or the amount of force needed, for the conductive member 35 to contact the conductive body 25.

The properties of the shaft 200 of the conductive member 35 may be made from any electrically conductive materials including but not limited to copper, steel, metal alloys, conductive carbons such as graphene, stanene, or conductive composites. The conductive member 35 may also vary in the thickness, length, or geometric shape to include circular, square, triangular, hexagonal, and the like. Alternatives to changing the length, thickness, or geometric shape of the shaft 200 may include increasing a hub base height 65 as shown in FIGS. 1A and 1B between the first shaft end 225 and the second shaft end 220. The different hub base height 65 may allow for the same conductive body 25 to be used on several impact switches, each impact switch having a different force threshold depending on the hub base height 65.

FIGS. 2A through 2C illustrate a substantially circular shaped conductive member 35. FIGS. 2F through 2H illustrate a substantially square shaped conductive member 35. FIGS. 2E, 2I, and 2J illustrate structural characteristics made to the upper shaft end 215 of the conductive member 35 to determine the force threshold. Referring now the neck portion 210 of FIGS. 2A through 2C and FIGS. 2F through 2H, the neck portion may change the structural characteristic of the conductive member 35. FIGS. 2A and 2F illustrate the neck portion 210 near the second shaft end 220. These embodiments may be used for low gravity (G) force thresholds where the mass of the shaft 200 above the neck portion 210 towards the first shaft end 225 and the composition of the shaft 200 may serve to set the force threshold of the impact switch 10 of FIGS. 1A and 1B. Example force thresholds may be from about 0.1 Gs (gravitational force) to about 10Gs. In one embodiment, about 8 Gs may be indicative of head and/or vertebral column injury from an impact. FIGS. 2B and 2F illustrate the neck portion 210 equidistance between the first shaft end 225 and the second shaft end 220. FIGS. 2C and 2G illustrate the neck portion 210 towards the first shaft end 225 and may be used for high force threshold.

The shape of the neck portion 210 may also be changed to influence the force threshold of the impact switch 10 of FIGS. 1A and 1B. As illustrated in FIGS. 2A and 2E, a sharp transition from the upper shaft end 215 and the lower shaft end 205 to the neck portion 210. The sharp transition may provide for a sharp change in the force threshold of the conductive member 35 from a conductive member 35 without a neck portion 210 and made from the same composition. FIGS. 2B and 2F illustrate a slight taper in the transition from the upper shaft end 215 and the lower shaft end 205 to the neck portion 210. The slight taper in the transition may serve to increase the robustness of the conductive member (i.e., the sharp transition of FIGS. 2A and 2E may fatigue over time and use) and serve to provide a more accurate force threshold determination of the impact switch 10. FIGS. 2C and 2G illustrate a gradual taper of the transition between the upper shaft end 215 and the lower shaft end 205 to the neck portion 210. The gradual taper of the transition may provide for a minimal change in the force threshold of the conductive member 35 from a conductive member 35 without a neck portion 210 and made from the same composition.

The combination of the position of the neck portion 210 between the first shaft end 225 and the second shaft end 220 and the transition of the upper shaft end 215 and the lower shaft end 205 to the neck portion 210 changes the force threshold of the impact switch 10.

FIG. 2D illustrates a conductive tube 230 slideably coupled to the shaft 200 of the conductive member 35. An overlap distance 235 is defined as the distance between the first shaft end 225 and the lower tube end 245. The conductive tube 230 is electrically coupled to the conductive member 35. The conductive tube 230 is coaxially aligned with the conductive member 35 along the central axis 30. The overlap distance 235 may be changed to determine the force threshold of the impact switch 10.

FIGS. 2H and 2I illustrate a disk 240 coupled to the first shaft end 225 of the shaft 200. The disk 240 may include the dimensions of a length L and a height H that may be used to determine the force threshold of the impact switch 10. The disk 240 may be the part of the conductive member 35 that makes contact with the conductive body 25. The tighter the tolerance between the disk 240 and the conductive body 25 (i.e., the larger the length L is) the lower the G rating of the force threshold is. The length L may never be greater than the body circumference C in FIGS. 1A and 1B. The height H may be increased to increase the mass of the disk 240. Increase mass will increase the inertia of the disk and increase the force threshold of the impact switch 10. The shaft 200 is resilient and reacts to an impact. The disk 240 does not function to be resilient and provides for a consistent and repeatable transition to the closed-circuit state when the force threshold is reached. The disk 240 may be a separate piece that is attached to the shaft 200 or the shaft 200 and the disk 240 may be made from the same block of material.

It should be understood that multiple combinations may be used to configure the conductive member 35 and determine the force threshold of the impact switch 10. In one embodiment, more than one neck portion 210 may be used in the shaft 200. In another embodiment, more than one neck portion 210 may be used where each neck portion 210 has a different transition between the shaft 200 and the neck portion 210. In yet another embodiment, the disk 240 embodiments of FIGS. 2H and 2I and the conductive tube embodiment 230 of FIG. 2D may include the neck portion 210 in the shaft 200.

FIG. 3 illustrates a double impact switch 300 where the impact switch 10 and a second impact switch 305 is coaxially aligned with each other along the central axis 30. The second impact switch 305 and impact switch 10 may share a double hub 315. The double hub 315 may include the hub base 20 and a second hub base 320. The double hub 315 may include all the properties of the hub 15 described above to include that it made from non-conductive materials and may serve as a conduit for the first wire 40, the second wire 45, a third wire 340, and a fourth wire 345. Referring to the second switch 305, the fourth wire 345 may be disposed through the double hub 315 and may be configured to electrically couple with a second conductive body 325. The third wire 340 may also be disposed through the double hub 315 and may be electrically coupled to a second conductive member 335. The second conductive member 335 may be coupled to the second hub base 320, be coaxially aligned with the conductive member 35, and may have a different structure characteristic and composition so that the second conductive member 335 of the second switch 305 has a different force threshold, or second force threshold, from the force threshold, or first force threshold, of the impact switch 10. In another embodiment, the first force threshold may be about equal to the second force threshold. In all embodiments, the discussion above concerning the conductive member 35 applies to the second conductive member 335.

The second conductive body 325 may have a second cap 350. The second cap 350 may be used to prevent the intrusion of dust and other contaminants between the second conductive member 335 and the second conductive body 325. The second cap 350 may also be color coded to indicate the force threshold the second switch 305 is configured to determine. The second cap 350 may be conductive or non-conductive. For example, in one embodiment, the second conductive member 335 may be configured to contact the second cap 350. In this embodiment, the second cap 350 is made from conductive material and the second cap 350 is electrically coupled to the second conductive body 325. In another embodiment, the second conductive member 335 may not be configured to contact the second cap 350. In this embodiment, the second cap 350 may not be made from conductive material and the second cap 350 may be coupled to the second conductive body 325 may not be required to be an electrical coupling. The second cap 350 may be coupled to the second conductive body 325 through an adhesive, crimping, welding, soldering, sealant material, rivet, screw, nail, shrink fitting, an interference fit, threaded coupling, or male and female taper fitting.

In another embodiment, the second cap 350 is conductive and covers the distal end of second conductive body 325, where the proximal end of the second conductive body 325 is coupled to the double hub 315. The distal end may include a slanted edge. This slanted edge allows for the double impact switch 300 to indicate more than one force threshold. For example, upon impact, the second conductive member 335 will transition to a closed-circuit state upon contacting the second conductive body 325 on one side where the impact force was induced. The resiliency of the second conductive member 335 may be under damped. Therefore, upon returning towards the second switch axis, the second conductive member 335 may also electrically contact the slanted edge of second cap 350 in an opposite direction and thus transition to a closed-circuit state again and indicate a second, lesser force threshold from the impact switch 10.

In yet another embodiment instead of the slanted edge, the second conductive body 325 may include one or more flat inner wall sections. The flat inner wall sections may allow for the double impact switch 300 to indicate more than one force threshold. The second conductive member 335 will transition to a close-circuit state upon contacting the second conductive body 325 on one side where a force was induced to the double impact switch 300. The resiliency of the second conductive member 335 may be under damped. Therefore, upon returning towards the second switch axis, the second conductive member 335 may also electrically contact the flat inner wall of second conductive body 325 in an opposite direction and thus transition to a closed-circuit state again and indicate a second, lesser force threshold from the second impact switch 305.

Figure 4:
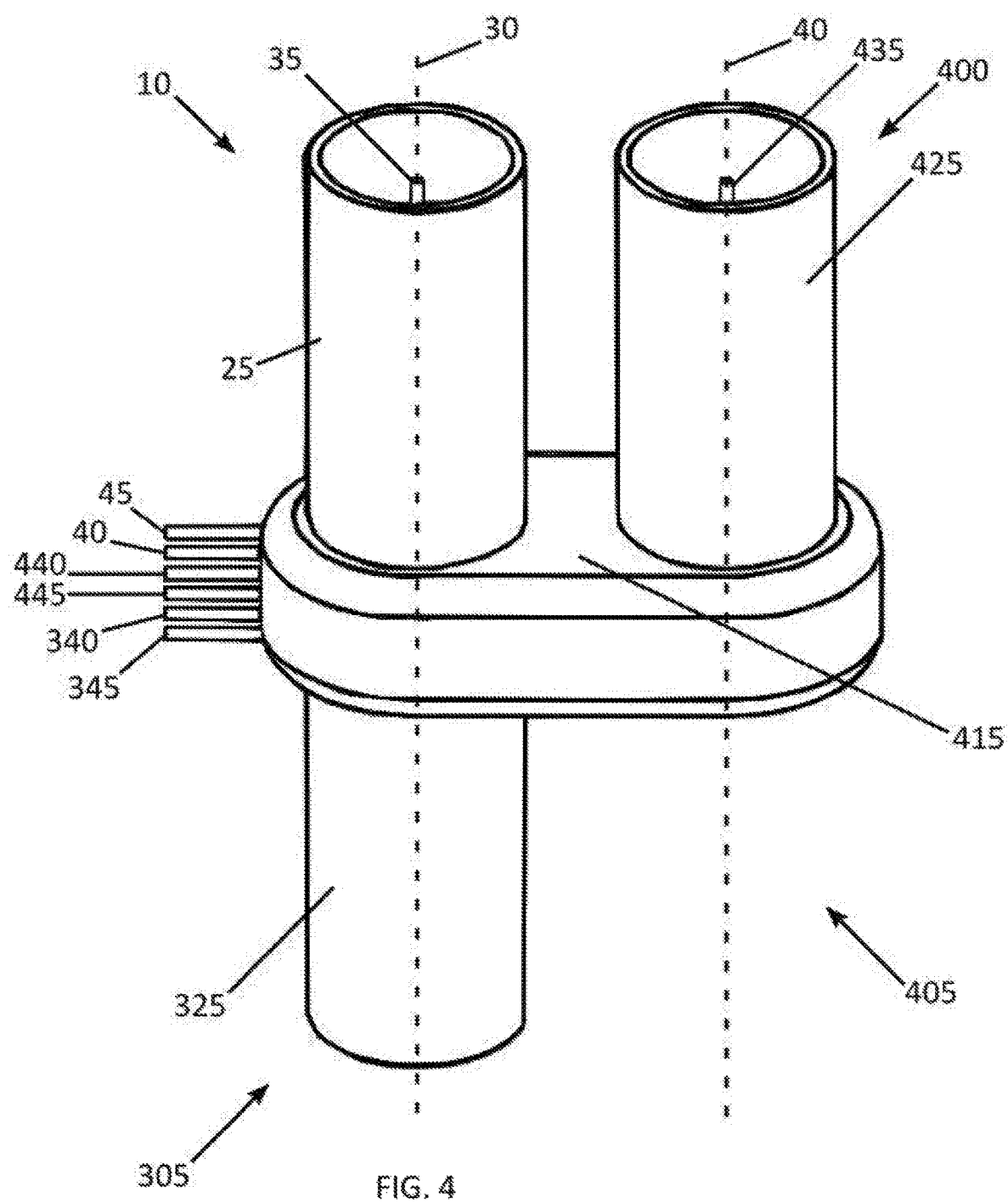
FIG. 4 depicts a triple axis impact switch according to one or more embodiments shown and described herein.

The double impact switch 300 may be used to provide another determination if a force threshold of was exceeded in a certain direction, as with the embodiment where the first threshold of the impact switch 10 is about equal to the second force threshold of the second switch 305. In another embodiment, the first threshold of the impact switch 10 may be greater than the second force threshold of the second switch 305 and may be used to determine the magnitude of the force applied to the double impact switch 300. In other words, if the second force threshold was exceeded but not the first force threshold, it may be determined that the force applied to the double impact switch 300 was between the G rating of the impact switch 10 and the G rating of the second switch 305. In another example, if the first threshold was exceeded, the second threshold was also exceeded. This may serve to provide a redundant indication that the first force threshold indication is correct. This may aid in a stepped indication of the force applied to the double impact switch 300 to determine the likelihood of a head and/or vertebral column injury. The double impact switch 300 is shown in FIG. 3 in an over-under configuration. In other embodiments, the impact switch 10 may be in a side-by-side configuration such as illustrated in FIG. 4 with the impact switch 10 and the third switch 400. In another embodiment, the second switch 305 may not be coaxially aligned with the impact switch 10. The double hub 315 may support the second switch 305 in any orientation to indicate the second force threshold in a second direction. For example, the second impact switch 305 may have a second switch axis (not shown but coaxially aligned with the second conductive member 335, the second switch axis may be orthogonal to the central axis 30. In yet another embodiment the second axis may be at an angle to the central axis 30.

FIG. 4 illustrates a triple impact switch 405. The impact switch 10 and the second switch 305 are coaxially aligned as explained above. A third switch 400 is co-located with the impact switch 10 and the second switch 305 on a triple hub 415. The third switch 400 is oriented in the same direction as the impact switch 10. In other words, the conductive member 35 and the third conductive member 435 are oriented in the same direction as well as the conductive body 25 and third conductive body 425 such that the central axis 30 is substantially parallel to a third axis 410. This allows for a force exerted on the triple impact switch 405 to affect the impact switch 10, second switch 305, and the third switch 400 identically, although each switch may have different force thresholds due to the conductive member 35, second conductive member 335, and the third conductive member 435 having different structure characteristics, composition, or differing body circumferences (example body circumference 60 of FIGS. 1A and 1B.) of their respective conductive bodies (i.e., conductive body 25, second conductive body 325, third conductive body 425). As explained above, in the embodiment for with differing force thresholds for each switch (impact switch 10, second switch 305, and the third switch 400), each force threshold may allow for a more accurate determination of the magnitude of the force measured in Gs exerted on the triple impact switch 405.

The impact switch 10, the second switch 305 and third switch 400 may share the triple hub 415. The triple hub 415 may include the hub base 20, the second hub base 320, and a third hub base (not shown). The triple hub 415 may include all the properties of the hub 15 described above to include that it is non-conductive and may serve as a conduit for the first wire 40, the second wire 45, the third wire 340, the fourth wire 345, a fifth wire 440, and a sixth wire 445 to pass through it. Referring to the third switch 400, the fifth wire 440 may be disposed through the triple hub 415 and may be configured to electrically couple with the third conductive body 425. The fifth wire 440 may also be disposed through the triple hub 415 and may be electrically coupled to the third conductive member 435. The third conductive member 435 may be coupled to the third hub base (not shown but identical in function to the hub base 20 of FIGS. 1A and 1B and structured to matedly couple with the third conductive body 425) and may be coaxially aligned with the third conductive member 435. The third conductive member 435 may also have a different structure characteristic and composition so that the third conductive member 435 of the third switch 400 has a different force threshold, or third force threshold, from the force threshold, or first force threshold, of the impact switch 10 and from the force threshold, or second force threshold, of the second switch 305. In another embodiment, the third force threshold may be about equal to the first force threshold and the second force threshold. In all embodiments, the discussion above concerning the conductive member 35 applies to the third conductive member 435.

The third conductive body 425 may have a third cap 450. The third cap 450 may be used to prevent the intrusion of dust and other contaminants between the third conductive member 435 and the third conductive body 425. The third cap 450 may also be color coded to indicate the force threshold the second switch 305 is configured to determine. The third cap 450 may be conductive or non-conductive. For example, in one embodiment, the third conductive member 435 may be configured to contact the third cap 450. In this embodiment, the third cap 450 is made from conductive material and the third cap 450 is electrically coupled to the third conductive body 425. In another embodiment, the third conductive member 435 may not be configured to contact the third cap 450. In this embodiment, the third cap 450 may not be made from conductive material and the third cap 450 may be coupled to the third conductive body 425 may not be required to be an electrical coupling. The third cap 450 may be coupled to the third conductive body 425 through an adhesive, crimping, welding, soldering, sealant material, rivet, screw, nail, shrink fitting, an interference fit, threades coupling, or male and female taper fitting.

In another embodiment, the third cap 450 is conductive and covers the distal end of third conductive body 425, where the proximal end of the third conductive body 425 is coupled to the triple hub 415. The distal end may include a slanted edge. This slanted edge allows for the triple impact switch 405 to indicate more than one force threshold. For example, upon impact, the third conductive member 435 will transition to a closed-circuit state upon contacting the third conductive body 425 on one side where the impact force was induced. The resiliency of the third conductive member 435 may be under damped. Therefore, upon returning towards the third axis 410, the third conductive member 435 may also electrically contact the slanted edge of third cap 450 in an opposite direction and thus transition to a closed-circuit state again and indicate a second, lesser force threshold from the third switch 400.

In yet another embodiment instead of the slanted edge, the second conductive body 325 may include one or more flat inner wall sections. The flat inner wall sections may allow for the double impact switch 300 to indicate more than one force threshold. The second conductive member 335 will transition to a close-circuit state upon contacting the second conductive body 325 on one side where a force was induced to the double impact switch 300. The resiliency of the second conductive member 335 may be under damped. Therefore, upon returning towards the second switch axis, the second conductive member 335 may also electrically contact the flat inner wall of second conductive body 325 in an opposite direction and thus transition to a closed-circuit state again and indicate a second, lesser force threshold.

The size of the impact switch 10, second switch 305, and the third switch 400 may be from about 0.5 mm×0.5 mm to about 20 mm×20 mm. In one embodiment, the size of the impact switch 10, second switch 305, and the third switch 400 may be from about 4.0 mm×4.0 mm. The size of the switch may allow for coupling of the switch closer to a head of a user to determine the force exerted on the head more accurately. The minimal size may also allow for more switches to be positioned around the head without discomfort or irritation. In one embodiment, impact switches with lower force thresholds may be positioned on a user to detect motion to force sensitive areas of the body which may lead to a head and/or vertebral column injury or other trauma. Further, impact switches with larger force thresholds may be positioned on a user to detect motion to stronger areas of the body in which a larger force is needed to lead to a head and/or vertebral column injury or create trauma to the body of the user.

In another embodiment, the triple impact switch 405 may not be oriented in the same direction as the impact switch 10. The triple hub 415 may support the third switch 400 in any orientation to indicate the third force threshold in a third direction. For example, the third axis 410 may be orthogonal to the central axis 30. In yet another embodiment the third axis 410 may be at an angle to the central axis 30.

The impact switch 10, the double impact switch 300, the triple impact switch 405 are non-limiting examples of the difference configurations the impact switch may take. The impact switch may include as many as five conductive members and conductive bodies, each with their own force threshold. For example, an impact awareness device (IAD) (FIG. 6A below), and, in the example of an impact protection apparatus IPA) may include the impact switch configured to determined when a force is exerted on the IAD in a first direction; a second switch with a second force threshold coupled to the headliner and configured to determine when a second force is exerted on the IAD in a second direction; a third switch with a third force threshold coupled to the headliner and configured to determine when a force is exerted on the IAD in a third direction; a fourth switch with a fourth force threshold coupled to the headliner and configured to determine when a force is exerted on the IAD in a fourth direction; and a fifth switch with a fifth force threshold coupled to the headliner and configured to determine when a fifth force is exerted on the IAD. For example, the first direction, the second direction, and third direction may all be a same direction and the indicator circuit may include a first three light emitting diode (LED), a second LED, and a third LED. The indicator circuit may illuminate and indicate the magnitude of the impact force along the same direction by illuminating the first LED if the force threshold is exceeded, illuminating the second LED if the second force threshold is exceeded, and illuminating the third LED if the third force threshold is exceeded.

In another embodiment, there may be a daisy chain of impact switches defining a closed shape. The daisy chain would allow the impact direction to be defined in a 360 degree plane. Multiple daisy chains may be coupled at specific angles to each other to get a three dimensional magnitude and vector of an impact.

Sealant may be used to cover the impact switch 10, the double impact switch 300, the triple impact switch 405, and any other embodiments of the impact switch to create a watertight, dustproof seal around the impact switch. The one or more wires (first wire 40, second wire 45, etc) may penetrate the sealant to electrically couple the impact switch to other electronics.

Figure 5:
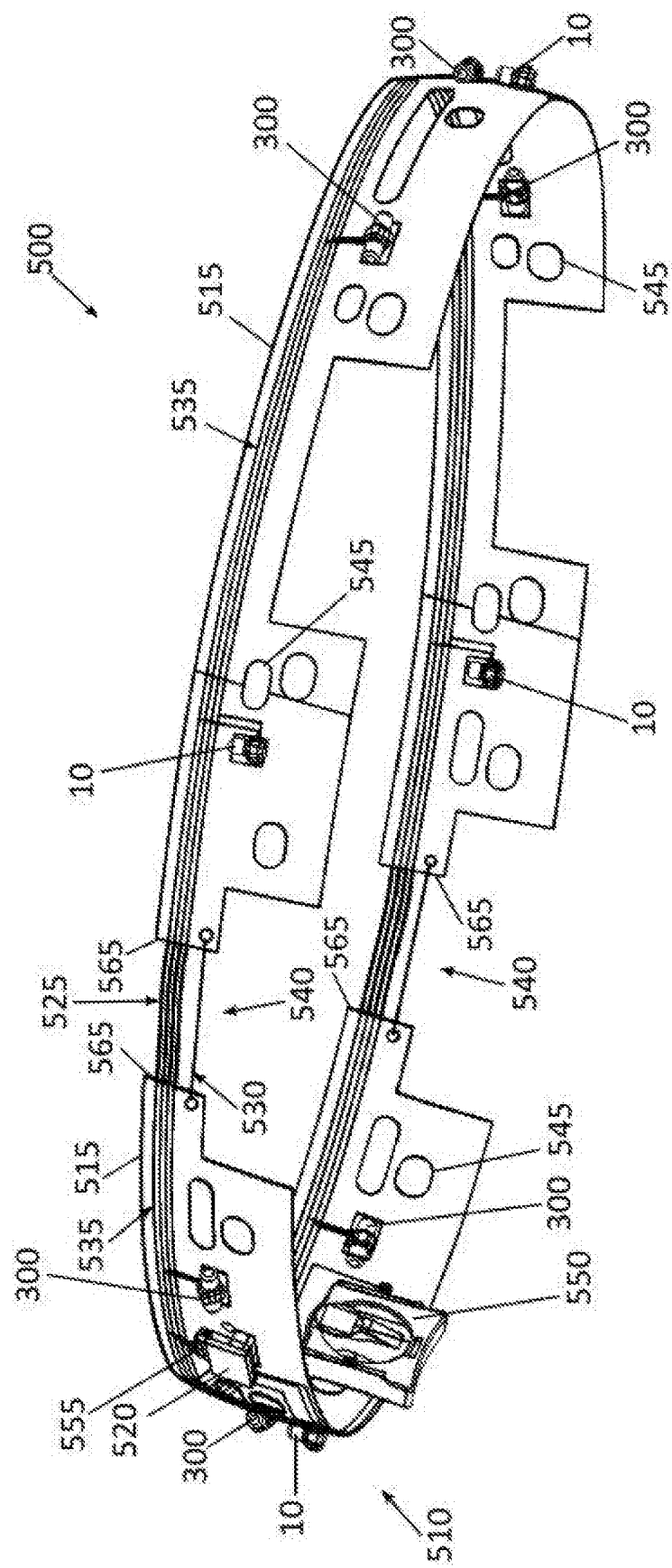
FIG. 5 depicts a headliner according to one or more embodiments shown and described herein.
Figure 6A:
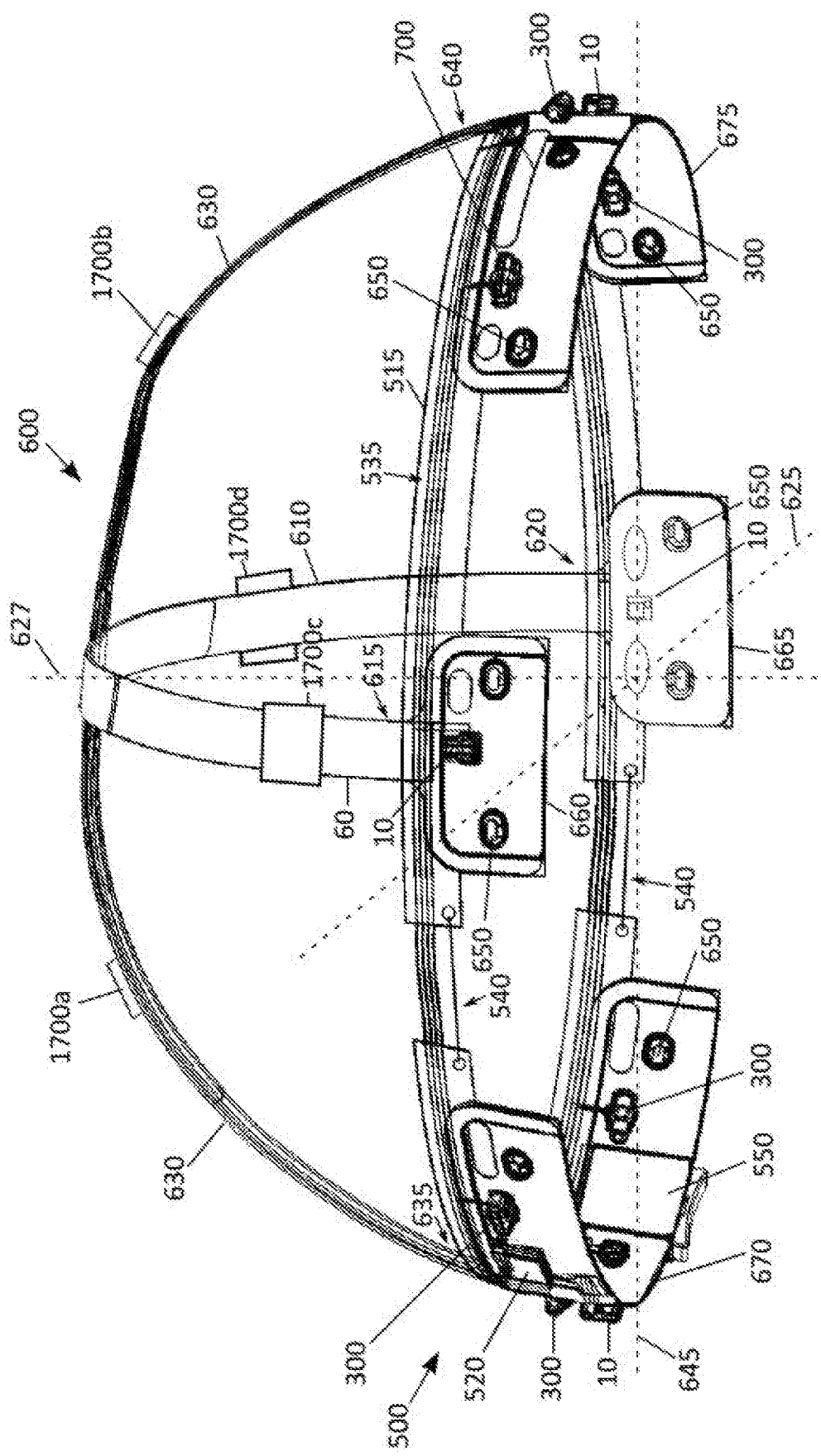
FIG. 6A depicts a headliner with one or more resilient ribs according to one or more embodiments shown and described herein.
Figure 6B:
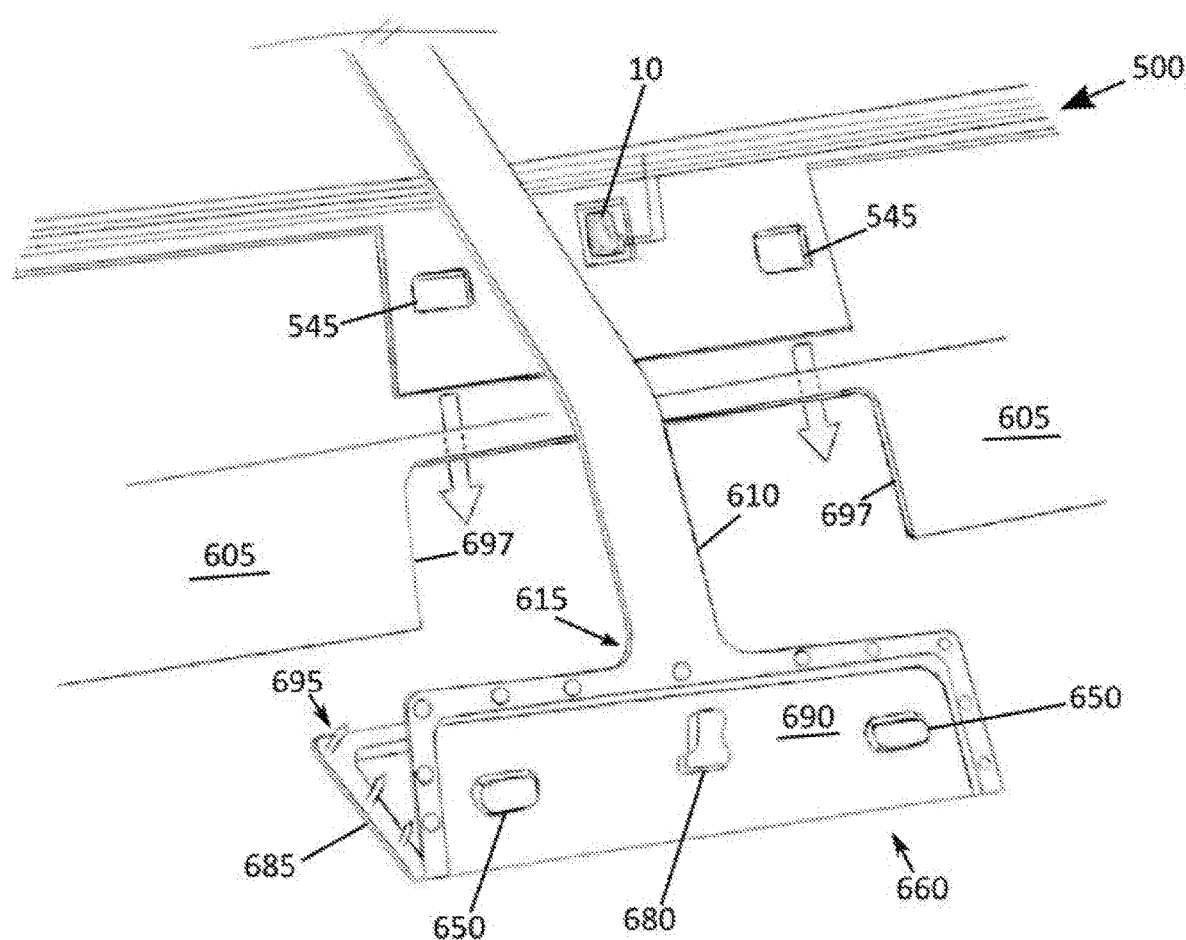
FIG. 6B depicts a connector of the headliner according to one or more embodiments shown and described herein.
Figure 7A:
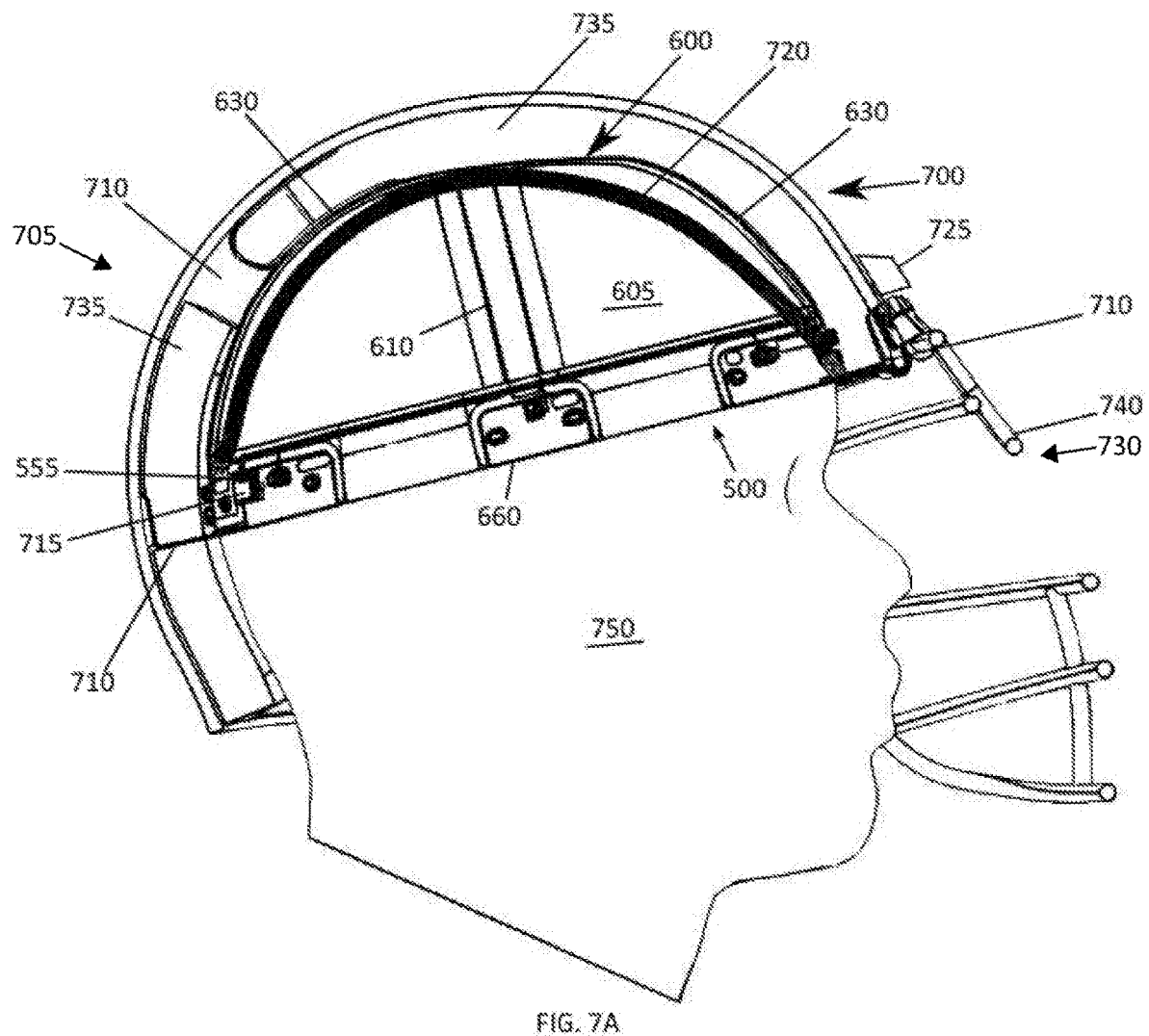
FIG. 7A depicts an impact awareness device according to one or more embodiments shown and described herein.

Referring generally to FIGS. 5 through 7, with specific numerical reference to FIG. 6A, the IAD may be used to removably couple with a protective headgear 700 of FIG. 7A. The IAD may be configured to sense the magnitude (G-force) of an impact, direction of the impact, and determine the likelihood of a concussion or trauma to a user. The IAD is configured to sense the impact in three-dimensions, X, Y, and Z. The X dimension is indicated by the first rib axis 625, the Y dimension by the second rib axis 645, and the Z dimension by the third rib axis 627.

Referring to FIG. 5, a headliner 500 is shown. The headliner 500 may include a flexible band 510, an electronic circuit 520, one or more conductors 535, one or more bridge conductors 525, and a power supply 550. The flexible band 510 may include one or more substrates 515, one or more expansion joints 540, one or more joint control devices 530, and one or more band apertures 545. The flexible band 510 may be configured to conform to either a head of a user or alternatively to a headband which may be removably coupled with a protective headgear 700 of FIG. 7A. The one or more substrates 515 may be made from a flexible plastic, cloth, elastic fabric, silicone, or the like. The one or more substrates 515 are arranged to end-to-end (565) and along with the one or more expansion joints 540, create a closed-shape. The one or more substrates 515 provide a mounting surface for other components of the headliner 500. For example, the electronic circuit 520, the one or more conductors 535, the one or more bridge conductors 525, and the power supply 550 are coupled to the one or more substrates 515 of the flexible band 510.

The flexible band 510 also includes one or more expansion joints 540 and one or more joint control devices 530. The one or more expansion joints 540 may allow for the adjustment of the flexible band 510 to conform to either a user's head or a headband of the protective headgear. The one or more expansion joints 540 may either be an open space between the one or more substrates 515 or the one or more expansion joints 540 may be an elastic material coupled between the one or more substrates 515. If the one or more expansion joints 540 are an elastic material, the one or more joint control devices 530 may not be needed. In one embodiment, the one or more joint control devices 530 is configured to maintain a maximum fixed distance between the ends of the one or more substrates 515. For example, and as shown in FIG. 5, the one or more joint control devices 530 may be a tether. The tether may be a string, tube, wire, strip of material, or other non-elastic material coupled between the ends 565 of the one or more substrates 515 and configured to maintain the maximum fixed distance. In this embodiment, the maximum fixed distance is determined by the one or more bridge conductors 525. The tether may be needed where the one or more substrates 515 is made from a cloth or elastic material and the one or more conductors 535 and/or the one or more bridge conductors 525 may be damaged by excessive stretching of the one or more expansion joints 540.

In another embodiment, the one or more joint control devices 530 is configured to impart a biasing force between the one or more substrates 515 and is coupled between the one or more substrates 515. The biasing force may be imparted to draw, or pull the ends 565 of the one or more substrates 515 together. This may allow the 510 to have a friction fit with a user's head. The one or more joint control devices 530 may be a clip spring, a compression spring, a tension spring, a torsion spring, a flat spring, or a wire-formed spring, all made from spring steel or the like. The biasing force may be needed where the one or more substrates 515 is made from a rigid material such as plastic or the like. In yet another embodiment, the one or more joint control devices 530 may be a manually adjustable device. The manually adjustable device may include a hook and loop fastener, a belt and buckle, a strap and buckle adjustable clips, a snapback device, or the like. In yet another embodiment, the one or more expansion joints 540 may not be needed and the one or more substrates 515 are a single substrate in a closed-shape configuration. In yet another embodiment, the one or more substrates 515 may be made from an elastic material and the one or more expansion joints 540 may be sewn with a series of overlapping folds that expand and contract to conform to a user's head.

It yet another embodiment, the one or more joint control devices may include a clip spring, a compression spring, a tension spring, a torsion spring, a flat spring, or a wire-formed spring as described above in combination with the tether. This embodiment may allow for flexing of the one or more expansion joints 540 and the tether will maintain the maximum fixed distance as described above.

The one or more substrates 515 may include one or more band apertures 545. The one or more band apertures 545 may be used to secure the headliner 500 to a surface or structure such as, for example, a headband of a protective headgear. The one or more substrates 515 may also have one or more impact switches (the impact switch 10 of FIGS. 1A and 1B, double impact switch 300 of FIG. 3, triple impact switch 405 of FIG. 4, and/or other variants of the impact switch 10 as described above) mounted to it. As shown in FIG. 5, 10 six double impact switches 300 are secured to the one or more substrates 515. Further, two impact switches 10 are secured to the one or more substrates 515. The location and orientation of the impact switches 10 and the double impact switches 300 are described in greater detail below.

The headliner 500 may also include the electronic circuit 520. The electronic circuit 520 is electrically coupled to the impact switches located on the headliner 500. The electronic circuit 520 makes the determination of the likelihood of a head and/or vertebral column injury or trauma when one or more of the impact switches transition from an open-circuit state to a closed circuit state. If the determination is made, an indicator signal and/or a trigger signal may be transmitted by the electronic circuit 520. The indicator signal and the trigger signal are described in greater detail below. In some embodiments, the electronic circuit 520 may not transmit both signals. For example, the electronic circuit 520 may send the trigger signal and not the indicator signal.

In one embodiment, the electronic circuit 520 may include a controller, a computer readable medium, and software executed by a processor. In another embodiment, the electronic circuit 520 may be an application specific integrated circuit (ASIC) that is designed and programmed to execute a program. In both embodiments, the electronic circuit 520 may include input/output ports and an electrical connector 555. The electrical connector 555 may be electrically coupled to the electronic circuit 520, may be used to electrically couple external components to the electronic circuit 520 or to signally couple an external personal computer or other computing device to download impact recordings or to upload updated software.

The power supply 550 may provide power for the electronic circuit 520 and the one or more impact switches (the impact switch 10 of FIGS. 1A and 1B, double impact switch 300 of FIG. 3, triple impact switch 405 of FIG. 4, and/or other variants of the impact switch 10 as described above). The power supply may be one or more battery cells or one or more capacitors. The one or more conductors 535 electrically connect the electronic circuit 520, the one or more impact switches, and the power supply 550 together. The one or more bridge conductors 525 are configured to span the one or more expansion joints 540 and are electrically coupled to the one or more conductors 535. The one or more bridge conductors 525 and the one or more conductors 535 may be a ribbon cable, one or more insulated wires, an optical fiber, or other electrically conductive materials.

The electronic circuit 520 and the power supply 550 are not limited to be positioned in the headliner 500. The electronic circuit 520 and the power supply 550 may be positioned anywhere to include the torso mount 830 (FIG. 8), in a headgear housing external to the protective headgear 700 (FIG. 7), a substrate sewn within a jersey of a user, a substrate adhered to an internal lining of the protective headgear 700, or a belt housing secured to a belt of the user.

Referring now to FIG. 6A, the headliner 500 is shown with one or more resilient ribs 600. The one or more resilient ribs 600 include a first rib 610 with a first rib end 615 and a second rib end 620 and defining a first rib axis 625. The first rib end 615 is coupled to the headliner 500 with a first connector 660 and the second rib end 620 is coupled to the headliner 500 with a second connector 665. The first connector 660 is opposite the second connector 665 on the headliner 500. A second rib 630 with a third rib end 635 and a fourth rib end 640 define a second rib axis 645, the third rib end 635 is coupled to the headliner 500 with a third connector 670 and the fourth rib end 640 is coupled to the headliner 500 with a fourth connector 675, the third connector 670 is opposite the fourth connector 675 on the headliner 500. The first rib axis 625 is perpendicular to the second rib axis 645. The first connector 660, the second connector 665, the third connector 670, and the fourth connector 675 are configured to removably couple the headliner 500 to the protective headgear 700 of FIG. 7A.

Referring to FIG. 6B, the second connector 665 is shown coupled to the first rib 610 at the first rib end 615. The second connector 665 has a first side 690 and a second side 685, the first side 690 is hingedly coupled to the second side 685. One or more fastening devices 695 may be used to secure the first side 690 to the second side 685. In one embodiment, the one or more fastening devices 695 are configured to penetrate and secure a fabric edge 697 of a fabric liner 605 and the one or more snaps are configured to matedly couple with the one or more band apertures 545 of the one or more substrates 515 of the headliner 500. In another embodiment, the one or more fastening devices 695 may be a hook fastener and the fabric edge 697 may be a loop fastener and the one or more snaps are configured to matedly couple with the one or more band apertures 545 of the one or more substrates 515 of the headliner 500. The fabric liner 605 may be coupled to the first rib 610 and the second rib 630 and provide for a barrier between a user's head and first rib 610, the second rib 630, and headliner 500.

The first connector 660, the second connector 665, the third connector 670, and the fourth connector 675 may include one or more protective enclosures 680 for protecting the components of the headliner 500. For example, the protective enclosure 680 of FIG. 6B would cover or encapsulate the impact switch 10 of the headliner 500 when the headliner 500 is inserted into the second connector 665 and the first side 690 is coupled to the second side 685 to secure the headliner 500. Not shown is a protective enclosure 680 on the second side 685 to cover or encapsulate the impact switch 10 when the first side 690 and the second side 685 are coupled together. It should be understood the discussion of the second connector 665 is representative of the first connector 660, the third connector 670, and the fourth connector 675 as well.

Referring back to FIG. 6A, impact switches 10 and the double impact switches 300 are oriented in such a manner so that in combination, they will react to sudden motion events occurring in X, Y, and Z coordinates/directions. As described above, each impact switch transitions to a closed-circuit state when the impact is applied to the impact switch as substantially orthogonally, and in a 360 degree arc around the central axis 30. Multiple switches, in combination, allow for the X, Y, and Z reactions to impacts, whether they are sudden motion events or occur of a period of time. For example, the four impact switches 10 are configured to detect the rotational movement of the IAD around the third rib axis 627. The six double impact switches 300 are configured to detect the rotational movement of the IAD around the first rib axis 625 and the second rib axis 645.

One or more ultrasonic devices 1700*a*, 1700*b*, 1700*c*, and 1700*d* may be used to measure and/or detect the movement of the brain of a user relative to the skull during athletic events or occupational hazards. The one or more ultrasonic devices 1700*a*, 1700*b*, 1700*c*, and 1700*d* in conjunction with the electronic circuit 520 may also measure and/or detect the movement or other subcutaneous tissues and/or organs relative to other tissues and/or organs in their proximity. The electronic circuit 520 may provide an indication through the indication signal if the movement of the brain relative to the skull reaches and/or exceeds a motion threshold. The one or more ultrasonic devices 1700*a*, 1700*b*, 1700*c*, and 1700*d* in conjunction with the electronic circuit 520 may use ultrasound technology which may be associated with sonography and/or Doppler shift monitors. The one or more ultrasonic devices 1700*a*, 1700*b*, 1700*c*, and 1700*d* in conjunction with the electronic circuit 520 may take real-time readings for momentary or temporary display or store the readings as data for later review on a computer readable medium. When activated by a trigger signal, described in greater detail below, a reading will be received by the electronic circuit 520 to indicate whether there was any tissue movement and/or how much tissue movement and the indication signal indicative of the reading will be transmitted.

In one embodiment, ultrasonic device 1700*c* and 1700*d* may be position at about the temple of the user's head. The trigger signal from the electronic circuit 520 may ultrasonic device 1700*c* and receive an ultrasonic signal from 1700*d*. The ultrasonic signal may be indicative of the shift of tissue within the skull. The electronic circuit 520 may use a look up table to compare to the ultrasonic signal to determine that amount of shift of the tissue or brain that occurred as a result of the impact. In another embodiment, the electronic circuit

520 may measure an amount of dopler shift between an ultrasonic wave transmitted by the ultrasonic device 1700c and the ultrasonic signal from the ultrasonic device 1700d.

One or more ultrasonic devices 1700a, 1700b, 1700c, and 1700d may be coupled to the resilient ribs (first rib 610 and the second rib 630) and configured to detect a shift in the user's brain. The one or more ultrasonic devices 1700a, 1700b, 1700c, and 1700d may work in pairs, one as a transmitter and one as a receiver. For example, 1700a may transmit an ultrasonic frequency through the user's head and 1700b may receive that signal. The one or more ultrasonic devices 1700a, 1700b, 1700c, and 1700d may be electrically coupled to the electronic circuit 520 through the one or more conductors 535 and one or more bridge conductors 525. The positioning of the one or more ultrasonic devices 1700a, 1700b, 1700c, and 1700d may be such that an shift in the brain of the user is easily detected, such as for example, located at the temples of a user. In another embodiment, the position of the one or more ultrasonic devices 1700a, 1700b, 1700c, and 1700d may be where shown in FIG. 6A. In yet another embodiment, the one or more ultrasonic devices 1700a, 1700b, 1700c, and 1700d may need to be in contact with the user's scalp or skin. If the one or more ultrasonic devices 1700a, 1700b, 1700c, and 1700d are in contact with the user's scalp or skin, a thin layer of silicone or other material which allows comfortable yet effective contact where necessary on the user may be used to also insulate and/or cushion the one or more ultrasonic devices 1700a, 1700b, 1700c, and 1700d from the user's scalp or skin. In another embodiment, the one or more ultrasonic devices 1700 may be coupled to the protective headgear 700 of FIG. 7A.

The one or more ultrasonic devices 1700a, 1700b, 1700c, and 1700d may operate in a continuous mode where the one or more ultrasonic devices 1700a, 1700b, 1700c, and 1700d are constantly transmitting and receiving ultrasonic signals. In another embodiment, the one or more ultrasonic devices 1700a, 1700b, 1700c, and 1700d may operate in a burst mode where the trigger signal from the electronic circuit 520 as described above would cause the one or more ultrasonic devices 1700a, 1700b, 1700c, and 1700d to transmit and receive the ultrasonic signal for a fixed duration of time. The fix duration of time may be about 1 second. In another embodiment, the fix duration of time may be about 5 seconds or more.

The one or more ultrasonic devices 1700a, 1700b, 1700c, and 1700d may be electrically coupled to the electronic circuit 520. The software in the electronic circuit 520 may dictate which situations burst mode versus continuous mode is used. For example, when the power supply 550 starts to run low on energy, the electronic circuit 520 may switch from the continuous mode to the burst mode. In one embodiment, the electronic circuit 520 is located in the headliner 500. In another embodiment, the electronic circuit 520 and power supply 550 may be located in a torso mount on the user. One or more wires may electrically couple the electronic circuit 520 and the power supply 550 to the one or more ultrasonic devices 1700a, 1700b, 1700c, and 1700d.

The electronic circuit 520 may detect the shift of the brain using the one or more ultrasonic devices 1700a, 1700b, 1700c, and 1700d and indicate Mild Traumatic Brain Injury (M.T.B.I.) a concussion or other trauma to the brain through an indicator circuit 725 from FIG. 7A described below, through progressive incidence detection, or visually on a small screen (not shown) indicating a number which represents the amount of shift which has occurred or other visual or audible indicator including graphic images of the brain in motion. The number would be indicative of the amount of motion which may suggest M.T.B.I. has occurred. The electronic circuit 520 may also use a wireless device to transmit the ultrasonically gathered information to a receiver. The electronic circuit 520 may also transmit a series of successive indicating information and/or images detected by the one or more ultrasonic devices 1700a, 1700b, 1700c, and 1700d of the brain and to another display and or receiver so the brain can be monitored. The receiver may be a smartphone, PC or base unit. The electronic circuit 520 may also record the images to a computer readable medium to provide information pertaining to the number of impacts, which impact switch indicated a force threshold was reached, and other brain shift information. A wired connection port may be configured to allow the computer-readable medium to be access and the recording to be read. The wired connection port may be coupled to the indicator circuit 725. In another embodiment, the electrical connector 555 of FIG. 5 may serve as the wired connection port.

Referring now to FIG. 7A, an IAD 705 is shown. The IAD 705 may include the headliner 500, one or more resilient ribs 600, and the indicator circuit 725. In another embodiment, the IAD may include only the headliner 500. In FIG. 7A, the headliner 500 is shown surround a head 750 of a user with the first rib 610, the second rib 630 spanning over the top of the head 750. The orientation of the headliner 500 is shown with the second connector 665 on the side of the head 750. The protective headgear 700 is worn by the user and in this embodiment, the headliner 500 with one or more resilient ribs 600 is coupled to the protective headgear 700 by one or more attachment points 710. The one or more attachment points 710 may be a piece of fabric, coupled to the one or more resilient ribs 600 and looped through the protective padding 735 of the protective headgear 700 to secure the headliner 500 to the protective headgear 700. In another embodiment, the one or more attachment points 710 may be a hard plastic and secured to the protective headgear by fastening devices. Fastening devices include, but are not limited to, screws, buttons, snap buttons, bolts, rivets, nails, adhesives, Velcro (hook and loop fastener, weld, epoxy, or any similar device that mechanically joins or affixes two or more objects together. In yet another embodiment, the one or more attachment points 710 may be fastening devices that couple the headliner 500 to the protective headgear 700.

Figure 7B:
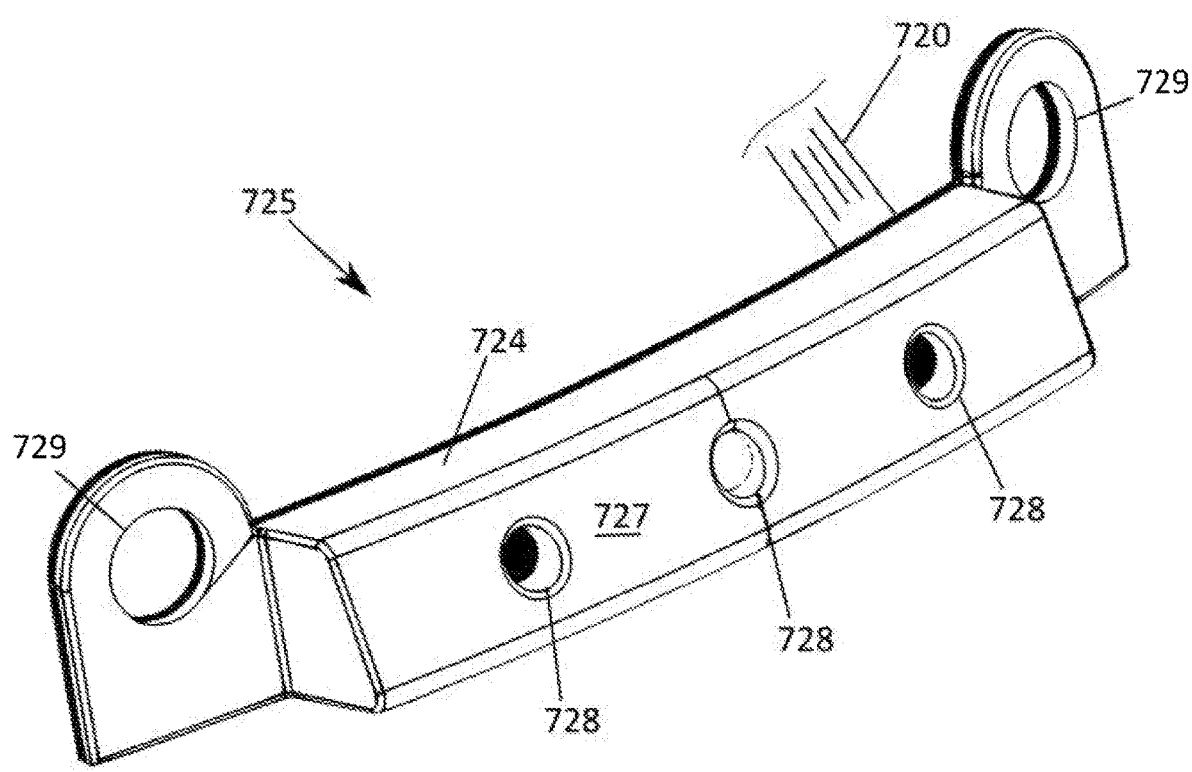
FIG. 7B, depicts an indicator according to one or more embodiments shown and described herein.
Figure 7C:
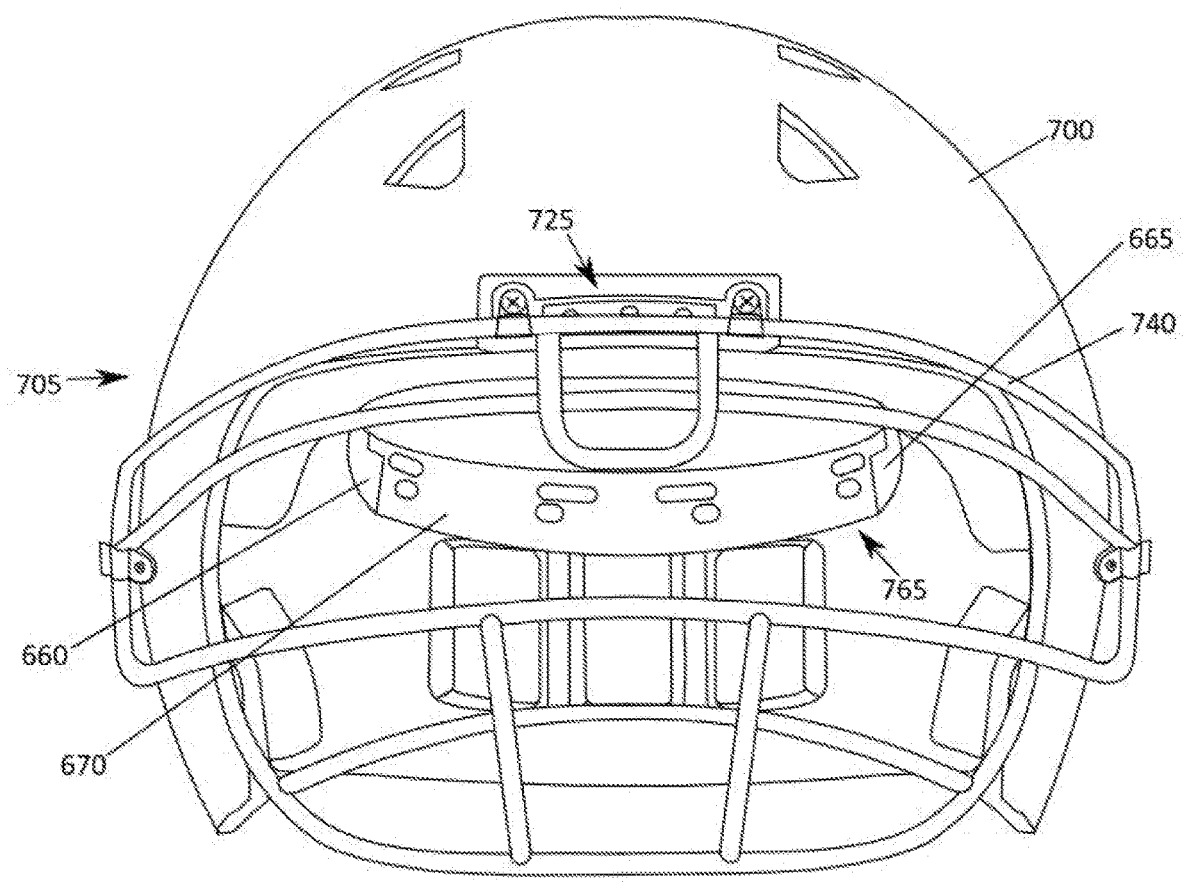
FIG. 7C depicts a protective headgear with the IAD and indicator circuit according to one or more embodiments shown and described herein.

Referring to FIGS. 7A, 7B, 7C the indicator circuit 725 may be coupled to the protective headgear 700 and be electrically coupled to the electronic circuit 520. The electronic circuit 520 is electrically coupled to the indicator circuit 725 through a communication cable 720. The communication cable 720 electrically couples with the electronic circuit 520 through the electrical connector 555. The communication cable 720 may allow the indicator signal to be as simple as a pulse to illuminate a Light Emitting diode (LED) or complex phase and/or frequency modulated signals to carry image data from the one or more ultrasonic devices 1700. The indicator circuit 725 may be configured to provide an indication of the likelihood of an impact related injury when the indicator signal is received from the electronic circuit 520. The indication may be an audible, a visible, a tactile, or a pallesthesia indication. Pallesthesia is defined as the ability to sense a vibration. Examples of visible indication may include a data readout display, a liquid crystal display (LCD), an electroluminescent light, one or more Light Emitting diodes (LEDs) (single and/or multi-colored and/or phosphor-based LEDs), organic light emitting diodes (OLEDs), quantum dot LEDs, Nixie tubes, light strips, fluorescent light, incandescent light bulbs or combinations thereof.

In another embodiment, the indicator circuit 725 may be a wireless device configured to wirelessly transmit the indicator signal to a receiver. Wireless protocols such as IEEE 802.11, 802.11a, 802.11b, 802.11g, or 802.11n may be used to signally communicate the indication signal or other protocols which may become available. As used throughout, the indication signal may be as simple as a pulse to tell the indicator circuit 725 to provide visual or auditory indications. The indication signal may be a signal that includes information pertaining to brain shift, number and magnitude of impacts, and cumulative information of impacts while the IAD 705 is powered. In another embodiment, the wireless device may be configured to both send and receive wireless signals to and from other IADs 705 and/or to a central base unit. This embodiment may allow for a remote user to also be informed and/or alerted of another user's sudden motion event and/or information. The alerting information may include sudden motion event indicating codes, such as but not limited to pulses of light images or vibrations, and/or digital and/or numeric representations for a given sudden motion event. Such information may also be secured via digital encryption.

Referring to FIG. 7B, the indicator circuit 725 is shown. The indicator circuit 725 may include one more display mount apertures 729 to secure the indicator circuit 725 to a surface or structure. The indicator circuit 725 may include a display face 727. The display face 727 may include the one or more LEDs 728 as shown in FIG. 7B. In another embodiment, indicator circuit 725 may include the audible device such as a piezo buzzer, speaker with associated circuitry to project an audible instruction or warning, or a mechanical clacker. The display face 727 may couple with a dust cover of the audible device. In yet another embodiment, the indicator circuit 725 may include a display and the display face 727 may include a screen of the display. The display may scroll messages across it, display error codes, impact codes, graphical illustrates of the impact, or flash to alert an operator of the potential for the likelihood of a head and/or vertebral column injury or trauma.

Referring now to FIG. 7C, a front view of the protective headgear 700 with the IAD 705 and indicator circuit 725. The indicator circuit 725 may be mounted on the protective headgear 700 or an applicable object such as shoulder pads or chest piece. The indicator circuit 725 may be mounted where it is protected from impacts. In another embodiment, the indicator circuit 725 may be housed within a protective housing 724 of FIG. 7B. As shown in FIGS. 7A and 7C, the indicator circuit 725 may be mounted slightly lower than an outer surface 730 of a faceguard 740 of the protective headgear 700 so the indicator circuit 725 is protected from impacts with other helmets or objects. The indicator circuit 725 may be coupled to the protective headgear 700 by fastening devices.

The IAD 705 may include an on-off switch. The on-off switch may be manually operated and located on the protective headgear 700. The on-off switch may be a simple toggle switch that allows a user to turn on and turn off the IAD 705. In another embodiment, the IAD 705 may include a power switch 765 located within the protective headgear 700 and configured to turn on the IAD 705 when a user places their head within the protective headgear 700. The IAD 705 may turn off when the user removes the protective headgear 700 from their head. In another embodiment, the power switch 765 may be located within a torso mount 830 of FIG. 8 and turn-on the IAD 705 when the user wears the torso mount 830. The IAD 705 may turn-off when the user removes the torso mount 830. In yet another embodiment, the IAD 705 may be remotely activated or deactivated by a third user. In all embodiments, the power switch may be a toggle switch, a pressure switch, a proximity switch, a lever switch, a rocker switch, or the like.

Referring generally to FIGS. 8 through 17, with specific numerical reference to FIGS. 8A and 8B, the IAD 705 may include structures for the immobilization of and/or protection from impact forces to the user's head during a potentially injurious impact event while wearing the protective headgear 700. The immobilization device has two states; an active state and an inactive state. In the inactive state, the user's head will be normally in a state of free articulation and the structures connecting the protective headgear 700 headgear to a torso mount 830 will allow for passive articulation of the user's head without restriction. In the active state, the protective headgear 700 may become immobilized and temporarily unified with the structure of the torso mount 830, thereby providing a protective impact force absorbing barrier between the object causing the impact and the user's head. The user's head may be immobilized via the structures connecting the protective headgear 700 to the torso mount 830. When the structures are activated, the protective headgear 700 is frozen in the head's current position at about the moment of impact. The structures will not move the head/spine into alignment. The active state may be initiated via a detected event such as, for example, an impact and a trigger signal is sent to the structures from the electronic circuit 520 as described above. The duration of the active state is depended on the duration of the detected event. For example, the head may be immobilized (activated) for the duration of a motor vehicle accident and immediately mobilized (deactivated) upon the cessation of the accident.

The structures may be activated by electric switches, such as but not limited to the impact switch described above, accelerometers, and inertial switches, located about or upon the user which are triggered by impacts and/or sudden accelerations or decelerations or other detected events upon the user or the headgear.

Referring now to FIGS. 8A and 8B, a headgear immobilization device 800 is shown. The headgear immobilization device 800 includes a mounting base 810, a mounting bracket 815, one or more linear locks 825, and a quick release lever 820. The one or more linear locks 825 couple the protective headgear 700 to the torso mount 830. The torso mount 830 may be a shoulder pad, shoulder harness, chest pad, back pad, and or other wearable apparatus which will allow for appropriate mounting. A binding immobilizer 1001 may be coupled to the torso mount 830 and be configured to help restrain the body of the user during an impact and while receiving the trigger signal from the electronic circuit 520 of FIG. 5. The binding immobilizer 1001 is discussed in greater detail below.

FIGS. 9A and 9B show the mounting base 810 and the mounting bracket 815. The mounting base 810 may be coupled to the protective headgear 700 through fastening devices 805, the fastening devices are described above. The mounting base 810 includes one or more mount slots 850 and one or more slots 835. The mounting bracket 815 includes one or more pegs 840 and one or more mount plates 865 which may include one or more mount teeth 855. The pegs 840 are coupled to the mounting bracket 815 on the backside 870. The one or more mount plates 865 are coupled to the mounting bracket 815 on the frontside 875. Individual ones of the one or more linear locks 825 are coupled to the upper universal joint 845 which is coupled to individual one or more mount plates 865. One or more torso plates 860 may be used to couple the one or more linear locks 825 to the torso mount 830 of FIG. 8A. The torso plate 860 may include a lower universal joint 880 coupled between each linear lock 825 and each torso plate 860.

The mounting bracket 815 matedly couples with the mounting base 810. The mounting bracket 815 unifies the one or more linear lock 825 for ease in coupling with the mounting base 810. The mounting bracket 815 may also include a biasing mechanism 827 to bias the mounting bracket 815 away from the protective headgear 700 when the mounting bracket 815 and the mounting base 810 are not coupled together. The one or more pegs 840 aid in aligning the mounting bracket 815 with the one or more slots 835 on the mounting base 810. The quick release lever 820 is actuated to release the mounting bracket 815 from the mounting base 810. The combination of the mounting base 810 and the mounting bracket 815 may allow a user to put their protective headgear 700 on, tilt their head back, and feel for the one or more pegs 840 slip into the one or more slots 835 and lock the quick release lever 820 on one or both sides of the mounting bracket 815. In another embodiment, the quick release lever 820 may also include a snap, clasps, spring clip, and the like.

In another embodiment, the mounting base 810 may couple to a lower rim 885 of the protective headgear 700 and the one or more torso plates 860 may couple to a vertical surface 890 (FIG. 8B) of the torso mount 830. In this embodiment, the one or more mount teeth 855 may not be needed. This configuration allows for the one or more linear locks 825 to lie substantially along the vertical surface 890 and may reduce the restriction of articulation of the user's head. This configuration may also allow for minimal to no contact between each linear lock of the one or more linear locks 825 to through the full articulated range of the headgear immobilization device 800.

The one or more upper universal joints 845 and the one or more lower universal joints 880 allow a user to move their head in the state of free articulation. The one or more upper universal joints 845 may include a first joint end 891 and a second joint end 892 and one or more lower universal joints with a third joint end 893 and a fourth joint end 894, the one or more upper universal joints 845 and the one or more lower universal joints 880 are configured to allow a free range of movement between the protective headgear 700 and the torso mount 830. The first joint end 891 is coupled to the second mount end 925, the second joint end 892 is coupled to the mounting bracket 815, the third joint end 893 is coupled to the second rod end 945, and the fourth joint end 894 is coupled to the torso mount 830. The one or more upper universal joints 845 and the one or more lower universal joints 880 may be a ball joint, a hinge and socket joint, a pivot joint, a saddle joint, a hinge joint, a cradle joint, a conyloid joint, or combinations thereof.

Referring to FIGS. 10A through 10E, multiple embodiments of the one or more linear locks 825 are shown. FIGS. 10A and 10B illustrate a square embodiment of the linear lock 825 and FIGS. 10C and 10D illustrate a round embodiment of the linear lock 825. The round embodiment includes one or more guides 975 and one or more guide grooves 980 to keep a rod slide 960 in alignment. The rod slide 960 is explained further below.

Referring to FIG. 10E, each linear lock of the one or more linear locks 825 includes a lock housing 900 with a first lock end 910 and a second lock end 905. A mount 915 includes a first mount end 920 and a second mount end 925. The first mount end 920 may be coupled to the first lock end 910 and second mount end 925 may be coupled to the mounting bracket 815. A rod 935 includes a first rod end 940 and a second rod end 945. A plurality of substantially parallel grooves 955 are disposed along the rod 935 between the first rod end 940 and the second rod end 945. The first rod end 940 travels through a housing aperture 950 at the second lock end 905, and the second rod end 945 is coupled to a torso mount 830 as shown in FIG. 8A. An interrupter mechanism 1000 may be disposed within a platform 965. The platform 965 may be disposed within the lock housing 900 and slideably couples with the rod 935. The interrupter mechanism 1000 is configured to restrict the travel of the rod 935 by engaging an individual groove of the plurality of substantially parallel grooves 955 when the trigger signal is received from the electronic circuit 520 of FIG. 5, thereby restricting the movement of the protective headgear 700 in relation to the torso mount 830.

A stop 930 may be coupled to the mount 915 and be used to restrict a total travel of the rod 935. A peg (not shown) may be coupled to the rod 935 and prevent the rod 935 from sliding out of the lock housing 900. The peg may slideably engage a slot aperture (not shown) on the mount 915. In another embodiment, the peg may slideably engage a slot aperture in the lock housing 900. The peg may include a push button release to quickly remove the peg and allow the rod 935 to be removed from the lock housing 900. If, for example, the quick release lever 820 should be damaged due to an impact, the push button release may still allow for the protective headgear 700 to be separated from the torso mount 830. The peg may be a small rod, a screw, a bolt, or other protrusion from the rod 925 that is configured to slideably coupled with the slot aperture. In another embodiment, the peg may be coupled to the lock housing 900 and the slot aperture may be coupled to the rod 935.

In the above embodiment, the rod 935 includes the plurality of substantially parallel grooves 955. In another embodiment, the rod 935 may be coupled to the rod slide 960. The rod slide 960 slideably couples with the platform 965 and includes the plurality of substantially parallel grooves 955. The rod slide 960 may aid in the alignment of the plurality of substantially parallel grooves 955 and the interrupter mechanism 1000.

FIGS. 11A, 11B, and 11C, illustrate a binding immobilizer 1001. The binding immobilizer 1001 is a device for the immobilizing of binding materials including but not limited to chords, straps, ropes and belts. The binding immobilizer 1001 may normally be unrestricted to allow a belt 1020 to extend or retract. When the binding immobilizer 1001 receives the trigger signal from the electronic circuit 520 of FIG. 5, the binding immobilizer 1001 may instantly brake to limit or stop any extension or retraction of the belt 1020 via the interrupter mechanism 1000 which may be an electromagnetically actuated latching mechanism. In one embodiment, the binding immobilizer 1001 may be used to help secure the torso mount 830 with the user at the moment of impact, allowing free movement of the user's body until it is activated, thereby stopping the further extension of the user's body and/or the torso mount 830 from the body. In another embodiment, the binding immobilizer 1001 may also be used the control the excessive motion of the user's head when attached to the protective headgear 700 and torso mount 830 by itself or in combination with (immobilizers, FIGS. 8A through 10E and FIGS. 12A through 18B) herein described as well as in contact sports, as part of climbing equipment, safety equipment for workers on high rises, construction workers, window washers, wind generator workers and as seatbelts for drivers and occupants of vehicles.

Referring to FIG. 11A, the binding immobilizer 1001 may include the belt 1020, a roller buckle 1005 coupled to the belt 1020 between a proximal end and a distal end, a buckle 1010 coupled to the belt 1020 at the proximal end, and a belt mount 1025 coupled to the belt 1020 at the distal end. The belt 1020 may not be elastic. The buckle 1010 and the roller buckle 1005 each have a first mount aperture 1007. The buckle 1010 and the roller buckle 1005 may be configured to matedly couple and secure the belt 1020 around or through the torso mount 830. In another embodiment, the first mount aperture 1007 may be used to secure the buckle 1010 to a first surface, structure, or device and the second mount aperture 1008 may be used to secure the roller buckle 1005 to a second surface, structure, or device.

FIG. 11B, illustrates a cross-sectional view of the binding immobilizer 1001. The stationary belt 1026 may be elastic. The belt 1020 may include a plurality of substantially parallel grooves 955. The roller buckle 1005 may include a roller 1015 that allows the belt 1020 to change a belt length 1033.

Referring to FIGS. 11B and 11C, the interrupter mechanism 1000 is disposed within a recess 1070. The interrupter mechanism 1000 may include one or more pawls 1040 and an actuator 1060. The actuator 1060 may be a solenoid, a electromagnet/magnet pair, or a spring under compression with a retaining device configured to release the spring when triggered. The actuator is configured to provide an upward force in the direction of B to move the one or more pawls 1040 in the direction of A. The one or more pawls 1040 are configured to removably engage a groove of the plurality of substantially parallel grooves 955 and rotate about a pivot point 1045. The one or more pawls 1040 are configured to engage the groove of the plurality of substantially parallel grooves 955 regardless of the direction of travel of the plurality of substantially parallel grooves 955. For example, in one embodiment with a single pawl 1040, the interrupter mechanism 1000 may engage the groove of the plurality of substantially parallel grooves 955 in only one direction. For example, in the embodiment shown, the one or more pawls 1040 may engage the groove of the plurality of substantially parallel grooves 955 is both linear directions and engage the same groove of the plurality of substantially parallel grooves 955. In the stopped position, the pawls are seated within a groove of the plurality of substantially parallel grooves 955. In the stopped position, the belt 1020 is restricted in its movement. In a free position, the pawls are seated in the recess 1070 and the belt 1020 is not restricted in its movement. The function of the interrupter mechanism is discussed in greater detail below.

In one embodiment, the belt mount 1025 may include a backer block 1030. The backer block 1030 may provide a surface for the one or more pawls 1040 to engage the belt 1020 in the stopped position and prevent the belt 1020 from slipping over the one or more pawls 1040. In another embodiment, the backer block 1030 is not needed and the belt mount 1025 may be configured to provide the surface for the one or more pawls 1040 to engage the belt 1020 in the stopped position and prevent the belt 1020 from slipping over the one or more pawls 1040.

FIGS. 12A through 12C illustrate the various embodiments of the interrupter mechanism 1000. The interrupter mechanism 1000 may further include the actuator 1060, the one or more pawls 1040, and on or more upper stops 1095. The actuator 1060 is configured to transition the one or more pawls 1040 from a stopped position to a free position. The free position is illustrated in FIG. 12A and the stopped position is illustrated in FIG. 12B. In one embodiment, the actuator 1060 may include an electromagnet 1085, the magnet 1080, a first trigger wire 1055 and a second trigger wire 1065. When the trigger signal is received through the first trigger wire 1055 and the second trigger wire 1065, the electromagnet 1085 may energize and magnetically exert a biasing force on the magnet 1080 in the direction of arrow B. The biasing force may be exerted through the same polarity sides of the magnet 1080 and the energized electromagnet 1085 are facing each other causing a repulsive force between the magnet 1080 and the electromagnet 1085. The magnet 1080 may slideably coupled with the one or more pawls 1040 and transition the one or more pawls 1040 from the free position to the stopped position. When the trigger signal is removed, the electromagnet may de-energize and the magnet 1080 may move opposite the direction of arrow B and transition the one or more pawls from the stopped position to the free position. The one or more pawls 1035 may include a biasing mechanism to induce a downward bias (opposite arrow B) to aid in the disengagement of the one or more pawls 1035 when the trigger signal is removed.

In yet another embodiment, the actuator 1060 may further include a spring 1090, a pin 1075, a guide sleeve 1050, and one or more pawl springs 1035. In this embodiment, the pin 1075 may be coupled to the spring 1090 and the one or more pawl springs 1035. The spring 1090 is further coupled to the magnet 1080 and may provide an additional biasing force in the direction of arrow B and aid the electromagnet 1085 biasing force, when energized, to transition the one or more pawls 1040 from the free position to the stopped position. The one or more pawl springs 1035 are coupled to the pin 1075 and configured to slideably couple with the one or more pawls 1040.

Referring now to FIG. 12C, the one or more pawls 1040 may include a first pawl 1041 and a second pawl 1042. When the belt 1020 of FIG. 11B or the rod 935 of FIG. 10E is traveling across the one or more pawls 1040 in the direction of arrow C, the second pawl 1042 will engage the groove of the plurality of substantially parallel grooves 955. Alternatively, when the belt 1020 of FIG. 11B or the rod 935 of FIG. 10E is traveling across the one or more pawls 1040 in the direction of arrow D, the first pawl 1041 will engage the groove of the plurality of substantially parallel grooves 955. The one or more pawl springs 1035 allow the first pawl 1041 to act independently of the second pawl 1042. In other words, if for example, the belt 1020 exerted a downward force on the first pawl 1041, the second pawl 1042 may not drop and miss engaging the groove of the plurality of substantially parallel grooves 955 because the pin 1075 was dropped due to the force exerted on it due the first pawl 1041.

Referring back to FIGS. 12A and 12B, the actuator 1060 is disposed within a recess 1070. The guide sleeve 1050 may be disposed within the recess 1070 and the actuator 1060 may be disposed within the guide sleeve 1050. The guide sleeve 1050 may keep the components of the actuator 1060 in alignment and may also prevent the magnet 1080 from tilting or flipping when the electromagnet 1085 is energized.

In yet another embodiment, and referring to FIGS. 12A and 12B, instead of the electromagnet, when energized, biasing the magnet 1080 in the direction of arrow B, the spring 1090 may provide the biasing force to the magnet 1080. In this embodiment, the interrupter mechanism 1000 may be in the stopped position when the electromagnet is de-energized. The trigger signal may instruct a controller to de-energize the electromagnet 1085. When the electromagnet is energized, it may provide an attraction force that overcomes the biasing force of the spring 1090 and transitions the interrupter mechanism to the free position.

In yet another embodiment, the belt 1020 of FIG. 11B or the rod 935 of FIG. 10E may not have the plurality of substantially parallel grooves 955 disposed on them. The one or more pawls 1040 may engage the belt 1020 or the rod 935 through friction.

In yet another embodiment, the lock housing 900 of FIG. 10E and the belt mount 1025 of FIG. 11C may include a protective lip to prevent material or a user's skin from entering the lock housing 900 or the belt mount 1025 during free movement of the linear lock 825 or the binding immobilizer 1001. The protective lip may slideably couple with the belt 1020. Furthermore, the lock housing 900 and the belt mount 1025 may be enclosed within a dust cover to prevent any particulate build-up within the lock housing 900 and the belt mount 1025.

Figure 13:
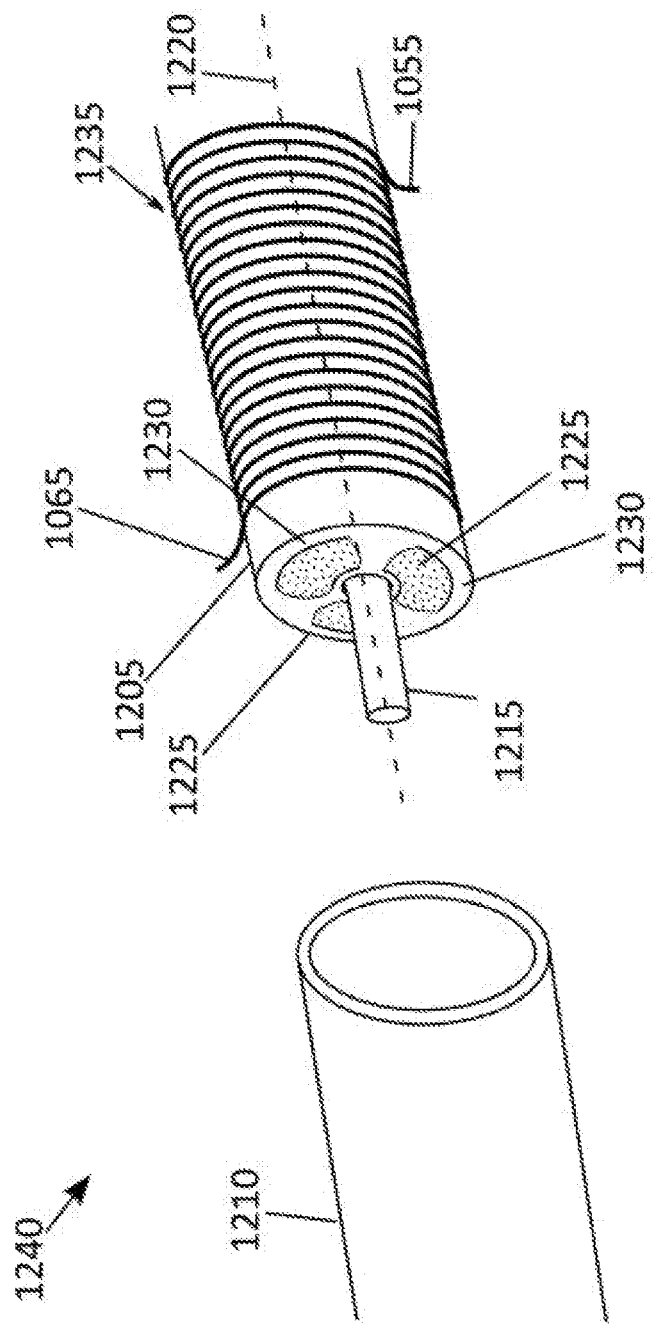
FIG. 13 depicts an exploded view of a flexible electromagnet assembly according to one or more embodiments shown and described herein.
Figure 16B:
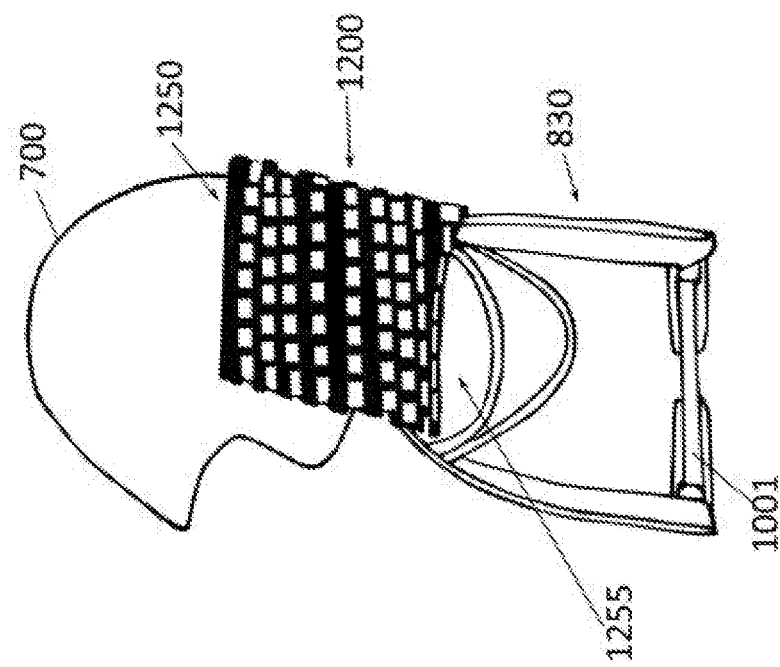
FIG. 16B depicts a right side view of the interlaced mat headgear immobilization device according to one or more embodiments shown and described herein.
Figure 16A:
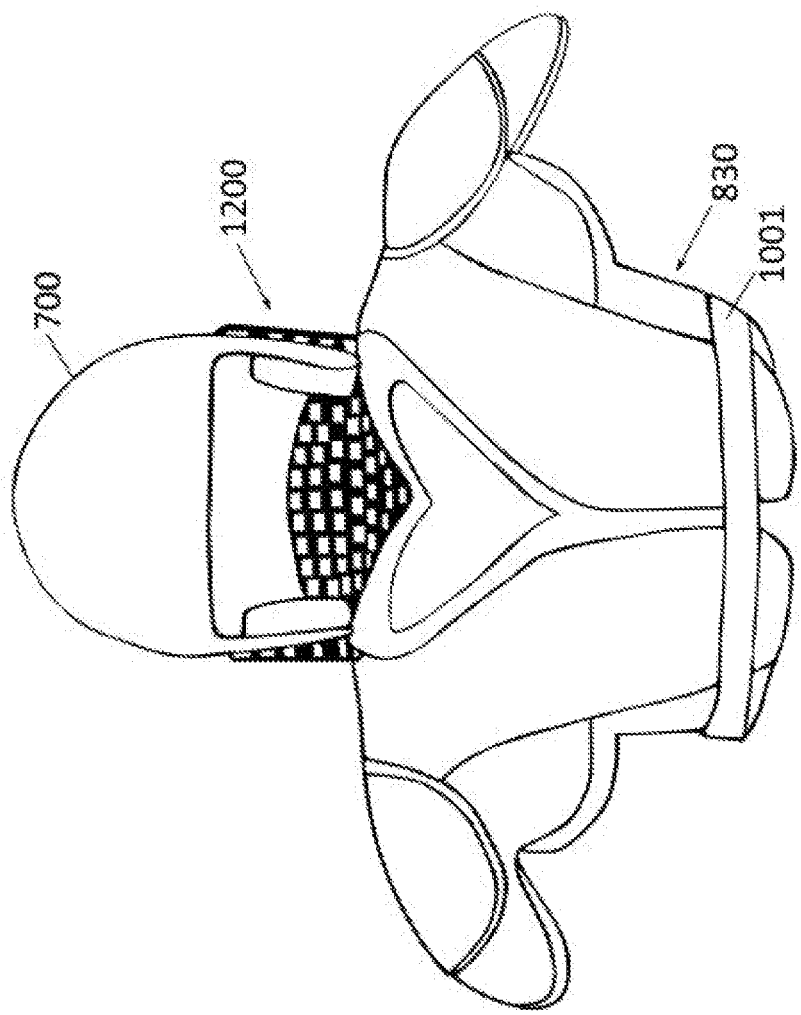
FIG. 16A depicts a front view of the interlaced mat headgear immobilization device according to one or more embodiments shown and described herein.
Figure 19:
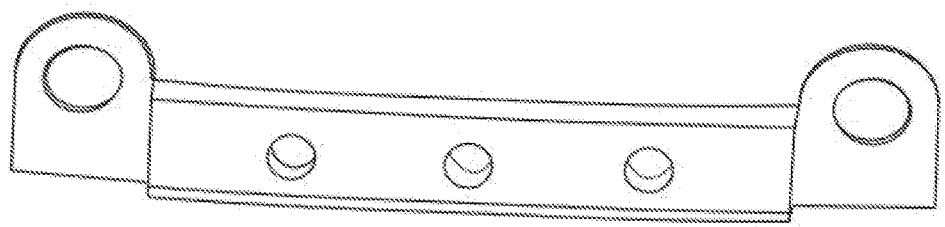
FIG. 19 depicts a front view of an indicator housing.
Figure 20:
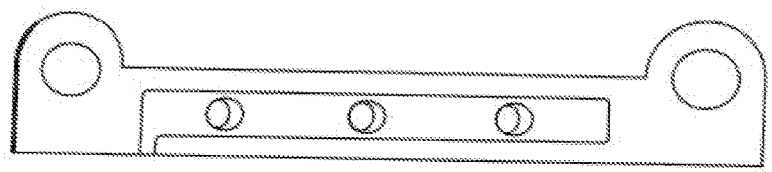
FIG. 20 depicts a rear view of the indicator housing.
Figure 21:
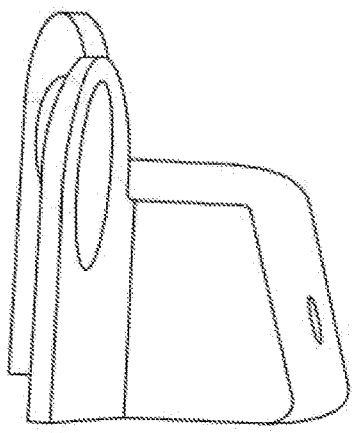
FIG. 21 depicts a right side view of the indicator housing.
Figure 22:
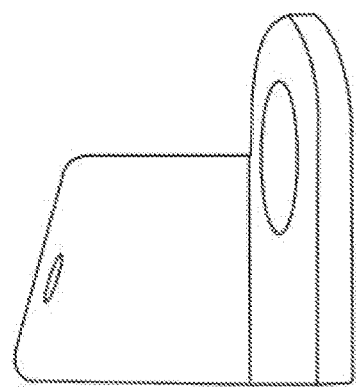
FIG. 22 depicts a left side view of the indicator housing.
Figure 23:
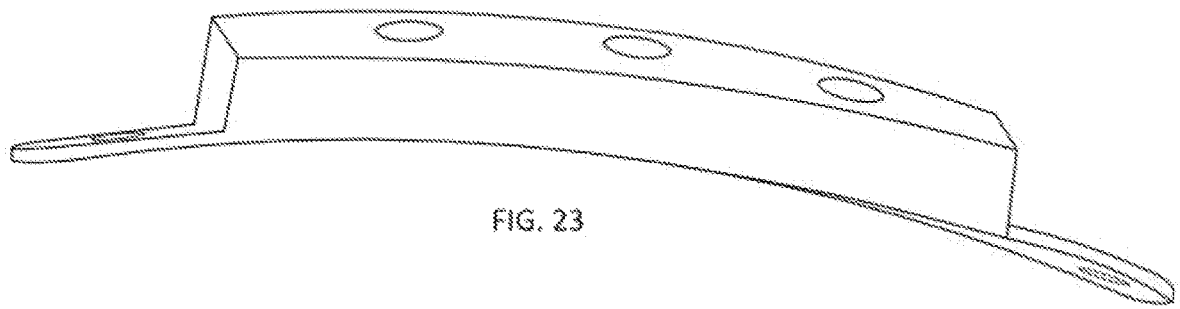
FIG. 23 depicts a top view of the indicator housing.
Figure 24:
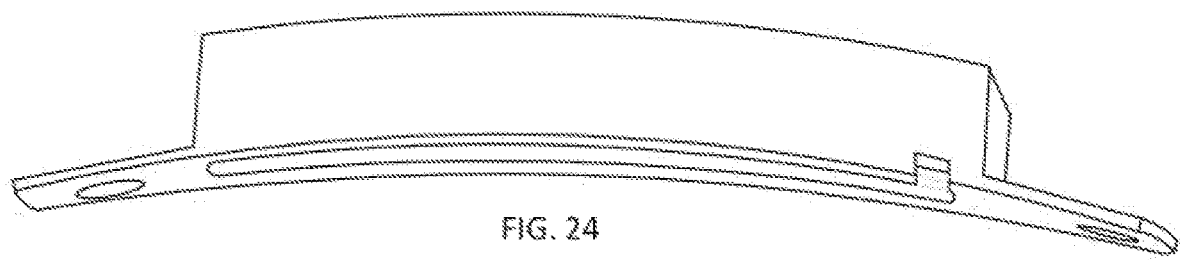
FIG. 24 depicts a bottom view of the indicator housing.
Figure 25:
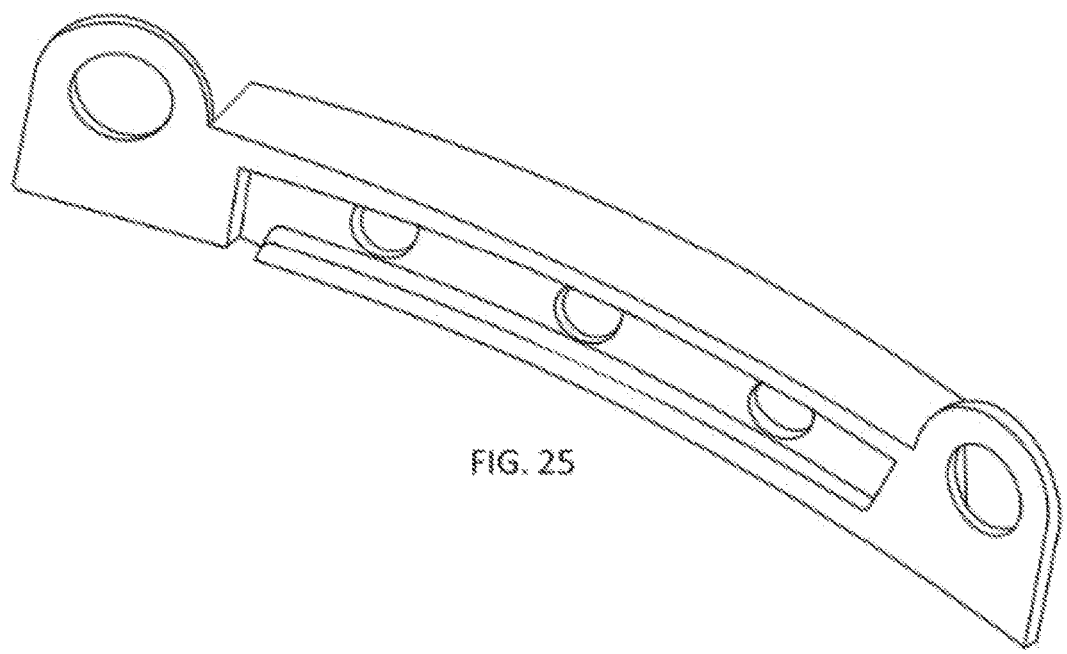
FIG. 25 depicts a rear, right, perspective view of the indicator housing.
Figure 26:
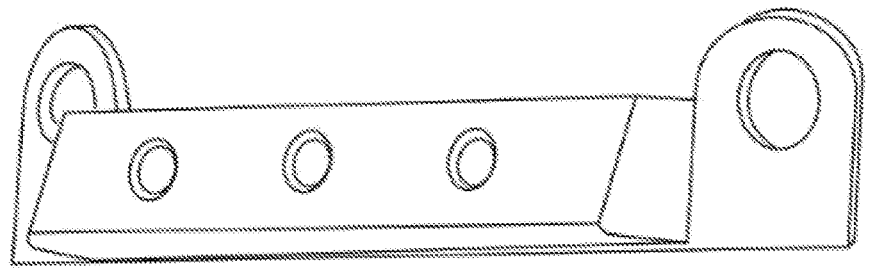
FIG. 26 depicts a front, left, perspective view of the indicator housing.

Referring generally to FIGS. 13 through 18B with specific numerical reference to FIG. 13, a flexible magnetorheological (MR) fluid assembly (i.e., a flexible electromagnet assembly 1240 of FIG. 13 and a stacked flexible electromagnet assembly 1565 of FIG. 14A) may be used to restrict the movement of the protective headgear 700 to the torso mount 830 of FIG. 16A. MR fluid 1225 is a type of smart fluid in a carrier fluid, usually a type of oil. When the MR fluid is subjected to a magnetic field, the fluid greatly increases its apparent viscosity, to the point of becoming a viscoelastic solid or a rigid member. The yield stress of the MR fluid 1225 when in its active ("on") state can be controlled very accurately by varying the magnetic field intensity. The MR fluid's ability to transmit force can be controlled with an electromagnet. In other words, the MR fluid 1225 may be configured to transition from a fluid state to a rigid state when a magnetic field is present. The MR fluid 1225 may be disposed with a protective tube 1210 and a magnetic wire 1235 may be wrapped around a flexible tube 1205. The magnetic wire 1235 may be electrically coupled to the electronic circuit 520 of FIG. 5 and may create a magnetic field to transition the MR fluid from a fluid to a rigid member when the trigger signal is received.

Referring to FIG. 13, the flexible electromagnet assembly 1240 is shown. Each flexible electromagnet assembly 1240 includes a protective tube 1210 with a flexible tube 1205 disposed within the protective tube 1210, the flexible tube 1205 has a ferromagnetic core 1215 along a tube axis 1220 of the flexible tube 1205 and a MR fluid 1225 disposed within the flexible tube 1205 and surrounding the ferromagnetic core 1215. A magnetic wire 1235 may be wrapped around the flexible tube 1205 and electrically coupled to the electronic circuit 520 of FIG. 5. The magnetic wire 1235 in combination with ferromagnetic core 1215 may create a magnetic field to transition the MR fluid from a fluid to a rigid member when the trigger signal is received.

The flexible electromagnet assembly 1240 may also include one or more longitudinal tubes 1230 disposed within the flexible tube 1205 and configured to enclose the MR fluid 1225. The one or more longitudinal tubes 1230 may provide another lay of protection against puncture and loss of MR fluid 1225 and may also keep the MR fluid even distributed around the ferromagnetic core 1215.

Referring to FIGS. 14A and 14B, the stacked flexible electromagnet assembly 1565 is shown. The stacked flexible electromagnet assembly 1565 may include one or more stacked flexible electromagnet assembly 1565, each stacked flexible electromagnet assembly 1565 may include one or more magnetic plugs 1515. The magnetic plugs include a flexible tube 1520 with a first tube end 1525 and a second tube end 1530 and a magnetic wire 1235 wrapped around the flexible tube 1520. The magnetic wire 1235 has a first plug wire 1570 and a second plug wire 1575. The one or more stacked flexible electromagnet assembly 1565 may also include one or more capture tubes 1535 with a first capture end 1545 and a second capture end 1550 wherein the first capture end 1545 is configured to matedly couple with the second tube end 1530 and the second capture end 1550 is configured to matedly couple with the first tube end 1525. The one or more stacked flexible electromagnet assembly 1565 may also include the MR fluid 1225 disposed within the one or more capture tubes 1535, wherein the one or more magnetic plugs 1515 and one or more capture tubes 1535 are coupled together to create each stacked flexible electromagnet assembly 1565. Each stacked flexible electromagnet assembly 1565 may include a first cap 1555 and a second cap 1560 configured to keep particulates and other material out of the stacked flexible electromagnet assembly 1565. Each stack 1556 may also be enclosed in a flexible sealant.

Referring now to FIG. 15, an interlaced mat 1251 is shown. The interlaced mat 1251 may include one or more flexible electromagnet assemblies 1240, one or more stacked flexible electromagnet assemblies 1565, or a combination thereof woven together and coupled between two moveable objects, such as for example, the protective headgear 700 and the torso mount 830 and shown below in FIGS. 16A and 16B. When the trigger signal is received from the electronic circuit 520 of FIG. 5, a current in the magnetic wire 1235 creates a magnetic field which aligns a plurality of particles in the MR fluid 1225 thereby making the interlaced mat 1251 rigid and restricting the movement of the protective headgear 700 in relation to the torso mount 830. When the electronic circuit 520 ceases to send the trigger signal, the plurality of particles in the MR fluid 1225 will relax thereby allowing a free range of movement between the protective headgear 700 and the torso mount 830. The combination of the one or more flexible electromagnet assemblies 1240 and one or more stacked flexible electromagnet assemblies 1565 is shown in FIG. 15. It should be understood that the interlaced mat 1251 may include only one or more flexible electromagnet assemblies 1240 or only one or more stacked flexible electromagnet assemblies 1565.

FIGS. 16A and 16B illustrate a magnetic headgear immobilization device 1200. The magnetic headgear immobilization device 1200 may be configured as the interlaced mat 1251, shown in FIG. 15, where the interlaced mat 1251 has a first mat end 1250 and a second mat end 1255. The first mat end 1250 is coupled to the protective headgear 700 and the second mat end 1255 is coupled to a torso mount 830. When the trigger signal is received from the electronic circuit 520 of FIG. 5, the magnetic headgear immobilization device 1200 restricts the movement of the protective headgear 700 in relation to the torso mount 830. In another embodiment, the first mat end 1250 may be coupled to the protective headgear 700 and the second mat end 1255 may be slideably coupled to a torso mount 830 or vice versus. In other words, the magnetic headgear immobilization device 1200 may be removably coupled to both the protective headgear 700 and the torso mount 830. The binding immobilizer 1001 may be coupled to the torso mount 830 and be configured to help restrain the body of the user during an impact and while receiving the trigger signal. The binding immobilizer 1001 is discussed in greater detail above.

Referring to FIG. 17, illustrates a stacked mat 1501. The stacked mat 1501 may include a first sheet 1580 and a second sheet 1585 positioned on the first sheet 1580, the one or more flexible electromagnet assemblies 1240, one or more stacked flexible electromagnet assemblies 1565, or a combination thereof, are disposed between the first sheet 1580 and the second sheet 1585 and are substantially parallel to each other to create the stacked mat 1501. The first sheet 1580 and the second sheet 1585 may enclose the one or more flexible electromagnet assemblies 1240, one or more stacked flexible electromagnet assemblies 1565, or a combination thereof and provide a protective barrier. In another embodiment, the first sheet 1580 and the second sheet 1585 may be a single sheet folded over.

The stacked mat 1501 has a first stacked mat end 1505 and a second stacked mat end 1510. Each flexible tube 1520 of the stacked flexible electromagnet assembly 1565 are electrically coupled in series. In other words and referring to FIG. 14A, the first plug wire 1570 of the flexible tube 1520 is electrically the second plug wire 1575 of the adjacent flexible tube 1520. The first stack wire 1512 and the second stack wire 1511 electrically couple the one or more magnetic wires 1235 of the one or more adjacent flexible tubes 1520 together and are electrically coupled to the electronic circuit 520 of FIG. 5.

Referring to FIGS. 18A and 18B, illustrates a vertically aligned magnetic headgear immobilization device 1500. The vertically aligned magnetic headgear immobilization device 1500 may include the stacked mat 1501 of FIG. 17 and include the first stacked mat end 1505 is coupled to the protective headgear 700 and the second stacked mat end 1510 is coupled to a torso mount 830. When the trigger signal is received from the electronic circuit 520 of FIG. 5, each stacked flexible electromagnet assembly 1565 becomes rigid and thereby the stacked mat 1501 becomes rigid and restricts the movement of the protective headgear 700 in relation to the torso mount 830. When the electronic circuit 520 ceases to send the trigger signal, the plurality of particles in the MR fluid will relax thereby allowing a free range of movement between the protective headgear 700 and the torso mount 830. The binding immobilizer 1001 may be coupled to the torso mount 830 and be configured to help restrain the body of the user during an impact while receiving the trigger signal. The binding immobilizer 1001 is discussed in greater detail above. In another embodiment, the first stacked mat end 1505 may be coupled to the protective headgear 700 and the second stacked mat end 1510 may be slideably coupled to a torso mount 830 or vice versus. In other words, the vertically aligned magnetic headgear immobilization device 1500 may be removably coupled to both the protective headgear 700 and the torso mount 830.

FIGS. 19 through 26 illustrate the ornamental views of an indicator for a protective headgear as shown and described.

When the IAD 705 is worn by a user, the headliner 500 will reside between the innermost surfaces of the protective headgear 700 and the outermost surface of a user's head. The headliner 500 also includes means for self-support and self-orientation through the one or more resilient ribs 600 when the headgear is worn by a user along with methods for adjusting its fit on a user's head. The headliner 500 may also be easily added to a variety of protective headgear 700 and allows for easy removal of the protective headgear 700 as well as the removal of the headliner 500 from the protective headgear 700 if necessary.

The impact switch 10 is configured to read the forces applied to the head of the user. The impact switch 10 is not limited to the headliner 500 (FIG. 5) and may be positioned on the protective headgear 700 (FIG. 7) or the torso mount 830 (FIG. 8), or one or more impact switches may be positioned in, on, or about either the protective headgear 700 or torso mount 830. When an impact is detected by one or more impact switches at various locations, the headgear immobilization device 800, the magnetic immobilizer headgear 1200 or the vertically aligned magnetic headgear immobilization device 1500 will lock the current position of the protective headgear 700 to the current position of the torso mount 830 and enable the impact force to be transferred through the protective headgear 700 to the torso mount 830 through either one or more linear locks 825, the interlaced mat 1251, or the stacked mat 1501. This will minimize the force of the impact applied to the head of the user. The binding immobilizer 1001 if FIGS. 8A and 8B may lock the torso mount 830 to the user and prevent any shifting or lifting of the torso mount 830 in response to the leverage applied to the protective headgear 700 during an impact.

In another embodiment, the impact switches and the immobilization devices may be used to protect the body of the user from an impact. For example, if a user receives an impact to the back, an impact switch 10 on the torso mount 830 may indicate the impact and the binding immobilizer and/or the headgear immobilization device 800 or magnetic immobilizer headgear (1200 or 1500) may lock to keep the torso mount 830 in place and protect the spine and/or neck. Alternatively, the magnetic immobilizer headgear 1200 or the vertically aligned magnetic headgear immobilization device 1500 may be positioned across the back of a user and when triggered, provide a stable surface to absorb the impact.

The headliner 500 is configured to fit the heads of humans as well as other animals. The headliner 500 may be of a fixed size or it may have means to adjust its fit as described above. The headliner 500 may be attached to, and become a part of the protective headgear 700 such as helmets and head protectors, whether hard or soft shelled. In another embodiment, the IAD 705 may be coupled to a headband for use in soccer, field hockey and the like.

Some applications all combined or as individual devices activated by the IAD switches of the IAD 705 may include, but are not limited to, American style football, hockey, baseball, Lacrosse, Olympic and professional boxing, motor vehicle racing, cycling, skateboarding, skydiving, water polo, rodeo horse and bull riding, horse jumping and racing, skiing, snowboarding, surfing, mountain climbing and pogo stick jumping. The IAD 705 may also be used for physically, mentally, or emotionally challenged/disabled person. The IAD 705 may also be used for military, rescue, police, pilots, factory, and construction worker applications.

It should be noted that different impact switches may apply to different purposes within the IAD System. The switches may be used to indicate forces which may cause head and/or vertebral column injury, they may be used to trigger/activate other devices for preventing injury, they may be used for collecting data, transmitting the data or activate devices intended for training users to avoid situations where injuries may occur to them or others, or combinations thereof.

The impact switch 10, double impact switch 300, the triple impact switch 405, the daisy chain of impact switches, and combinations thereof may be used in other applications independent of the IAD 705 to gather information about the levels of sudden motion or impacts. For example, on shoes, luggage, sports equipment, robots, tools and machinery, rockets, explosives testing, prosthetic limbs, vehicles related to vehicle impacts and centrifugal forces, packaging to indicate impact damage during shipping, electronic or other devices to indicate impact damage information or attitude/orientation information, vibration levels of machinery, artillery shells and other ordnance, medical equipment for humans and animals, physical training equipment for humans and animals, drop testing machinery and equipment, as well as other uses where sudden motion information are collected or users wish to be alerted about sudden motion events.

It should be noted that although there are specific references to the electronic circuit 520 in FIG. 5 and its location as mounted in the headliner 500, the electronic circuit 520 may be mounted anywhere on the protective headgear 700 or torso mount 830. Furthermore, the impact switch 10, and other variants thereof, may be a motion sensitive device, a motion sensor, an electrical switch, an accelerometer switch, an inertial switch. It should also be noted that all spring material may be made from spring steel.

Figure 27:
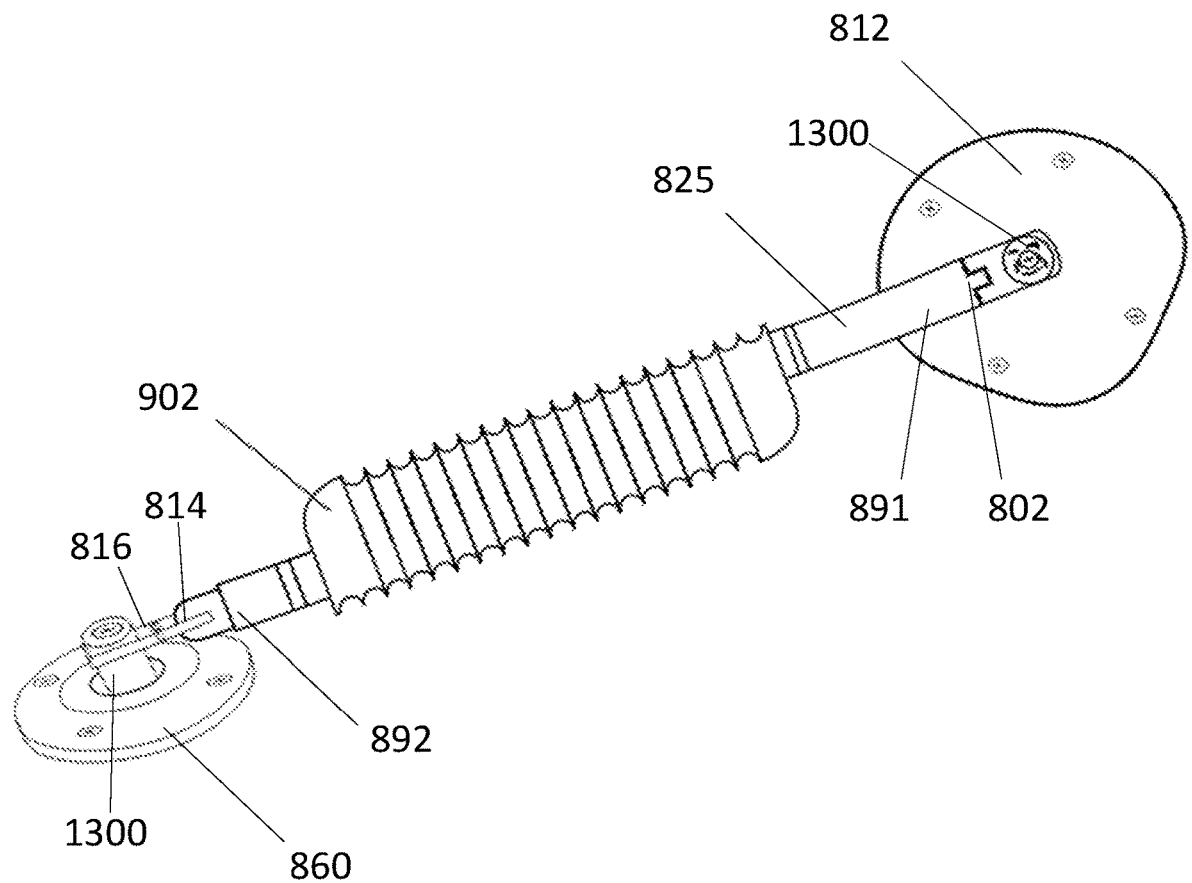
FIG. 27 depicts a perspective view of a linear lock according to one or more embodiments shown and described herein.
Figure 28:
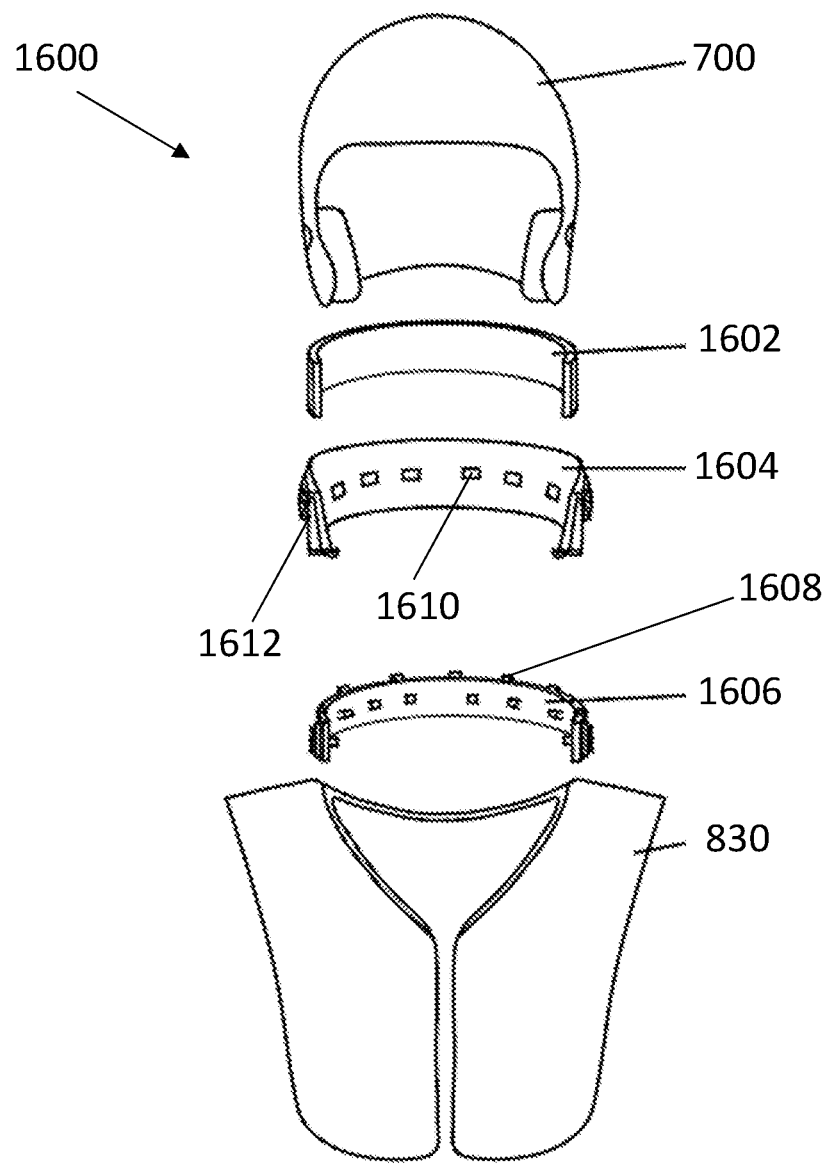
FIG. 28 depicts a front view of the headgear immobilization device according to one or more embodiments shown and described herein.
Figure 29:
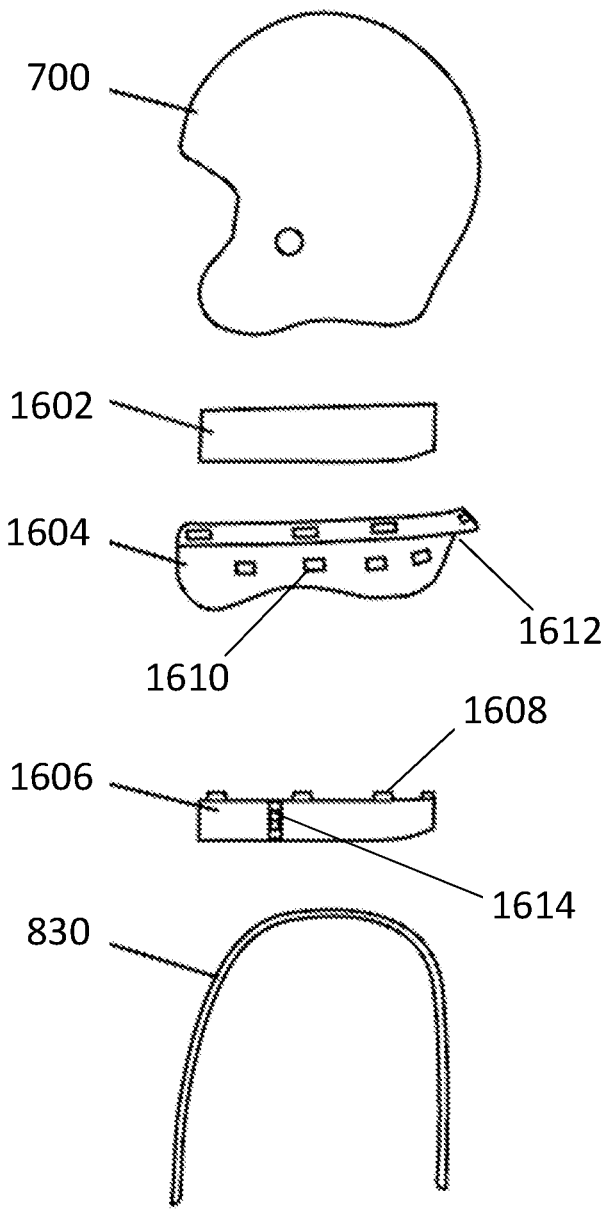
FIG. 29 depicts a left side view of the headgear immobilization device according to one or more embodiments shown and described herein.

Further improvements to the features of the IADs described hereinabove, as well as features of impact protection apparatuses (IPA), including the above-mentioned linear locks and related operational members, are described below. With reference to FIG. 27, the linear lock 825 and, if included, the lock housing 900 described above, can be protected from dirt and debris by a flexible protective boot 902. Flexible protective boot 902 can cover substantially all of the linear lock 825 up to one or both of the first joint end 891, and/or the second joint end 892, as described in more detail with respect to FIG. 9B, for example. Flexible protective boot 902 can be made of any flexible, durable material, including, for example, plastic, rubber, elastomeric materials, composite polymers, and the like. Flexible protective boot 902 can have a corrugated, accordion-like configuration to provide for flexible deformation under lateral as well as axial forces. The flexible protective boot 902 can substantially seal all or a portion of the movable portions of the linear lock 825 to protect from the entry of dirt and debris, as well as moisture from weather and sweat that might impede the proper operation of the linear lock 825. As well, the flexible protective boot 902 can provide protection of the linear lock 825 against impact forces as well as damage from handling.

Figure 30:
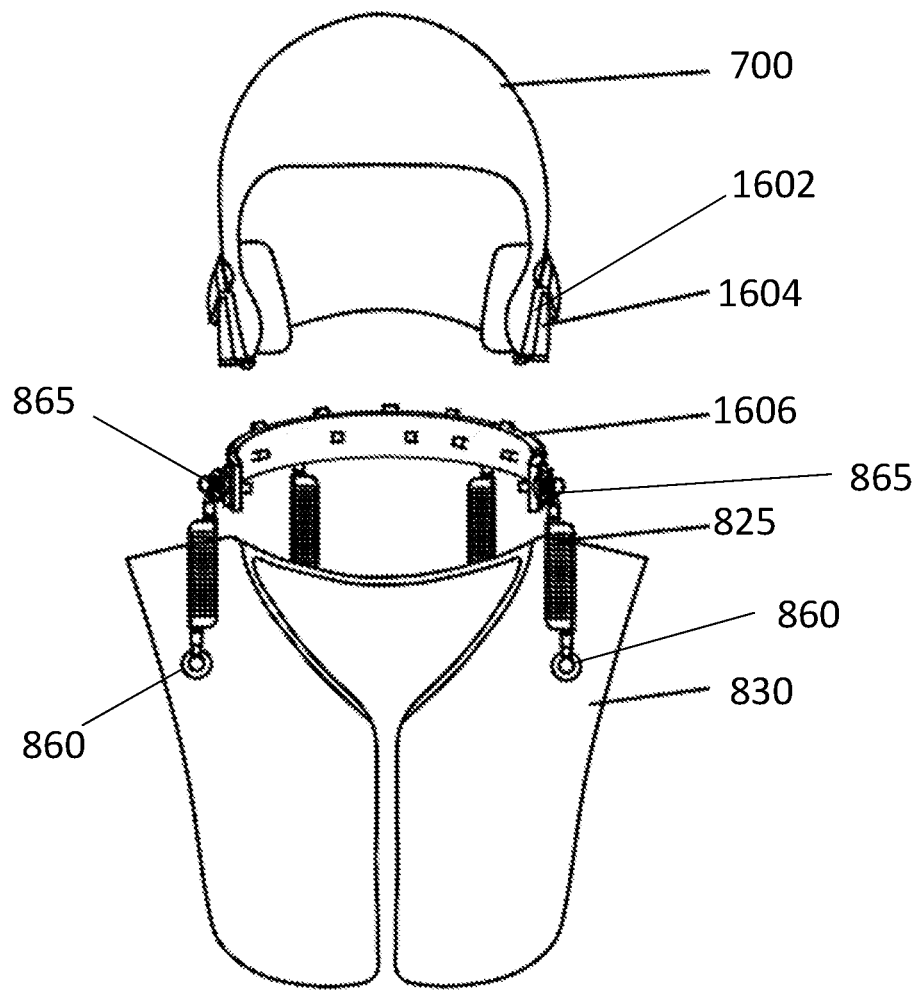
FIG. 30 depicts a front view of the headgear immobilization device according to one or more embodiments shown and described herein.

Referring now to FIGS. 28-32, an example headgear immobilization device for use with an impact protection apparatus of the disclosure is shown. The headgear immobilization device shown is a releasable collar headgear immobilization device 1600. The releasable collar headgear immobilization device 1600 offers an advantage in permitting the helmet 700 to be releasably connected such that the helmet 700 can be removed without necessarily disconnecting the linear lock 825 and associated connections. Thus, as shown in the front exploded view of FIG. 28 and the side exploded view of FIG. 29, the releasable collar headgear immobilization device 1600 can include releasable collar components that can be fixedly engaged during use, but which can also be released such that certain components can be separated from others, permitting the helmet 700 to be relatively easily removed when desired. In an embodiment, therefore, a releasable collar headgear immobilization device 1600 can include a helmet collar base 1602 and a helmet collar connector 1604, each of which can be operationally joined to the helmet as a unit. Thus, as depicted in FIG. 30, the helmet collar base 1602 can be joined, adhered, or otherwise be in conformable contact with the helmet 700 externally, and can provide for a generally conformable surface to mount the helmet collar connector 1604. In an embodiment, the helmet collar connector 1604 can be joined directly to the helmet 700.

Figure 31:
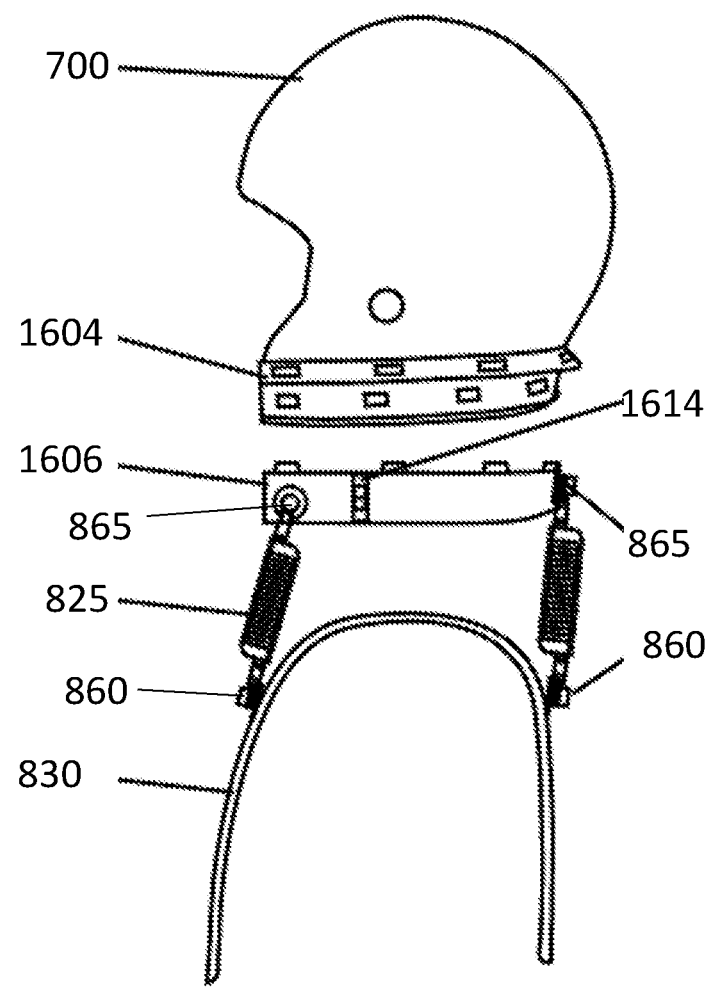
FIG. 31 depicts a left side view of the headgear immobilization device according to one or more embodiments shown and described herein.
Figure 32:
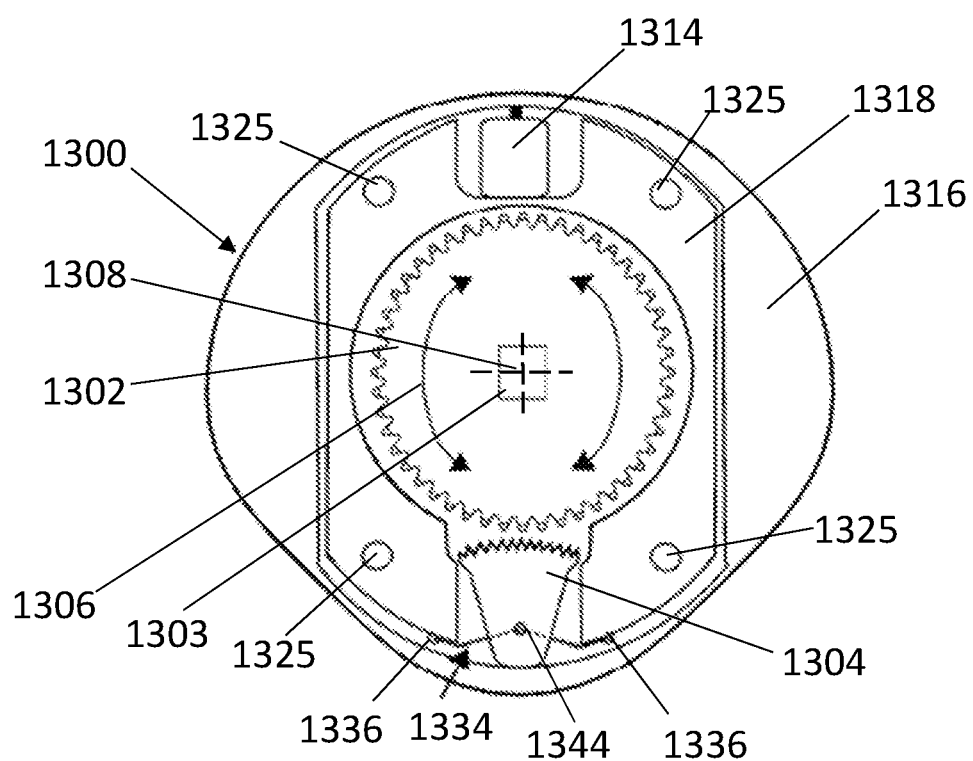
FIG. 32 depicts a top view of a portion of a rotating lock according to one or more embodiments shown and described herein.

Continuing to refer to FIGS. 28-31, a torso collar connector 1606 can be operationally joined to a body connecting member, such as the torso mount 830. As discussed herein, the torso mount 830 may be a shoulder pad, shoulder harness, chest pad, back pad, and or other wearable apparatus which will allow for appropriate mounting. As depicted in FIGS. 30 and 31, the torso collar connector 1606 can be operationally joined to the torso mount 830 by the linear locks 825 and any connection members, as described herein. Thus, one or more individual linear locks 825 can be coupled to torso collar connector 1606 by mount plates 865, as shown in FIG. 9B. One or more torso plates 860 may be used to couple the one or more linear locks 825 to the torso mount 830. Other connection members, such as universal joints, flexible hinges, and other coupling devices can also be implemented as disclosed herein.

The helmet collar connector 1604 and the torso collar connector 1606 can be releasably joinable. In an embodiment, as depicted in FIGS. 28-31, the helmet collar connector 1604 and the torso collar connector 1606 can have complementary mating features, such as tabs 1608 and slots 1610. In an embodiment, the tabs 1608 can correspond in structure and function to the one or more pegs 840 described above with respect to FIGS. 9A and 9B. The tabs 1608 can include a plurality of generally linearly aligned externally disposed, deformable protrusions that can align with corresponding slots 1610 which can be a plurality of openings, including generally rectangular openings. The helmet collar connector 1604 can have a configuration, such as folded over top surface that can define a collar pocket 1612, into which the upper edge of the torso collar connector 1606 can be urged until one or more of the tabs 1608 enter one or more of the slots 1610. In operation, the collar pocket 1612 can aid in guiding the torso collar connector 1606 into the helmet collar connector 1604. The tabs 1608 can be deformable so as to essentially yield flexibly until they are able to snap into the corresponding slots 1610. Once the tabs 1608 are engaged with the slots 1610, helmet 700 is operationally connected by the linear locks 825 to the torso mount 830. When it is desired to remove the helmet 700, one or more of a variety of release mechanisms can be utilized. For example, a release mechanism 1614 can be included on the torso collar connector 1606, which, when operated such as by pressing or pulling, can disengage the complementary mating features, such as the tabs 1608 and slots 1610. The various portions of the releasable collar headgear immobilization device 1600 can each comprise relatively lightweight, durable materials, such as polymer materials, composite materials, metals, and combinations thereof.

Figure 41:
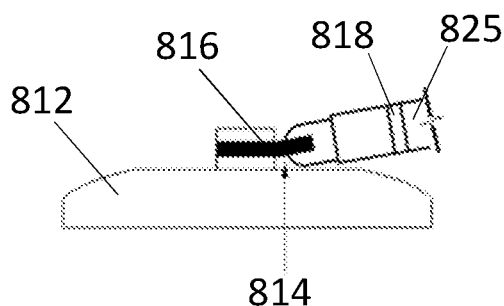
FIG. 41 depicts a side view of a hinge according to one or more embodiments shown and described herein.
Figure 42:
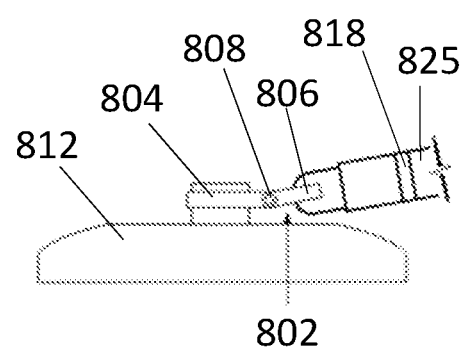
FIG. 42 depicts a side view of a hinge according to one or more embodiments shown and described herein.

Referring back to FIG. 27, each of the ends of the linear lock 825 can be hingedly or flexibly connected to a mounting plate, such as the torso plate 860. The mounting plates can be covered by a plate cover 812 that can provide for protection of the connection components from impacts, debris, and moisture from weather and sweat. In addition to the universal joints described above, such as the one or more upper universal joints 845 and the one or more lower universal joints 880, the hinge connections can include, for example, a pin hinge 802 or a flexible linkage member 814. As also depicted in FIG. 42, the pin hinge 802 can include a first pin hinge portion 804 operationally joined to a mounting plate which can have a plate cover 812. A second pin hinge portion 806 can be joined to the linear lock 825 and is joined to the first pin hinge portion 804 by a pin 808 to facilitate flexible bending about the axis of the pin. As depicted in FIG. 41, the flexible linkage member 814 can directly join the linear lock 825 to a mounting plate (which can have a plate cover 812) by way of the flexible connector 816, which can be a flexible material such as vinyl or other flexible polymer material, and which permits additional degrees of movement and rotation compared to the pin hinge 802. Additionally, the flexible connector can comprise a universal joint, a ball joint, a hinge and socket joint, a pivot joint, a saddle joint, a hinge joint, a cradle joint, a conyloid joint, or combinations thereof. Further depicted in FIG. 27 is a rotating lock 1300 which can be used to couple the linear lock 825 to one of the torso mount 830 or the helmet 700. Additionally, as depicted in FIGS. 41 and 42, the connection can include a swivel joint 818 that permits the linear lock 825 to swivel along its longitudinal axis with the connection to either the flexible linkage member 814 (FIG. 41) or the pin hinge 802 (FIG. 42).

Figure 33:
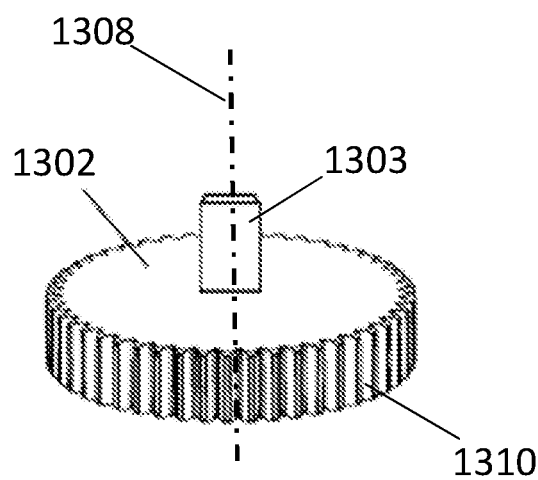
FIG. 33 depicts a perspective view of a gear according to one or more embodiments shown and described herein.
Figure 34:
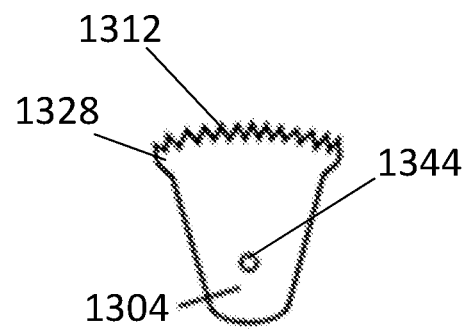
FIG. 34 depicts a top view of a pawl according to one or more embodiments shown and described herein.
Figure 35:
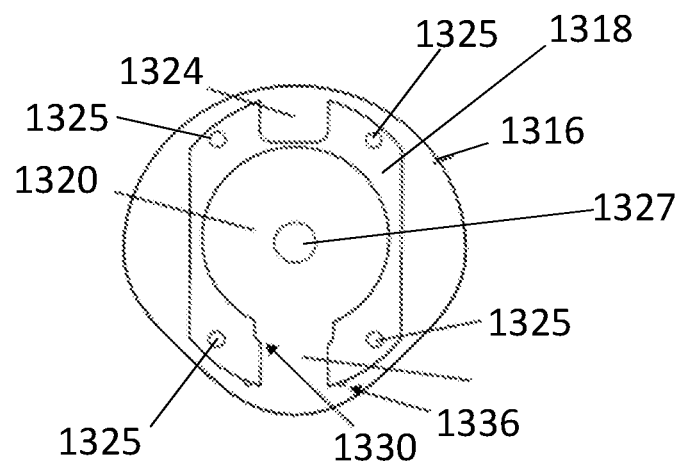
Figure 36:
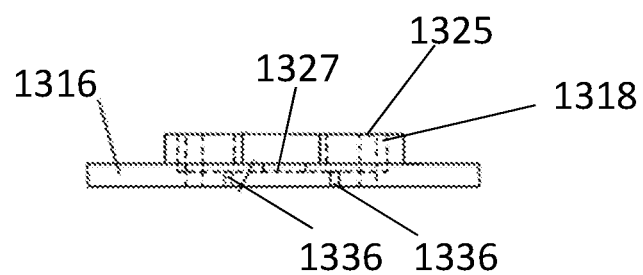
FIG. 36 depicts a side view of a portion of a rotating lock according to one or more embodiments shown and described herein.
Figure 37:
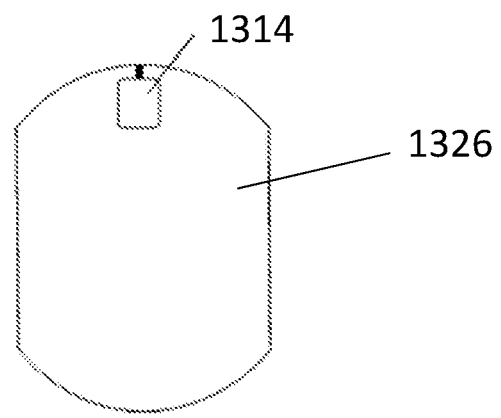
FIG. 37 depicts a top view of actuation connecting member of a rotating lock according to one or more embodiments shown and described herein.
Figure 38:
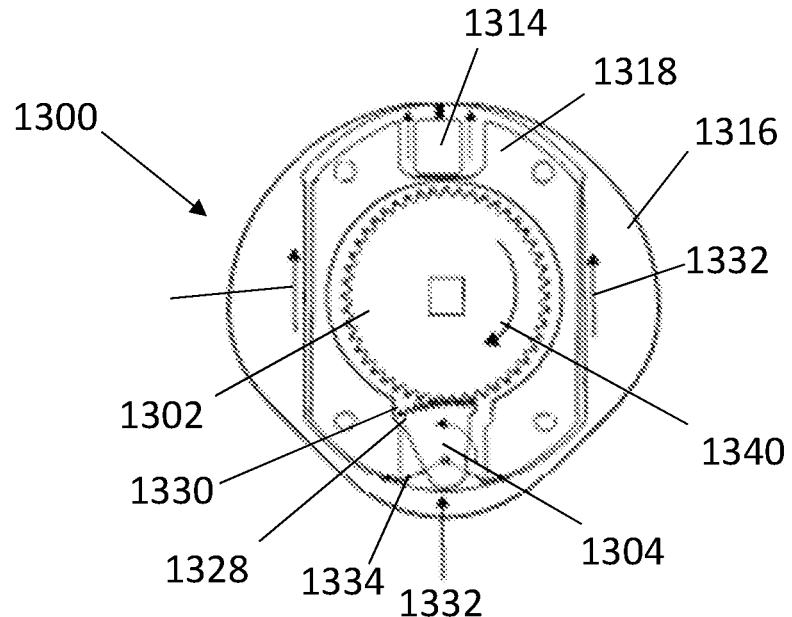
FIG. 38 depicts a top view of a portion of a rotating lock according to one or more embodiments shown and described herein.
Figure 39:
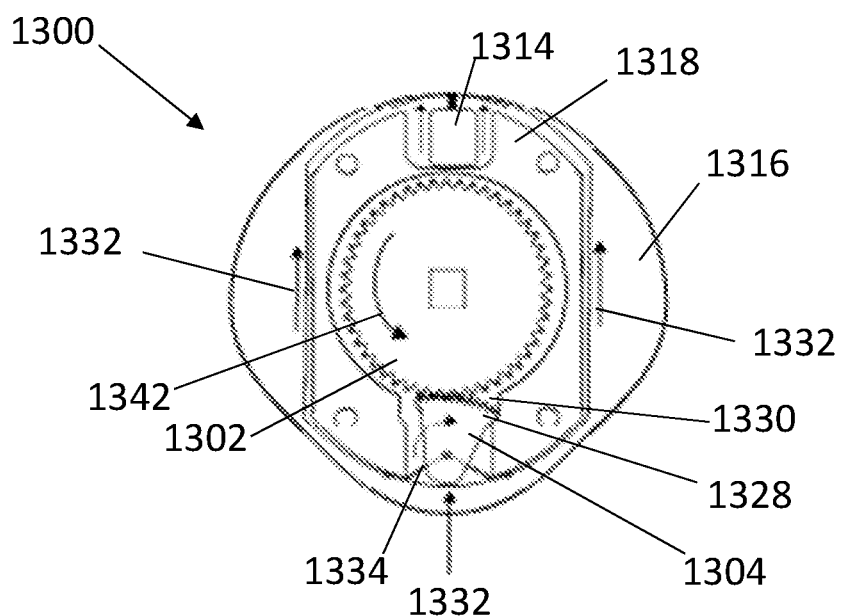
FIG. 39 depicts a top view of a portion of a rotating lock according to one or more embodiments shown and described herein.
Figure 40:
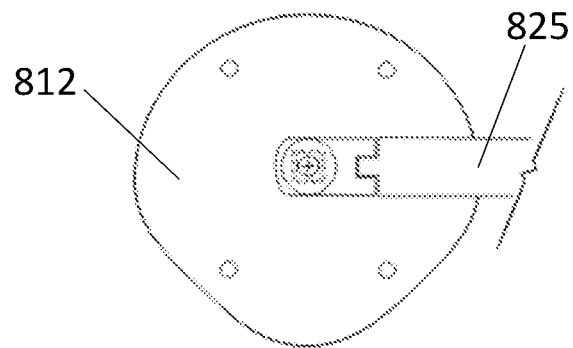
FIG. 40 depicts a top view of a portion of a rotating lock according to one or more embodiments shown and described herein.

Referring now to FIGS. 32-39, a representative example of a rotating lock 1300 is described. The rotating lock 1300 includes a gear 1302 that can rotate freely about its axis 1308 as indicated by the arrows 1306 unless and until it is prevented from doing so by engaging with a pawl 1304 (shown in FIG. 34), which can pivot about pawl pivot 1344. The pawl pivot 1344 can be a pinned connection point, such as a pivot pin or hole, and/or can be a location on which the pivot spring 1334 is connected to the pawl 1304, which can "free float" in the pawl receptacle as described herein. The gear, as shown in FIG. 33, can have a shaft 1303, which can be a square shaft, as shown, which can extend through the cover 812 for connection to, for example, a linear lock. The gear 1302 can also have on the bottom side thereof a protrusion (not shown, but on the other side of gear 1302 in FIG. 33, and in axial alignment with gear axis 1308) that can fit into the shaft opening 1327 on the retaining base 1316. The shaft 1303 can also have a key intended to fit into a keyway (not shown) in the linear lock. Both the gear 1302 and the pawl 1304 can have gear teeth 1310 and pawl teeth 1312, respectively. By urging the pawl teeth 1312 in the direction of, and into a mating relationship with, the gear teeth 1310, the rotational movement of the gear 1302 is prevented. As depicted in FIGS. 38 and 39, when the pawl teeth 1312 engage the gear teeth 1310, further rotation of the gear 1302 in either direction can be stopped. The gear and the pawl can each comprise durable materials, such as steel, hardened steel, polymer materials, composite materials, and combinations thereof.

Referring to FIGS. 32, and 35-39, the rotating lock can have a retaining base 1316 which can be fixedly joined to one of the torso mount 830. The torso mount 830 can be a unitary member, or it can comprise multiple components joined together, similar to, for example, football shoulder pads. Thus, a torso mount can including a plurality of relatively firm mounting plates in combination with relatively resilient pads, flexible materials and straps joined in adjoining sections, the torso collar connector 1606, or the helmet 700, as described above. A receptacle plate 1318 can be in adjacent juxtaposition with the retaining base 1316 to define a plurality of receptacles, including a gear receptacle 1320 in which the gear 1302 resides, a pawl receptacle 1322 in which the pawl 1304 resides, and an actuator receptacle 1324, in which an actuator resides. In an embodiment, the receptacles described herein can be achieved by machining a single piece. For example, the retaining base can be machined to form the various receptacles. Alternatively, in an embodiment, the rotating lock 1300 and/or components thereof can be assembled as layers that can then be stacked and joined to form the structure of receptacles as described herein. Additionally, the receptacle plate can have defined therein a holding notch 1330 into which a portion of the pawl 1304 can enter upon actuation. Likewise, the pawl 1304 can have one or more pawl protrusion 1328 which can be an extension of the pawl that can align with and in the holding notch 1330 when the pawl is actuated. In an embodiment, the pawl can be "free floating" in the rotating lock 1300, constrained by parts above and below in the pawl receptacle 1322, and the pivot spring 1334. Alternatively, if a pawl pivot 1344 includes a pinned connection point, the pin can be received in a hole or a range-limiting slot to permit movement as described herein. A range-limiting slot can be disposed on or in, for example, the retaining base 1316 and/or the actuation connecting member 1326. The retaining base 1316 and the receptacle plate 1318 can be joined to each other and to the torso mount 830, the torso collar connector 1606, or the helmet 700 by fastening, such as through one or more of a plurality of fastening holes 1325. Fastening can include fastening of the plate cover 812 to, for example, a helmet.

The actuation connecting member 1326 can include an actuator 1314, which can be, for example, a push solenoid. The actuator can be push or pull solenoids or any electromagnetic or electrically energized device which can urge the pawl into the gear. The actuator may connect to the pawl by any number of means such as directly, by cable, bellcrank, lever, wedge, cam, and the like. One or more actuators may connect to one or more pawls. When the actuator is activated, such by being triggered by an impact event by one of the switches 10 described herein (or the double impact switch 300, the triple impact switch 405, the daisy chain of impact switches), the actuation connecting member 1326 acts to drive the pawl 1304 in the direction of the arrows 1332, which drives the pawl 1304 toward the gear 1302 and against the spring force of the pivot spring 1334, which can be attached to the pawl at pawl pivot 1344 and to the retaining base 1316 at the plate spring connections 1336. As discussed above, once the pawl teeth 1312 of the pawl 1304 engage the gear teeth 1310 of the gear 1302, the pawl 1304 can pivot about pawl pivot 1344 until the pawl protrusion 1328 contacts the holding notch 1330 and is prevented by the holding notch 1330 from any additional free rotation of the gear 1302. Thus, as depicted in FIG. 38 free rotation of the gear 1302 in the clockwise direction indicated by arrow 1340 is stopped. Likewise, as depicted in FIG. 39 free rotation of the gear 1302 in the counter-clockwise direction indicated by arrow 1342 is stopped.

In an embodiment, once the triggering event ends, the actuation connecting member 1326 returns to an unactivated position, and the pawl 1304 retracts away from the gear 1302 under the spring force of the pivot spring 1334, and the gear 1302 is again free to rotate.

As can be understood, when a linear lock 825, or any other IAD or IPA component is operationally connected to the gear 1302, once a triggering event occurs and the actuation connecting member 1326 drives the pawl teeth 1312 into the gear teeth 1310, any further rotational motion of the linear lock 825 stops, which in turn stops rotational movement of the operationally connected component. Thus, when the rotational lock is activated, the helmet of a user can be prevented from any further articulation that relies on the free rotation of the gear 1302. Such immobilization can be used independently, or in conjunction with the linear locks disclosed herein to achieve a greater degree of immobilization upon the triggering of one or more of the switches in an impact event, as described herein.

Figure 43:
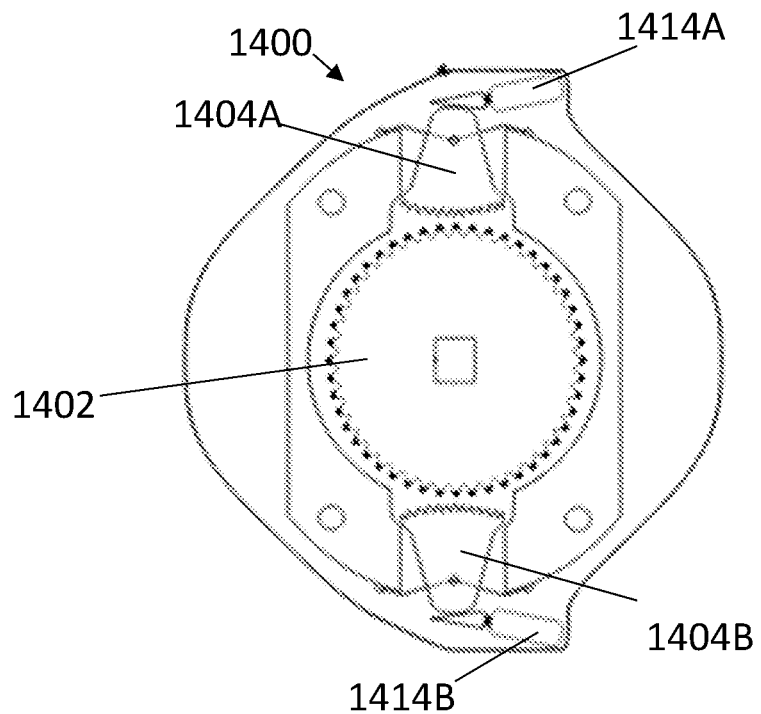
FIG. 43 depicts a top view of a portion of a rotating lock according to one or more embodiments shown and described herein.
Figure 44A:
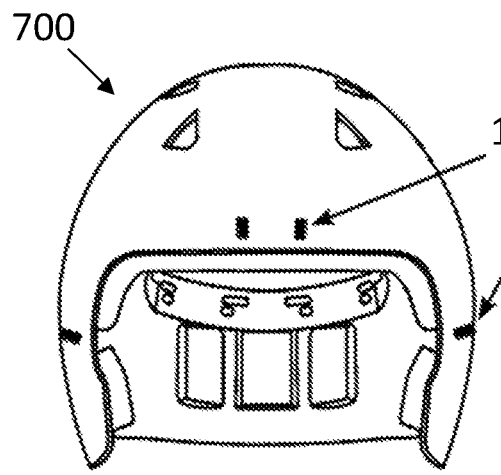
FIG. 44A depicts a front view of a helmet according to one or more embodiments shown and described herein.
Figure 44B:
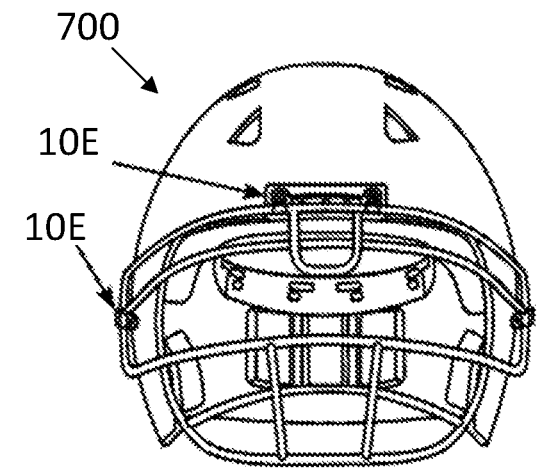
FIG. 44B depicts a front view of a helmet according to one or more embodiments shown and described herein.
Figure 44C:
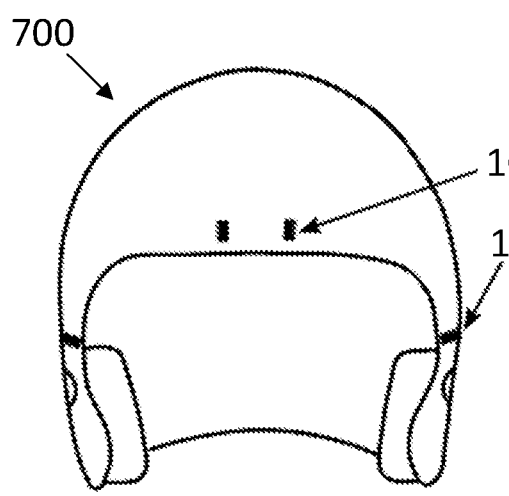
FIG. 44C depicts a front view of a helmet according to one or more embodiments shown and described herein.
Figure 44D:
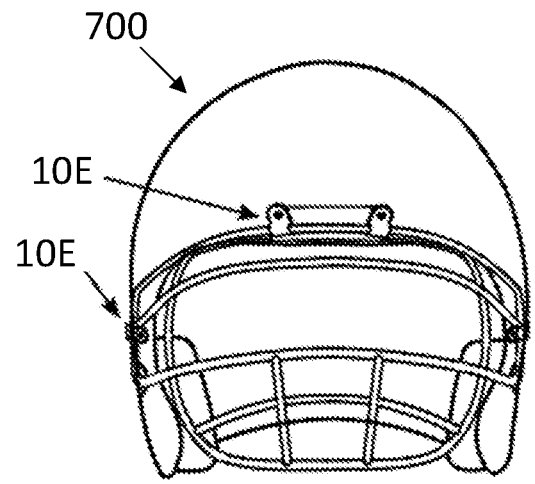
FIG. 44D depicts a front view of a helmet according to one or more embodiments shown and described herein.
Figures 45A, 45B:
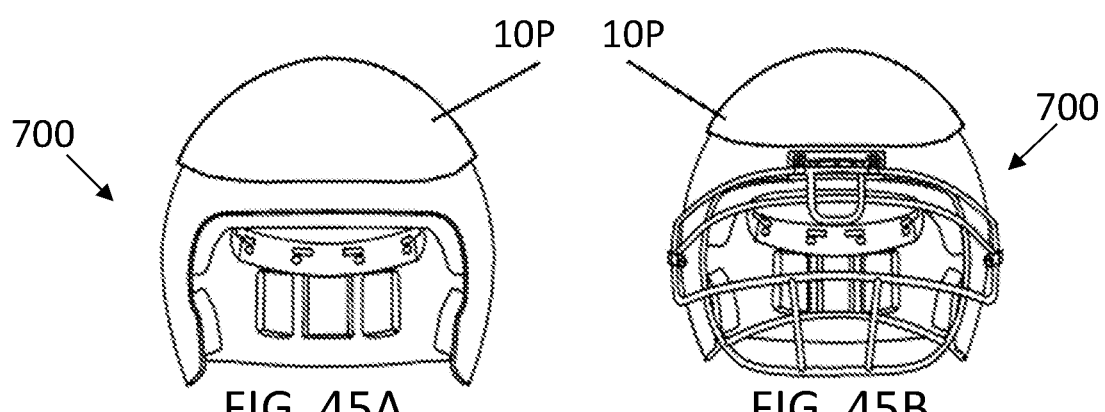
FIG. 45A depicts a front view of a helmet according to one or more embodiments shown and described herein.
FIG. 45B depicts a front view of a helmet according to one or more embodiments shown and described herein.
Figures 45C, 45D:
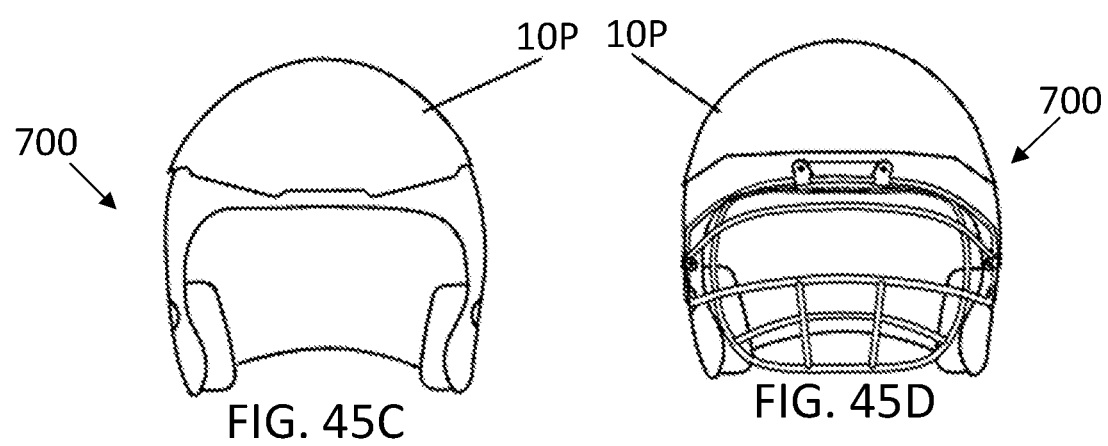
FIG. 45C depicts a front view of a helmet according to one or more embodiments shown and described herein.
FIG. 45D depicts a front view of a helmet according to one or more embodiments shown and described herein.
Figures 45E, 45F:
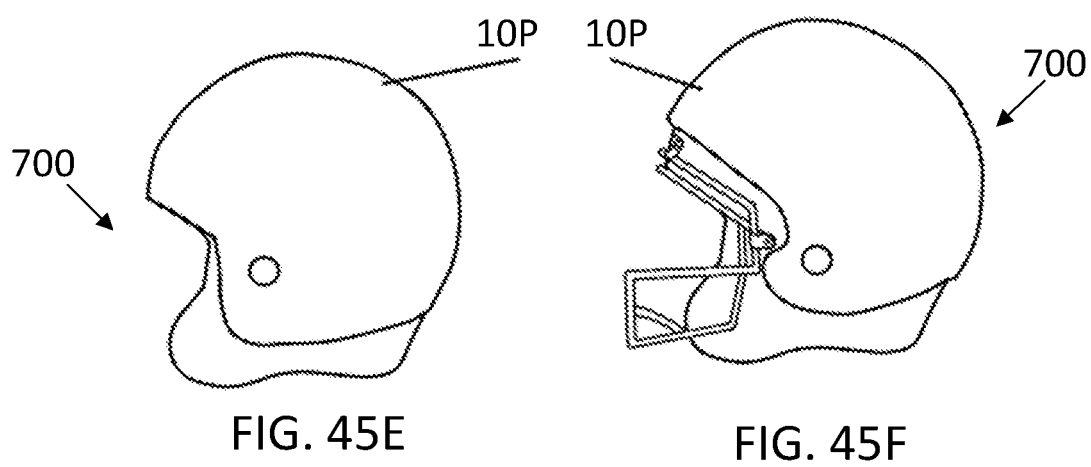
FIG. 45E depicts a side view of a helmet according to one or more embodiments shown and described herein.
FIG. 45F depicts a side view of a helmet according to one or more embodiments shown and described herein.

Referring now to FIG. 43 there is shown another example embodiment of a rotating lock 1400 which includes the features described above, including a gear 1402 that can rotate freely about its axis. Other features are not described in detail here, but correspond to the description above. However, the embodiment shown in FIG. 43 illustrates that a plurality of pawls 1404 can be utilized. In the illustrated embodiment, a first pawl 1404A and a second pawl 1404B are each configured to engage the gear 1402 as described above, to stop rotational motion of the gear 1402 upon a triggering event. A first actuator 1414A, which can be a paddle solenoid, can be activated to urge the first pawl 1404A toward the gear 1402. Likewise, a second actuator 1414B, which can be a paddle solenoid, can be activated to urge second pawl 1404B toward the gear 1402. First and second pawls (and any other pawls) can be urged toward the gear 1402 by any mechanical, electro-mechanical, and/or fluid dynamical devices.

Referring now to FIGS. 44A-44D, there is shown representative placements for impact switches for the IAD or IPA, which can be in every way as described above with respect to the impact switch 10, but are disposed externally to the helmet 700, and can be described as external impact switches 10E. The external impact switches 10E can be triggered by impacts (as discussed above herein) to the facemask or whatever other mounted part may be on helmets/headgear, such as but not limited to sun visors, face visors, additional impact protection layers, and the like. The external switches 10E can be activated by impact or pressure. Thus, in an embodiment, the external switches 10E may be momentary and/or tactile switches that are energized by pressure coming from being pressed on by what they are mounted to. Thus, the external switches 10E may be temporarily triggered once a threshold force is experienced, either due to relatively slow pressure, or by relatively quick impact. Such switches may also be located and mounted to the internal surfaces of the protective headgear and/or the internal padding thereof, whereby they can be triggered by force thresholds reached by the user's head.

Referring now to FIGS. 45A-45F, there is shown representative impact switches for the IAD or IPA, which can operate as described above with respect to the impact switch 10, but are disposed externally to the helmet 700 as mounted with plates, and can be described as plate impact switches 10P. The plate impact switches 10P can be triggered by impacts (as discussed above herein) to the helmet 700. The plate impact switches 10P can be one or more plates, and can be of differing sizes and dimensions. The plate impact switches 10P can incorporate conductive material or be conductive material, or push or pull upon a connected electric switch to realize activation/triggering.

Figure 46:
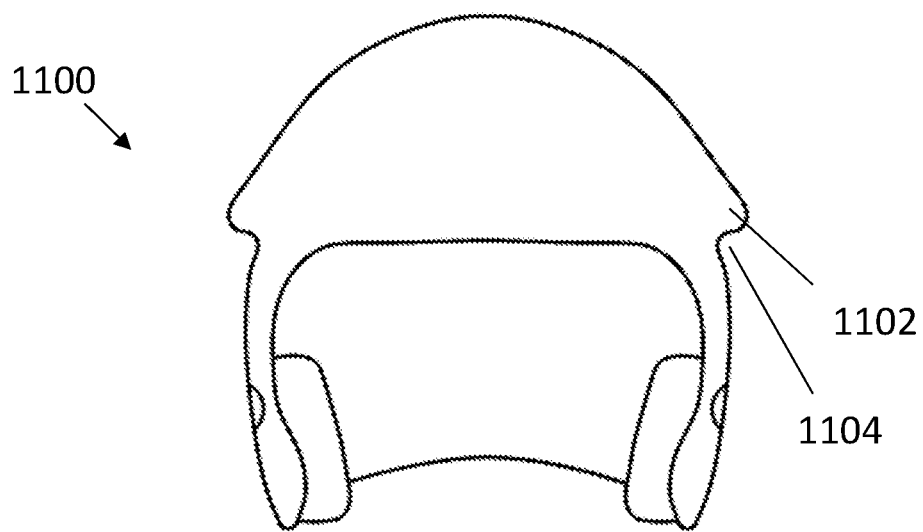
FIG. 46 depicts a front view of a helmet according to one or more embodiments shown and described herein.
Figure 47:
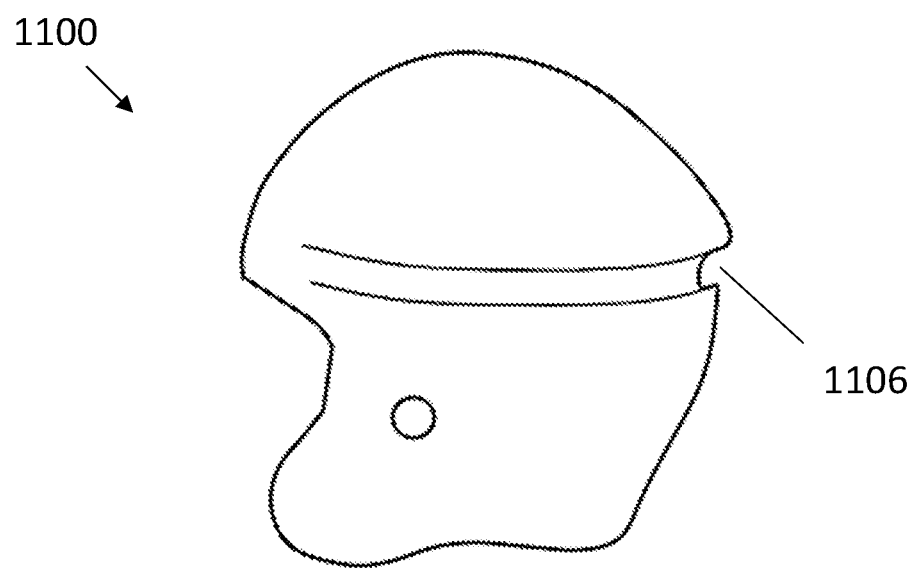
FIG. 47 depicts a side view of a helmet according to one or more embodiments shown and described herein.

Referring now to FIGS. 46 and 47 there is shown two examples of helmets that include features that can be sized, shaped, and contoured to receive portions of the linear locks, including the mounting portions. For example, as shown in FIG. 46, a contoured helmet 1100 can have a helmet protrusion 1102 that defines a pocket recess 1104 in which portions of the linear locks can join to the contoured helmet 1100. The contoured helmet 1100 can have a generally smooth top that follows the general contours of a football helmet, for example, and which flairs out to form the helmet protrusion 1102, and then tucks inwardly, and, in an embodiment, upwardly to define the pocket recess 1104. The sides of the contoured helmet 1100 below the pocket recess 1104 can have the size, shape, and contour of the desired helmet, for example, that of a football helmet. The helmet protrusion can follow that shape of the contoured helmet 1100 substantially fully around from one side to the other (e.g., the left side, around the back, and to the right side as viewed in FIG. 46). In an embodiment, the helmet protrusion 1102 can comprise multiple protrusions separated by areas not having a helmet protrusion.

Another example embodiment of a contoured helmet 1100 is depicted in FIG. 47. The contoured helmet 1100 of FIG. 47 includes a helmet recess 1106. Portions of the contoured helmet 1100 can be inwardly situated a relatively depressed portion, such as in a groove, for example, to define the helmet recess 1106, into which portions of the linear locks can be mounted. In an embodiment, the helmet recess 1106 has a size and shape sufficient for substantially all of a linear lock mounting portion to reside. In an embodiment, the helmet recess 1106 has a size and shape sufficient for substantially all of a linear lock mounting portion to reside while maintaining a substantially smooth overall outer surface of the contoured helmet 1100. The helmet recess 1106 can follow that shape of the contoured helmet 1100 substantially fully around from one side to the other (e.g., from the left side, as viewed in FIG. 47, around the back, and to the right side). In an embodiment, the helmet recess 1106 can comprise multiple recesses separated by areas not having a helmet recess. In general, the helmet protrusion 1102 and/or the helmet recess 1106, can, in addition to providing for mounting portions on the exterior of the contoured helmet 1100, serve to allow for additional interior padding to help further protect the user's head from impacts.

Figure 48:
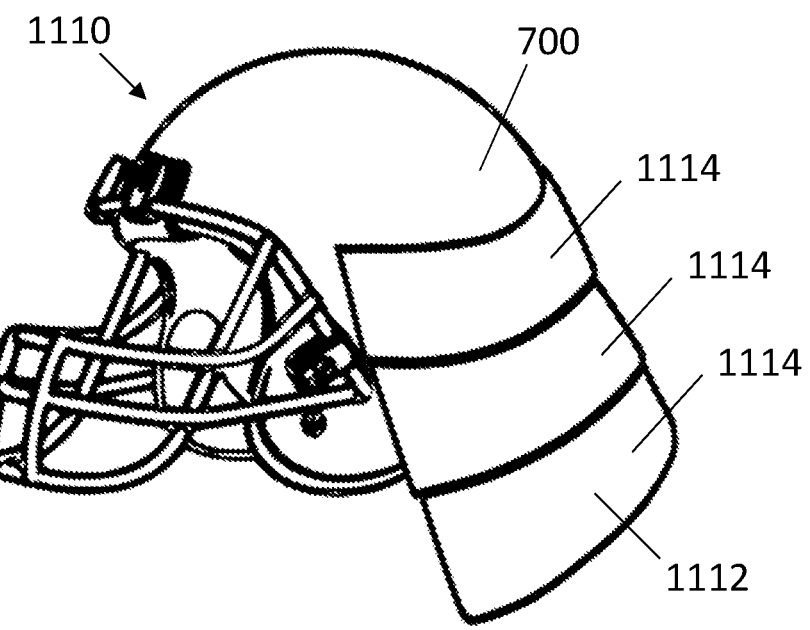
FIG. 48 depicts a perspective view of a helmet according to one or more embodiments shown and described herein.

Referring now to FIG. 48, there is depicted a shrouded helmet 1110. In the example embodiment shown, a shroud 1112 is joined to a helmet 700. The shroud 1112 can provide protection to portions of an IAD or IPA that mount to the helmet 700 (or 1100, or other helmets) from contact, such as from hands of players, for example, that may grab the mounting portions of the linear locks. The shroud 1112 can comprise a plurality of shroud strips 1114 that can be made of semi-rigid or rigid materials, such as plastic. The shroud strips 1114 can be joined to form a relative flexible rigid shield over portions of the helmet 700. The shroud 1112 can have a size and shape sufficient to be joined to the helmet 700 above connecting portions of any helmet-connected hardware, and extend downwardly sufficient to cover the bottom of the helmet 700, and, in some embodiments, sufficient to cover the head and shoulders of the user. In an embodiment, the shroud strips 1114 can be mounted with fasteners, such as cord or wire, or can be shaped and/or molded to be fastened, such that they permit movement of the users head and shoulders during use. The shroud 1112 can comprise a plurality of shroud strips 1114 which can be oriented vertically, horizontally, or in a combination of horizontal and vertical strips. The shroud strips can be overlapping, side-by-side, or even have a small gap.

Figure 49:
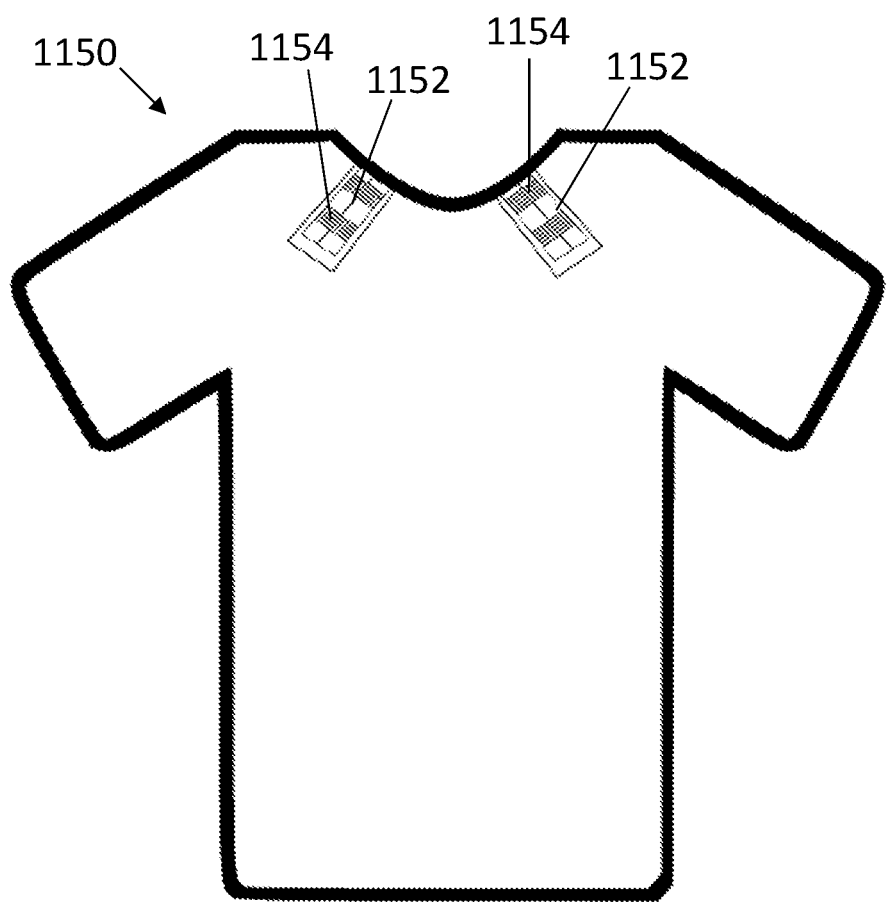
FIG. 49 depicts a perspective front of a garment according to one or more embodiments shown and described herein.

Referring now to FIG. 49, there is shown a garment for use with an IAD or IPA of the disclosure. The garment 1150 can be a shirt, or jersey, and can have any of the variations known in the art of shirts with respect to size, shape, neckline size and shape, sleeve size and shape, material, and the like. The garment 1150 can have disposed thereon in at least one place a portion defining a garment opening 1152, which can be a slit that allows passage of a portion of the IAD or IPA, for example, the connecting portions of the linear locks, to pass through the garment and be attached for use inside the garment, for example, onto the torso mount 830. The garment opening(s) 1152, two of which are depicted in FIG. 49, can be slits, slots, and can be located anywhere on the garment 1150. The garment opening 1152 can be reinforced with additional material, stitching, and the like. The garment opening 1152 can include a closure member 1154 that can be used to close all or a portion of the garment opening 1152. The closure member 1154 may be a cord, lace, button, zipper, hook and loop fastener, clasp, magnet, wire, cable, and combinations thereof.

While particular embodiments have been illustrated and described herein, it should be understood that various other changes and modifications may be made without departing from the spirit and scope of the claimed subject matter. For example, there may be use cases where the G-forces experienced by the user are not sudden, but gradual in nature and/or are so high that some injury is expected. In such cases it may be preferred that the locking mechanisms remain engaged for a longer period so as to prevent further body movement which may cause more injury. Additionally, while the examples herein describe connection to a body-worn member, such as the torso mount, the distal end of the linear locks and the rotating locks can also be connected to other things, such as the frame of vehicles such as cars, boats, airplanes, helicopters, and rockets. Thus, the proximal end of the linear and or rotating locks can be the end that mounts to the protective headgear, e.g., the helmet, and the distal end can be what mounts to an external frame. In an example, a user may be a driver and/or passenger in or on a vehicle such, as but not limited to, an automobile, an airplane, a helicopter, and a boat. The proximal end of a linear and/or rotating lock may be mounted to the user's helmet and the distal end may be mounted to structures located around the user in any direction around, above, below, the front or back, and the like. Such structures can include, but not be limited to, the seat, frame structures, cross members, roof, door, sliding structures and panels.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

Certain terminology is used in the disclosure for convenience only and is not limiting. The words "left", "right", "front", "back", "upper", and "lower" designate directions in the drawings to which reference is made. The terminology includes the words noted above as well as derivatives thereof and words of similar import.

The present disclosure may be embodied in hardware and/or in software (including firmware, resident software, micro-code, etc.). The system controller may have at least one processor and the computer-readable medium. A computer-usable or the computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM) or other applicable mediums. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Computer program code for carrying out operations of the present disclosure may be written in a high-level programming language, such as C or C++, for development convenience. In addition, computer program code for carrying out operations of the present disclosure may also be written in other programming languages, such as, but not limited to, interpreted languages. Some modules or routines may be written in assembly language or even micro-code to enhance performance and/or memory usage. However, software embodiments of the present disclosure do not depend on implementation with a particular programming language. It will be further appreciated that the functionality of any or all of the program modules may also be implemented using discrete hardware components, one or more application specific integrated circuits (ASICs), or a programmed digital signal processor or microcontroller.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

The invention claimed is:

1. An impact protection apparatus (IPA) to reduce the likelihood of head and vertebral column injuries, the IPA comprising:
   an impact switch configured to transition from an open-circuit state to a close-circuit state when a force is exerted on the IPA in a first direction and exceeds a force threshold;
   a headliner configured to couple with a protective headgear, the headliner comprising an electronic circuit electrically coupled to the impact switch, wherein the electronic circuit is configured to transmit a trigger signal when the force threshold is exceeded; and
   a headgear immobilization device electrically coupled to the electronic circuit, the headgear immobilization device comprising:
      a mount plate coupled to the protective headgear,
      a torso mount coupled to the mount plate by a linear lock configured to be triggered by the trigger signal, the linear lock comprising:
         a lock housing having a first lock end and a second lock end distal to the first lock end,
         a mount with a first mount end and a second mount end, the first mount end is coupled to the first lock end,
         a rod with a first rod end and a second rod end, a plurality of substantially parallel grooves are disposed along the rod between the first rod end and the second rod end, the first rod end travels through a housing aperture at the second lock end, and the second rod end is coupled to the torso mount, and
      a rotating lock configured to be triggered by the trigger signal, the rotating lock comprising:
         a retaining base coupled to the mount plate, a gear rotatable on the retaining base about a gear axis, the gear comprising gear teeth and a gear shaft coupled to the second mount end, a pawl that is translatable on the retaining base in a direction toward the gear, the pawl having pawl teeth, an actuation connecting member coupled to the pawl, an actuator coupled to the actuation connecting member, and wherein the actuator is actuated by the electronic circuit to urge the actuation connecting member to translate the pawl toward the gear until the pawl teeth engage the gear teeth.

2. The IPA of claim 1, wherein the linear lock further comprises an interrupter mechanism is disposed within a platform, the platform is disposed within the lock housing and slideably couples with the rod, the interrupter mechanism is configured to restrict travel of the rod by engaging an individual groove of the plurality of substantially parallel grooves when the trigger signal is received thereby restricting movement of the protective headgear in relation to the torso mount.

3. The IPA of claim 1, wherein the impact switch comprises a hub, the hub comprising:
a hub base having a central axis centered in the hub base, and
a conductive body with a body axis coupled to the hub base, the body axis lies along the central axis;
a conductive member coupled to the hub base along the central axis;
a first wire electrically coupled to the conductive member; and
a second wire electrically coupled to the conductive body.

4. The IPA of claim 1, further comprising:
a second switch with a second force threshold coupled to the headliner and configured to determine when a second force is exerted on the IPA in a second direction;
a third switch with a third force threshold coupled to the headliner and configured to determine when a third force is exerted on the IPA in a third direction;
a fourth switch with a fourth force threshold coupled to the headliner and configured to determine when a fourth force is exerted on the IPA in a fourth direction; and
a fifth switch with a fifth force threshold coupled to the headliner and configured to determine when a fifth force is exerted on the IPA.

5. The IPA of claim 4, wherein the first direction, the second direction, and the third direction are a same direction; and
an indicator circuit further comprises a first LED, a second LED, and a third LED, the indicator circuit is configured to illuminate and indicate a magnitude of the force along the same direction by illuminating the first LED if the force threshold is exceeded, illuminating the second LED if the second force threshold is exceeded, and illuminating the third LED if the third force threshold is exceeded.

6. The IPA of claim 1, further comprising a second impact switch, wherein the second impact switch is mounted externally to the protective headgear.

7. The IPA of claim 1, further comprising a plate impact switch mounted externally to the protective headgear.

8. The IPA of claim 1, wherein the protective headgear comprises a helmet recess into which portions of the linear lock can be mounted.

9. The IPA of claim 1, wherein the protective headgear comprises a shroud joined thereto, the shroud comprising a plurality of shroud strips joined in a flexible shield.

10. An impact protection device (IPA), the IPA comprising:
an impact switch configured to transition from an open-circuit state to a close-circuit state when a force is exerted on the IPA in a first direction and exceeds a force threshold;
a headliner configured to couple with a protective headgear, the headliner comprising an electronic circuit electrically coupled to the impact switch and wherein when the force threshold is exceeded the electronic circuit transmits an indication signal and a trigger signal; and
a headgear immobilization device electrically coupled to the electronic circuit, the headgear immobilization device comprising:
a helmet collar connector coupled to the protective headgear, the helmet collar connector comprising a plurality of slots, and
a torso collar connector comprising a plurality of tabs being engagable with the plurality of slots, the torso collar connector being coupled to a torso mount by one or more linear locks, each linear lock being triggered by the trigger signal and comprising:
a mount with a first mount end and a second mount end, the first mount end is coupled to a first lock end and the second mount end is coupled to the torso collar connector, and
a rod with a first rod end and a second rod end, a plurality of substantially parallel grooves are disposed along the rod between the first rod end and the second rod end, the second rod end is coupled to the torso mount.

11. The IPA of claim 10, wherein each linear lock of the one or more linear locks further comprises an interrupter mechanism is disposed within a platform, the platform is disposed within a lock housing and slideably couples with the rod, the interrupter mechanism is configured to restrict travel of the rod by engaging an individual groove of the plurality of substantially parallel grooves when the trigger signal is received thereby restricting movement of the protective headgear in relation to the torso mount.

12. The IPA of claim 10, wherein the impact switch comprises a hub, the hub comprising:
a hub base having a central axis centered in the hub base, and
a conductive body with a body axis coupled to the hub base, the body axis lies along the central axis;
a conductive member coupled to the hub base along the central axis;
a first wire electrically coupled to the conductive member; and
a second wire electrically coupled to the conductive body.

13. The IPA of claim 10, further comprising:
a second switch with a second force threshold coupled to the headliner and configured to determine when a second force is exerted on the IPA in a second direction;
a third switch with a third force threshold coupled to the headliner and configured to determine when a third force is exerted on the IPA in a third direction;
a fourth switch with a fourth force threshold coupled to the headliner and configured to determine when a fourth force is exerted on the IPA in a fourth direction; and a fifth switch with a fifth force threshold coupled to the headliner and configured to determine when a fifth force is exerted on the IPA.

14. The IPA of claim 10, further comprising a second impact switch, wherein the second impact switch is mounted externally to the protective headgear.

15. The IPA of claim 10, further comprising a plate impact switch mounted externally to the protective headgear.

16. The IPA of claim 10, wherein the protective headgear comprises a helmet recess into which portions of the linear lock can be mounted.

17. The IPA of claim 10, wherein the protective headgear comprises a shroud joined thereto, the shroud comprising a plurality of shroud strips joined in a flexible shield.

18. The IPA of claim 10, wherein the protective headgear further comprises one or more rotating locks, each rotating lock comprising:
   a retaining base coupled to the torso collar connector;
   a gear rotatable on the retaining base about a gear axis, the gear comprising gear teeth and further comprising a gear shaft coupled to the second mount end at the torso collar connector;
   a pawl translatable on the retaining base in a direction toward and away from the gear, the pawl having pawl teeth;
   an actuation connecting member coupled to the pawl;
   an actuator coupled to the actuation connecting member; and
   wherein the actuator is actuated by the electronic circuit to urge the actuation connecting member to translate the pawl toward the gear until the pawl teeth engage the gear teeth.

19. The IPA of claim 18, wherein the actuator is selected from the group consisting of a push solenoid, a pull solenoid, an electromagnet, a magnet, a compression spring, and combinations thereof.

20. The IPA of claim 18, wherein a rotating lock of the one or more rotating locks further comprising:
   a second pawl that is translatable on the retaining base in a direction toward and away from the gear, the second pawl having second pawl teeth;
   a second actuation connecting member coupled to the second pawl;
   a second actuator coupled to the second actuation connecting member; and
   wherein the second actuator is actuated by the electronic circuit to urge the second actuation connecting member to translate the second pawl toward the gear until the second pawl teeth engage the gear teeth.

* * * * *